US012493044B2

(12) United States Patent
Taipale et al.

(10) Patent No.: US 12,493,044 B2
(45) Date of Patent: Dec. 9, 2025

(54) METHODS AND KITS FOR IDENTIFYING A PROTEIN ASSOCIATED WITH RECEPTOR-LIGAND INTERACTIONS

(71) Applicant: The Governing Council of the University of Toronto, Toronto (CA)

(72) Inventors: Mikko Taipale, Toronto (CA); Jason Moffat, Toronto (CA); Hunsang Lee, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 1181 days.

(21) Appl. No.: 17/059,349

(22) PCT Filed: May 30, 2019

(86) PCT No.: PCT/CA2019/050747
§ 371 (c)(1),
(2) Date: Nov. 27, 2020

(87) PCT Pub. No.: WO2019/227222
PCT Pub. Date: Dec. 5, 2019

(65) Prior Publication Data
US 2021/0148923 A1 May 20, 2021

Related U.S. Application Data

(60) Provisional application No. 62/677,875, filed on May 30, 2018.

(51) Int. Cl.
*G01N 33/68* (2006.01)
*C07K 14/21* (2006.01)
(Continued)

(52) U.S. Cl.
CPC ......... *G01N 33/6845* (2013.01); *C07K 14/21* (2013.01); *C07K 14/34* (2013.01);
(Continued)

(58) Field of Classification Search
None
See application file for complete search history.

(56) References Cited

U.S. PATENT DOCUMENTS

2017/0204407 A1* 7/2017 Gilbert et al. ..... C12N 15/1082

FOREIGN PATENT DOCUMENTS

JP 2010-075194 A 4/2010
WO WO-0066755 A2 * 11/2000 ........... C07K 14/325
(Continued)

OTHER PUBLICATIONS

Brown, K. J. et al. The human secretome atlas initiative: implications in health and disease conditions. Biochimica et biophysica acta 1834, 2454-2461, doi:10.1016/j.bbapap.2013.04.007 (2013).
(Continued)

*Primary Examiner* — Kaijiang Zhang
(74) *Attorney, Agent, or Firm* — Smart & Biggar LP; Carmela De Luca

(57) ABSTRACT

A method for identifying a protein associated with a receptor-ligand interaction is described. The method comprises providing a population of engineered cells comprising a targeting library targeting specific gene expression, contacting the population of cells with a recombinant toxin fusion for sufficient time, and identifying proteins in the selection pool of cells by sequencing one or more of the nucleic acid molecule comprised in the selection pool of cells, thereby identifying the target gene. Toxin-resistant cell lines, toxin-producing cell lines, recombinant toxin fusions, probes and methods producing same, and kits thereof, are also provided.

20 Claims, 21 Drawing Sheets

Specification includes a Sequence Listing.

(51) Int. Cl.
*C07K 14/34* (2006.01)
*C12N 9/52* (2006.01)
*C12N 15/90* (2006.01)
*G01N 33/50* (2006.01)

(52) U.S. Cl.
CPC ............. *C12N 9/52* (2013.01); *C12N 15/907* (2013.01); *G01N 33/5041* (2013.01); *C07K 2319/00* (2013.01); *C12N 2310/20* (2017.05); *C12N 2800/80* (2013.01)

(56) References Cited

FOREIGN PATENT DOCUMENTS

| | | | | |
|---|---|---|---|---|
| WO | 2004099254 | A2 | 11/2004 | |
| WO | 2011006145 | A2 | 1/2011 | |
| WO | WO-2018060238 | A1 * | 4/2018 | ........... C12N 15/102 |

OTHER PUBLICATIONS

Ben-Shlomo, I. et al. Signaling receptome: a genomic and evolutionary perspective of plasma membrane receptors involved in signal transduction. Science's STKE: signal transduction knowledge environment 2003, RE9, doi:10.1126/stke.2003.187.re9 (2003).
Meissner, F. et al. Direct proteomic quantification of the secretome of activated immune cells. Science 340, 475-478, doi:10.1126/science.1232578 (2013).
Christopoulos, A. Allosteric binding sites on cell-surface receptors: novel targets for drug discovery. Nature reviews. Drug discovery 1, 198-210, doi:10.1038/nrd746 (2002).
Ramilowski, J. A. et al. A draft network of ligand-receptor-mediated multicellular signalling in human. Nature communications 6, 7866, doi:10.1038/ncomms8866 (2015).
Kerr, J. S. et al. Avidity-based extracellular interaction screening (AVEXIS) for the scalable detection of low-affinity extracellular receptor-ligand interactions. Journal of visualized experiments : JoVE, e3881, doi:10.3791/3881 (2012).
Michalska, M. et al. Pseudomonas Exotoxin A: optimized by evolution for effective killing. Frontiers in microbiology 6, 963, doi:10.3389/fmich.2015.00963 (2015).
Carette, J. E. et al. Haploid genetic screens in human cells identify host factors used by pathogens. Science 326, 1231-1235, doi:10.1126/science.1178955 (2009).
Hu, Y. et al. Specific killing of CCR9 high-expressing acute T lymphocytic leukemia cells by CCL25 fused with PE38 toxin. Leukemia research 35, 1254-1260, doi:10.1016/j.leukres.2011.01.015 (2011).
Weldon, J. E. et al. A guide to taming a toxin—recombinant immunotoxins constructed from Pseudomonas exotoxin A for the treatment of cancer. The FEBS journal 278, 4683-4700, doi:10.1111/j.1742-4658.2011.08182.x (2011).
Foss, F. M. DAB(389)IL-2 (Ontak): a novel fusion toxin therapy for lymphoma. Clinical lymphoma 1, 110-116; discussion 117 (2000).
Pasetto, M. et al. Whole-genome RNAi screen highlights components of the endoplasmic reticulum/Golgi as a source of resistance to immunotoxin-mediated cytotoxicity. Proceedings of the National Academy of Sciences of the United States of America 112, E1135-1142, doi:10.1073/pnas.1501958112 (2015).
Jae, L. T. et al. Deciphering the glycosylome of dystroglycanopathies using haploid screens for lassa virus entry. Science 340, 479-483, doi:10.1126/science.1233675 (2013).
Mitamura , T. et al. Diphtheria toxin binds to the epidermal growth factor (EGF)-like domain of human heparin-binding EGF-like growth factor/diphtheria toxin receptor and inhibits specifically its mitogenic activity. The Journal of biological chemistry 270, 1015-1019 (1995).
Hart, T. et al. High-Resolution CRISPR Screens Reveal Fitness Genes and Genotype-Specific Cancer Liabilities. Cell 163, 1515-1526, doi:10.1016/j.cell.2015.11.015 (2015).
Korf-Klingebiel, M. et al. Myeloid-derived growth factor (C19orf10) mediates cardiac repair following myocardial infarction. Nature medicine 21, 140-149, doi:10.1038/nm.3778 (2015).
Li, W. et al. MAGeCK enables robust identification of essential genes from genome-scale CRISPR/Cas9 knockout screens. Genome biology 15, 554 (2014).
Fujisawa, T. et al., "Targeting IL-13Ra2 in human pancreatic ductal adenocarcinoma with combination therapy of IL-13-PE and gemcitabine". International Journal of Cancer, Mar. 1, 2011 (Mar. 1, 2011), vol. 128(5), pp. 1221-1231, ISSN 0020713.
Winter, S.V. et al. Genome-wide CRISPR screen reveals novel host factors required for Staphylococcus aureus alpha-hemolysin-mediated toxicity. Scientific reports, Apr. 12, 2016, No. 6, Article No. 24242, pp. 1-9.
Protein biosynthesis (translation), Mar. 7, 2025, web archive dated Apr. 3, 2002 [searched on Mar. 7, 2025], https://web.archive.org/web/20020403141548/http://sc.fukuoka-u.ac.jp/~bc1/Biochem/translat.htm.

* cited by examiner

SEQUENCE LISTING

<160> NUMBER OF SEQ ID NOS: 56

<210> SEQ ID NO 1
<211> LENGTH: 8468
<212> TYPE: DNA
<213> ORGANISM: Artificial Sequence
<220> FEATURE:
<223> OTHER INFORMATION: Synthetic Construct - pcDNA3.1-SP-DTA-GS-ccdB

<400> SEQUENCE: 1
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctcg tttagtgaac cgtcagatcg 840
cctggagacg ccatccacgc tgttttgacc tccatagaag acaccgactc tagaggatcc 900
agccatgaag ctctccctgg tggccgcgat gctgctgctg ctcagcgcgg cgcgggccga 960
ggatcctgat gatgttgttg attcttctaa atcttttgtg atggaaaact tttcttcgta 1020
ccacgggact aaacctggtt atgtagattc cattcaaaaa ggtatacaaa agccaaaatc 1080
tggtacacaa ggaaattatg acgatgattg gaaagggttt tatagtaccg acaataaata 1140
cgacgctgcg ggatactctg tagataatga aaacccgctc tctggaaaag ctggaggcgt 1200
ggtcaaagtg acgtatccag gactgacgaa ggttctcgca ctaaaagtgg ataatgccga 1260
aactattaag aaagagttag gtttaagtct cactgaaccg ttgatggagc aagtcggaac 1320
ggaagagttt atcaaaaggt tcggtgatgg tgcttcgcgt gtagtgctca gccttccctt 1380
cgctgagggg agttctagcg ttgaatatat taataactgg gaacaggcga aagcgttaag 1440
cgtagaactt gagattaatt ttgaaacccg tggaaaacgt ggccaagatg cgatgtatga 1500
gtatatggct caagcctgtg caggaaatcg tgtcaggcga tctgtgggca gcagcctgag 1560
ctgcatcaac ctggactggg acgtgatccg cgacaagacc aagaccaaga tcgagagcct 1620
gaaggagcac ggccccatca agaacaagat gagcgagagc cccaacaaga ccgtgagcga 1680
ggagaaggcc aagcagtacc tggaggagtt ccaccagacc gccctggagc accccgagct 1740
gagcgagctg aagaccgtga ccggcaccaa ccccgtgttc gccggcgcca actacgccgc 1800
ctgggccgtg aacgtggccc aggtgatcga cagcgagacc gccgacaacc tggagaagac 1860

```
caccgccgcc ctgagcatcc tgcccggcat cggcagcgtg atgggcatcg ccgacggcgc   1920
cgtgcaccac aacaccgagg agatcgtggc ccagagcatc gccctgagca gcctgatggt   1980
ggcccaggcc atcccccctgg tggcgagct ggtggacatc ggcttcgccg cctacaactt  2040
cgtggagagc atcatcaacc tgttccaggt ggtgcacaac agctacaacc gccccgccta   2100
cagccccggc cacaagacct cgagtggctc gggctcgaca agtttgtaca aaaaagctga   2160
acgagaaacg taaaatgata taaatatcaa tatattaaat tagattttgc ataaaaaaca   2220
gactacataa tactgtaaaa cacaacatat ccagtcacta tggcggccgc attaggcacc   2280
ccaggcttta cactttatgc ttccggctcg tataatgtgt ggattttgag ttaggatccg   2340
gcgagatttt caggagctaa ggaagctaaa atggagaaaa aaatcactgg atataccacc   2400
gttgatatat cccaatggca tcgtaaagaa cattttgagg catttcagtc agttgctcaa   2460
tgtacctata accagaccgt tcagctggat attacggcct ttttaaagac cgtaaagaaa   2520
aataagcaca agttttatcc ggcctttatt cacattcttg cccgcctgat gaatgctcat   2580
ccggaattcc gtatggcaat gaaagacggt gagctggtga tatgggatag tgttcaccct   2640
tgttacaccg ttttccatga gcaaactgaa acgttttcat cgctctggag tgaataccac   2700
gacgatttcc ggcagtttct acacatatat tcgcaagatg tggcgtgtta cggtgaaaac   2760
ctggcctatt tccctaaagg gtttattgag aatatgtttt tcgtctcagc caatccctgg   2820
gtgagtttca ccagttttga tttaaacgtg gccaatatgg acaacttctt cgcccccgtt   2880
ttcaccatgg gcaaatatta tacgcaaggc gacaaggtgc tgatgccgct ggcgattcag   2940
gttcatcatg ccgtctgtga tggcttccat gtcggcagaa tgcttaatga attacaacag   3000
tactgcgatg agtggcaggg cggggcgtaa agatctggat ccggcttact aaaagccaga   3060
taacagtatg cgtatttgcg cgctgatttt tgcggtataa gaatatatac tgatatgtat   3120
acccgaagta tgtcaaaaag aggtatgcta tgaagcagcg tattacagtg acagttgaca   3180
gcgacagcta tcagttgctc aaggcatata tgatgtcaat atctccggtc tggtaagcac   3240
aaccatgcag aatgaagccc gtcgtctgcg tgccgaacgc tggaaagcgg aaaatcagga   3300
agggatggct gaggtcgccc ggtttattga aatgaacggc tcttttgctg acgagaacag   3360
gggctggtga aatgcagttt aaggtttaca cctataaaag agagagccgt tatcgtctgt   3420
ttgtggatgt acagagtgat attattgaca cgcccgggcg acggatggtg atccccctgg   3480
ccagtgcacg tctgctgtca gataaagtct cccgtgaact ttacccggtg gtgcatatcg   3540
gggatgaaag ctggcgcatg atgaccaccg atatggccag tgtgccggtc tccgttatcg   3600
gggaagaagt ggctgatctc agccaccgcg aaaatgacat caaaaacgcc attaacctga   3660
tgttctgggg aatataaatg tcaggctccc ttatacacag ccagtctgca ggtcgaccat   3720
agtgactgga tatgttgtgt tttacagtat tatgtagtct gtttttttatg caaaatctaa   3780
tttaatatat tgatatttat atcattttac gtttctcgtt cagctttctt gtacaaagtg   3840
gttgctctat agtaactcga gtctagaggg cccgtttaaa cccgctgatc agcctcgact   3900
gtgccttcta gttgccagcc atctgttgtt tgcccctccc ccgtgccttc cttgaccctg   3960
gaaggtgcca ctcccactgt cctttcctaa taaaatgagg aaattgcatc gcattgtctg   4020
agtaggtgtc attctattct ggggggtggg gtggggcagg acagcaaggg ggaggattgg   4080
gaagacaata gcaggcatgc tggggatgcg gtgggctcta tggcttctga ggcggaaaga   4140
accagctggg gctctagggg gtatccccac gcgccctgta gcggcgcatt aagcgcggcg   4200
```

```
ggtgtggtgg ttacgcgcag cgtgaccgct acacttgcca gcgccctagc gcccgctcct   4260
ttcgctttct tcccttcctt tctcgccacg ttcgccggct ttccccgtca agctctaaat   4320
cgggggctcc ctttagggtt ccgatttagt gctttacggc acctcgaccc caaaaaactt   4380
gattagggtg atggttcacg tagtgggcca tcgccctgat agacggtttt tcgccctttg   4440
acgttggagt ccacgttctt taatagtgga ctcttgttcc aaactggaac aacactcaac   4500
cctatctcgg tctattcttt tgatttataa gggattttgc cgatttcggc ctattggtta   4560
aaaaatgagc tgatttaaca aaaatttaac gcgaattaat tctgtggaat gtgtgtcagt   4620
tagggtgtgg aaagtcccca ggctccccag caggcagaag tatgcaaagc atgcatctca   4680
attagtcagc aaccaggtgt ggaaagtccc caggctcccc agcaggcaga agtatgcaaa   4740
gcatgcatct caattagtca gcaaccatag tcccgcccct aactccgccc atcccgcccc   4800
taactccgcc cagttccgcc cattctccgc cccatggctg actaattttt tttatttatg   4860
cagaggccga ggccgcctct gcctctgagc tattccagaa gtagtgagga ggcttttttg   4920
gaggcctagg cttttgcaaa aagctcccgg gagcttgtat atccattttc ggatctgatc   4980
agcacgtgat gaaaaagcct gaactcaccg cgacgtctgt cgagaagttt ctgatcgaaa   5040
agttcgacag cgtctccgac ctgatgcagc tctcggaggg cgaagaatct cgtgctttca   5100
gcttcgatgt aggagggcgt ggatatgtcc tgcgggtaaa tagctgcgcc gatggtttct   5160
acaaagatcg ttatgtttat cggcactttg catcggccgc gctcccgatt ccggaagtgc   5220
ttgacattgg ggaattcagc gagagcctga cctattgcat ctcccgccgt gcacagggtg   5280
tcacgttgca agacctgcct gaaaccgaac tgcccgctgt tctgcagccg gtcgcggagg   5340
ccatggatgc gatcgctgcg gccgatctta gccagacgag cgggttcggc ccattcggac   5400
cgcaaggaat cggtcaatac actacatggc gtgatttcat atgcgcgatt gctgatcccc   5460
atgtgtatca ctggcaaact gtgatggacg acaccgtcag tgcgtccgtc gcgcaggctc   5520
tcgatgagct gatgctttgg gccgaggact gccccgaagt ccggcacctc gtgcacgcgg   5580
atttcggctc caacaatgtc ctgacggaca atggccgcat aacagcggtc attgactgga   5640
gcgaggcgat gttcggggat tcccaatacg aggtcgccaa catcttcttc tggaggccgt   5700
ggttggcttg tatggagcag cagacgcgct acttcgagcg gaggcatccg gagcttgcag   5760
gatcgccgcg gctccgggcg tatatgctcc gcattggtct tgaccaactc tatcagagct   5820
tggttgacgg caatttcgat gatgcagctt gggcgcaggg tcgatgcgac gcaatcgtcc   5880
gatccggagc cgggactgtc gggcgtacac aaatcgcccg cagaagcgcg gccgtctgga   5940
ccgatggctg tgtagaagta ctcgccgata gtggaaaccg acgccccagc actcgtccga   6000
gggcaaagga atagcacgtg ctacgagatt tcgattccac cgccgccttc tatgaaaggt   6060
tgggcttcgg aatcgttttc cgggacgccg gctggatgat cctccagcgc ggggatctca   6120
tgctggagtt cttcgcccac cccaacttgt ttattgcagc ttataatggt tacaaataaa   6180
gcaatagcat cacaaatttc acaaataaag catttttttc actgcattct agttgtggtt   6240
tgtccaaact catcaatgta tcttatcatg tctgtatacc gtcgacctct agctagagct   6300
tggcgtaatc atggtcatag ctgtttcctg tgtgaaattg ttatccgctc acaattccac   6360
acaacatacg agccggaagc ataaagtgta aagcctgggg tgcctaatga gtgagctaac   6420
tcacattaat tgcgttgcgc tcactgcccg ctttccagtc gggaaacctg tcgtgccagc   6480
tgcattaatg aatcggccaa cgcgcgggga gaggcggttt gcgtattggg cgctcttccg   6540
cttcctcgct cactgactcg ctgcgctcgg tcgttcggct gcggcgagcg gtatcagctc   6600
```

actcaaaggc ggtaatacgg ttatccacag aatcagggga taacgcagga aagaacatgt 6660
gagcaaaagg ccagcaaaag gccaggaacc gtaaaaaggc cgcgttgctg gcgtttttcc 6720
ataggctccg cccccctgac gagcatcaca aaaatcgacg ctcaagtcag aggtggcgaa 6780
acccgacagg actataaaga taccaggcgt ttccccctgg aagctccctc gtgcgctctc 6840
ctgttccgac cctgccgctt accggatacc tgtccgcctt tctcccttcg ggaagcgtgg 6900
cgctttctca tagctcacgc tgtaggtatc tcagttcggt gtaggtcgtt cgctccaagc 6960
tgggctgtgt gcacgaaccc cccgttcagc ccgaccgctg cgccttatcc ggtaactatc 7020
gtcttgagtc caacccggta agacacgact tatcgccact ggcagcagcc actggtaaca 7080
ggattagcag agcgaggtat gtaggcggtg ctacagagtt cttgaagtgg tggcctaact 7140
acggctacac tagaagaaca gtatttggta tctgcgctct gctgaagcca gttaccttcg 7200
gaaaaagagt tggtagctct tgatccggca aacaaaccac cgctggtagc ggtttttttg 7260
tttgcaagca gcagattacg cgcagaaaaa aaggatctca agaagatcct ttgatctttt 7320
ctacggggtc tgacgctcag tggaacgaaa actcacgtta agggattttg gtcatgagat 7380
tatcaaaaag gatcttcacc tagatccttt taaattaaaa atgaagtttt aaatcaatct 7440
aaagtatata tgagtaaact tggtctgaca gttaccaatg cttaatcagt gaggcaccta 7500
tctcagcgat ctgtctattt cgttcatcca tagttgcctg actccccgtc gtgtagataa 7560
ctacgatacg ggagggctta ccatctggcc ccagtgctgc aatgataccg cgagacccac 7620
gctcaccggc tccagattta tcagcaataa accagccagc cggaagggcc gagcgcagaa 7680
gtggtcctgc aactttatcc gcctccatcc agtctattaa ttgttgccgg gaagctagag 7740
taagtagttc gccagttaat agtttgcgca acgttgttgc cattgctaca ggcatcgtgg 7800
tgtcacgctc gtcgtttggt atggcttcat tcagctccgg ttcccaacga tcaaggcgag 7860
ttacatgatc ccccatgttg tgcaaaaaag cggttagctc cttcggtcct ccgatcgttg 7920
tcagaagtaa gttggccgca gtgttatcac tcatggttat ggcagcactg cataattctc 7980
ttactgtcat gccatccgta agatgctttt ctgtgactgg tgagtactca accaagtcat 8040
tctgagaata gtgtatgcgg cgaccgagtt gctcttgccc ggcgtcaata cgggataata 8100
ccgcgccaca tagcagaact ttaaaagtgc tcatcattgg aaaacgttct tcggggcgaa 8160
aactctcaag gatcttaccg ctgttgagat ccagttcgat gtaacccact cgtgcaccca 8220
actgatcttc agcatctttt actttcacca gcgtttctgg gtgagcaaaa acaggaaggc 8280
aaaatgccgc aaaaaaggga ataagggcga cacggaaatg ttgaatactc atactcttcc 8340
tttttcaata ttattgaagc atttatcagg gttattgtct catgagcgga tacatatttg 8400
aatgtattta gaaaaataaa caaatagggg ttccgcgcac atttccccga aaagtgccac 8460
ctgacgtc 8468

<210> SEQ ID NO 2
<211> LENGTH: 8899
<212> TYPE: DNA
<213> ORGANISM: Artificial Sequence
<220> FEATURE:
<223> OTHER INFORMATION: Synthetic Construct - pET15b-SHT-SUMO-DTA-ccdB

<400> SEQUENCE: 2
ttcttgaaga cgaaagggcc tcgtgatacg cctattttta taggttaatg tcatgataat 60
aatggtttct tagacgtcag gtggcacttt tcggggaaat gtgcgcggaa cccctatttg 120

```
tttatttttc taaatacatt caaatatgta tccgctcatg agacaataac cctgataaat    180
gcttcaataa tattgaaaaa ggaagagtat gagtattcaa catttccgtg tcgcccttat    240
tccctttttt gcggcatttt gccttcctgt ttttgctcac ccagaaacgc tggtgaaagt    300
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga caacgatcgg aggaccgaag gagctaaccg cttttttgca    660
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc ctttttgata atctcatgac caaaatccct taacgtgagt tttcgttcca   1200
ctgagcgtca gaccccgtag aaaagatcaa aggatcttct tgagatcctt tttttctgcg   1260
cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
```

cgatacgggt tactgatgat gaacatgccc ggttactgga acgttgtgag ggtaaacaac 2580
tggcggtatg gatgcggcgg gaccagagaa aaatcactca gggtcaatgc cagcgcttcg 2640
ttaatacaga tgtaggtgtt ccacagggta gccagcagca tcctgcgatg cagatccgga 2700
acataatggt gcagggcgct gacttccgcg tttccagact ttacgaaaca cggaaaccga 2760
agaccattca tgttgttgct caggtcgcag acgttttgca gcagcagtcg cttcacgttc 2820
gctcgcgtat cggtgattca ttctgctaac cagtaaggca accccgccag cctagccggg 2880
tcctcaacga caggagcacg atcatgcgca cccgtggcca ggacccaacg ctgcccgaga 2940
tgcgccgcgt gcggctgctg gagatggcgg acgcgatgga tatgttctgc caagggttgg 3000
tttgcgcatt cacagttctc cgcaagaatt gattggctcc aattcttgga gtggtgaatc 3060
cgttagcgag gtgccgccgg cttccattca ggtcgaggtg gcccggctcc atgcaccgcg 3120
acgcaacgcg gggaggcaga caaggtatag ggcggcgcct acaatccatg ccaacccgtt 3180
ccatgtgctc gccgaggcgg cataaatcgc cgtgacgatc agcggtccag tgatcgaagt 3240
taggctggta agagccgcga gcgatccttg aagctgtccc tgatggtcgt catctacctg 3300
cctggacagc atggcctgca acgcgggcat cccgatgccg ccggaagcga gaagaatcat 3360
aatggggaag gccatccagc ctcgcgtcgc gaacgccagc aagacgtagc ccagcgcgtc 3420
ggccgccatg ccggcgataa tggcctgctt ctcgccgaaa cgtttggtgg cgggaccagt 3480
gacgaaggct tgagcgaggg cgtgcaagat tccgaatacc gcaagcgaca ggccgatcat 3540
cgtcgcgctc cagcgaaagc ggtcctcgcc gaaaatgacc cagagcgctg ccggcacctg 3600
tcctacgagt tgcatgataa agaagacagt cataagtgcg gcgacgatag tcatgccccg 3660
cgcccaccgg aaggagctga ctgggttgaa ggctctcaag ggcatcggtc gagatcccgg 3720
tgcctaatga gtgagctaac ttacattaat tgcgttgcgc tcactgcccg ctttccagtc 3780
gggaaacctg tcgtgccagc tgcattaatg aatcggccaa cgcgcgggga gaggcggttt 3840
gcgtattggg cgccagggtg gtttttcttt tcaccagtga gacgggcaac agctgattgc 3900
ccttcaccgc ctggccctga gagagttgca gcaagcggtc cacgctggtt tgccccagca 3960
ggcgaaaatc ctgtttgatg gtggttaacg gcgggatata acatgagctg tcttcggtat 4020
cgtcgtatcc cactaccgag atatccgcac caacgcgcag cccggactcg gtaatggcgc 4080
gcattgcgcc cagcgccatc tgatcgttgg caaccagcat cgcagtggga acgatgccct 4140
cattcagcat ttgcatggtt tgttgaaaac cggacatggc actccagtcg ccttcccgtt 4200
ccgctatcgg ctgaatttga ttgcgagtga gatatttatg ccagccagcc agacgcagac 4260
gcgccgagac agaacttaat gggcccgcta acagcgcgat ttgctggtga cccaatgcga 4320
ccagatgctc cacgcccagt cgcgtaccgt cttcatggga gaaaataata ctgttgatgg 4380
gtgtctggtc agagacatca agaaataacg ccggaacatt agtgcaggca gcttccacag 4440
caatggcatc ctggtcatcc agcggatagt taatgatcag cccactgacg cgttgcgcga 4500
gaagattgtg caccgccgct ttacaggctt cgacgccgct tcgttctacc atcgacacca 4560
ccacgctggc acccagttga tcggcgcgag atttaatcgc cgcgacaatt tgcgacggcg 4620
cgtgcagggc cagactggag gtggcaacgc caatcagcaa cgactgtttg cccgccagtt 4680
gttgtgccac gcggttggga atgtaattca gctccgccat cgccgcttcc actttttccc 4740
gcgttttcgc agaaacgtgg ctggcctggt tcaccacgcg ggaaacggtc tgataagaga 4800
caccggcata ctctgcgaca tcgtataacg ttactggttt cacattcacc accctgaatt 4860

-continued gactctcttc cgggcgctat catgccatac cgcgaaaggt tttgcgccat tcgatggtgt 4920
ccgggatctc gacgctctcc cttatgcgac tcctgcatta ggaagcagcc cagtagtagg 4980
ttgaggccgt tgagcaccgc cgccgcaagg aatggtgcat gcaaggagat ggcgcccaac 5040
agtcccccgg ccacggggcc tgccaccata cccacgccga aacaagcgct catgagcccg 5100
aagtggcgag cccgatcttc cccatcggtg atgtcggcga tataggcgcc agcaaccgca 5160
cctgtggcgc cggtgatgcc ggccacgatg cgtccggcgt agaggatcga gatctcgatc 5220
ccgcgaaatt aatacgactc actatagggg aattgtgagc ggataacaat tcccctctag 5280
aaataatttt gtttaacttt aagaaggaga tataccatgt ggtcccatcc tcaattcgag 5340
aagcatcacc atcaccatca ccatcacgga tctgaaaatc tctacttcca gcatatgtcg 5400
gactcagaag tcaatcaaga agctaagcca gaggtcaagc cagaagtcaa gcctgagact 5460
cacatcaatt taaaggtgtc cgatggatct tcagagatct tcttcaagat caaaaagacc 5520
actcctttaa gaaggctgat ggaagcgttc gctaaaagac agggtaagga aatggactcc 5580
ttaagattct tgtacgacgg tattagaatt caagctgatc agacccctga agatttggac 5640
atggaggata acgatattat tgaggctcac agagaacaga ttggtggtgg cgctgatgat 5700
gttgttgatt cttctaaatc ttttgtgatg gaaaactttt cttcgtacca cgggactaaa 5760
cctggttatg tagattccat tcaaaaaggt atacaaaagc caaaatctgg tacacaagga 5820
aattatgacg atgattggaa agggttttat agtaccgaca ataaatacga cgctgcggga 5880
tactctgtag ataatgaaaa cccgctctct ggaaaagctg gaggcgtggt caaagtgacg 5940
tatccaggac tgacgaaggt tctcgcacta aaagtggata atgccgaaac tattaagaaa 6000
gagttaggtt taagtctcac tgaaccgttg atggagcaag tcggaacgga agagtttatc 6060
aaaaggttcg gtgatggtgc ttcgcgtgta gtgctcagcc ttcccttcgc tgaggggagt 6120
tctagcgttg aatatattaa taactgggaa caggcgaaag cgttaagcgt agaacttgag 6180
attaattttg aaacccgtgg aaaacgtggc caagatgcga tgtatgagta tatggctcaa 6240
gcctgtgcag gaaatcgtgt caggcgatca gtaggtagct cattgtcatg cataaatctt 6300
gattgggatg tcataaggga taaaactaag acaaagatag agtctttgaa agagcatggc 6360
cctatcaaaa ataaaatgag cgaaagtccc aataaaacag tatctgagga aaaagctaaa 6420
caatacctag aagaatttca tcaaacggca ttagagcatc ctgaattgtc agaacttaaa 6480
accgttactg ggaccaatcc tgtattcgct ggggctaact atgcggcgtg ggcagtaaac 6540
gttgcgcaag ttatcgatag cgaaacagct gataatttgg aaaagacaac tgctgctctt 6600
tcgatacttc ctggtatcgg tagcgtaatg ggcattgcag acggtgccgt tcaccacaat 6660
acagaagaga tagtggcaca atcaatagct ttatcgtctt taatggttgc tcaagctatt 6720
ccattggtag gagagctagt tgatattggt ttcgctgcat ataattttgt agagagtatt 6780
atcaatttat ttcaagtagt tcataattcg tataatcgtc ccgcgtattc tccggggcat 6840
aaaacgacaa gtttgtacaa aaaagctgaa cgagaaacgt aaaatgatat aaatatcaat 6900
atattaaatt agattttgca taaaaaacag actacataat actgtaaaac acaacatatc 6960
cagtcactat ggcggccgca ttaggcaccc caggctttac actttatgct tccggctcgt 7020
ataatgtgtg gattttgagt taggatccgt cgagattttc aggagctaag gaagctaaaa 7080
tggagaaaaa aatcactgga tataccaccg ttgatatatc ccaatggcat cgtaaagaac 7140
attttgaggc atttcagtca gttgctcaat gtacctataa ccagaccgtt cagctggata 7200
ttacggcctt tttaaagacc gtaaagaaaa ataagcacaa gttttatccg gcctttattc 7260
acattcttgc ccgcctgatg aatgctcatc cggaattccg tatggcaatg aaagacggtg 7320
agctggtgat atgggatagt gttcaccctt gttacaccgt tttccatgag caaactgaaa 7380
cgttttcatc gctctggagt gaataccacg acgatttccg gcagtttcta cacatatatt 7440
cgcaagatgt ggcgtgttac ggtgaaaacc tggcctattt ccctaaaggg tttattgaga 7500
atatgttttt cgtctcagcc aatccctggg tgagtttcac cagttttgat ttaaacgtgg 7560
ccaatatgga caacttcttc gcccccgttt tcaccatggg caaatattat acgcaaggcg 7620
acaaggtgct gatgccgctg gcgattcagg ttcatcatgc cgtttgtgat ggcttccatg 7680
tcggcagaat gcttaatgaa ttacaacagt actgcgatga gtggcagggc ggggcgtaaa 7740
gatctggatc cggcttacta aaagccagat aacagtatgc gtatttgcgc gctgattttt 7800
gcggtataag aatatatact gatatgtata cccgaagtat gtcaaaaaga ggtatgctat 7860
gaagcagcgt attacagtga cagttgacag cgacagctat cagttgctca aggcatatat 7920
gatgtcaata tctccggtct ggtaagcaca accatgcaga atgaagcccg tcgtctgcgt 7980
gccgaacgct ggaaagcgga aaatcaggaa gggatggctg aggtcgcccg gtttattgaa 8040
atgaacggct cttttgctga cgagaacagg ggctggtgaa atgcagttta aggtttacac 8100
ctataaaaga gagagccgtt atcgtctgtt tgtggatgta cagagtgata ttattgacac 8160
gcccgggcga cggatggtga tccccctggc cagtgcacgt ctgctgtcag ataaagtctc 8220
ccgtgaactt tacccggtgg tgcatatcgg ggatgaaagc tggcgcatga tgaccaccga 8280
tatggccagt gtgccggtct ccgttatcgg ggaagaagtg gctgatctca gccaccgcga 8340
aaatgacatc aaaaacgcca ttaacctgat gttctgggga atataaatgt caggctccct 8400
tatacacagc cagtctgcag gtcgaccata gtgactggat atgttgtgtt ttacagtatt 8460
atgtagtctg tttttatgc aaaatctaat ttaatatatt gatatttata tcattttacg 8520
tttctcgttc agctttcttg tacaaagtgg tgtaggctag cggtaccggc cggccggatc 8580
cggctgctaa caaagcccga aaggaagctg agttggctgc tgccaccgct gagcaataac 8640
tagcataacc ccttggggcc tctaaacggg tcttgagggg ttttttgctg aaaggaggaa 8700
ctatatccgg atatcccgca agaggcccgg cagtaccggc ataaccaagc ctatgcctac 8760
agcatccagg gtgacggtgc cgaggatgac gatgagcgca ttgttagatt tcatacacgg 8820
tgcctgactg cgttagcaat ttaactgtga taaactaccg cattaaagct tatcgatgat 8880
aagctgtcaa acatgagaa 8899

<210> SEQ ID NO 3
<211> LENGTH: 8490
<212> TYPE: DNA
<213> ORGANISM: Artificial Sequence
<220> FEATURE:
<223> OTHER INFORMATION: Synthetic Construct - pcDNA3.1-SP-codB-GSlinker-PE40

<400> SEQUENCE: 3
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360

```
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattctga    960
tggagacaga cacactcctg ctatgggtac tgctgctctg ggttccaggt tccactggtg   1020
acgcggccac aagtttgtac aaaaaagctg aacgagaaac gtaaaatgat ataaatatca   1080
atatattaaa ttagattttg cataaaaaac agactacata atactgtaaa acacaacata   1140
tccagtcact atggcggccg cattaggcac cccaggcttt acactttatg cttccggctc   1200
gtataatgtg tggattttga gttaggatcc gtcgagattt tcaggagcta aggaagctaa   1260
aatggagaaa aaaatcactg gatataccac cgttgatata tcccaatggc atcgtaaaga   1320
acattttgag gcatttcagt cagttgctca atgtacctat aaccagaccg ttcagctgga   1380
tattacggcc tttttaaaga ccgtaaagaa aaataagcac aagttttatc cggcctttat   1440
tcacattctt gcccgcctga tgaatgctca tccggaattc cgtatggcaa tgaaagacgg   1500
tgagctggtg atatgggata gtgttcaccc ttgttacacc gttttccatg agcaaactga   1560
aacgttttca tcgctctgga gtgaatacca cgacgatttc cggcagtttc tacacatata   1620
ttcgcaagat gtggcgtgtt acggtgaaaa cctggcctat ttccctaaag ggtttattga   1680
gaatatgttt ttcgtctcag ccaatccctg ggtgagtttc accagttttg atttaaacgt   1740
ggccaatatg gacaacttct tcgcccccgt tttcaccatg ggcaaatatt atacgcaagg   1800
cgacaaggtg ctgatgccgc tggcgattca ggttcatcat gccgtttgtg atggcttcca   1860
tgtcggcaga atgcttaatg aattacaaca gtactgcgat gagtggcagg gcggggcgta   1920
aagatctgga tccggcttac taaaagccag ataacagtat gcgtatttgc gcgctgattt   1980
ttgcggtata agaatatata ctgatatgta tacccgaagt atgtcaaaaa gaggtatgct   2040
atgaagcagc gtattacagt gacagttgac agcgacagct atcagttgct caaggcatat   2100
atgatgtcaa tatctccggt ctggtaagca caaccatgca gaatgaagcc cgtcgtctgc   2160
gtgccgaacg ctggaaagcg gaaaatcagg aagggatggc tgaggtcgcc cggtttattg   2220
aaatgaacgg ctcttttgct gacgagaaca ggggctggtg aaatgcagtt taaggtttac   2280
acctataaaa gagagagccg ttatcgtctg tttgtggatg tacagagtga tattattgac   2340
acgcccgggc gacggatggt gatccccctg gccagtgcac gtctgctgtc agataaagtc   2400
tcccgtgaac tttacccggt ggtgcatatc ggggatgaaa gctggcgcat gatgaccacc   2460
gatatggcca gtgtgccggt ctccgttatc ggggaagaag tggctgatct cagccaccgc   2520
gaaaatgaca tcaaaaacgc cattaacctg atgttctggg gaatataaat gtcaggctcc   2580
cttatacaca gccagtctgc aggtcgacca tagtgactgg atatgttgtg ttttacagta   2640
ttatgtagtc tgttttttat gcaaaatcta atttaatata ttgatattta tatcatttta   2700
```

cgtttctcgt tcagctttct tgtacaaagt ggttgatatc cagcacagtg gcggccgctc 2760
gagtggctcg ggctcgacct cgggctcggg caaaaccggt gagggcggca gcctggccgc 2820
gctgaccgcg caccaggctt gccacctgcc gctggagact ttcacccgtc atcgccagcc 2880
gcgcggctgg gaacaactgg agcagtgcgg ctatccggtg cagcggctgg tcgccctcta 2940
cctggcggcg cggctgtcgt ggaaccaggt cgaccaggtg atccgcaacg ccctggccag 3000
ccccggcagc ggcggcgacc tgggcgaagc gatccgcgag cagccggagc aggcccgtct 3060
ggccctgacc ctggccgccg ccgagagcga gcgcttcgtc cggcagggca ccggcaacga 3120
cgaggccggc gcggccaacg ccgacgtggt gagcctgacc tgcccggtcg ccgccggtga 3180
atgcgcgggc ccggcggaca gcggcgacgc cctgctggag cgcaactatc ccactggcgc 3240
ggagttcctc ggcgacggcg gcgacgtcag cttcagcacc cgcggcacgc agaactggac 3300
ggtggagcgg ctgctccagg cgcaccgcca actggaggag cgcggctatg tgttcgtcgg 3360
ctaccacggc accttcctcg aagcggcgca aagcatcgtc ttcggcgggg tgcgcgcgcg 3420
cagccaggac ctcgacgcga tctggcgcgg tttctatatc gccggcgatc cggcgctggc 3480
ctacggctac gcccaggacc aggaacccga cgcacgcggc cggatccgca acggtgccct 3540
gctgcgggtc tatgtgccgc gctcgagcct gccgggcttc taccgcacca gcctgaccct 3600
ggccgcgccg gaggcggcgg gcgaggtcga acggctgatc ggccatccgc tgccgctgcg 3660
cctggacgcc atcaccggcc ccgaggagga aggcgggcgc ctggagacca ttctcggctg 3720
gccgctggcc gagcgcaccg tggtgattcc ctcggcgatc cccaccgacc cgcgcaacgt 3780
cggcggcgac ctcgacccgt ccagcatccc cgacaaggaa caggcgatca gcgccctgcc 3840
ggactacgcc agccagcccg gcaaaccgcc gcgcgaggac ctgaagtaag ggcccgttta 3900
aacccgctga tcagcctcga ctgtgccttc tagttgccag ccatctgttg tttgcccctc 3960
ccccgtgcct tccttgaccc tggaaggtgc cactcccact gtcctttcct aataaaatga 4020
ggaaattgca tcgcattgtc tgagtaggtg tcattctatt ctggggggtg gggtggggca 4080
ggacagcaag ggggaggatt gggaagacaa tagcaggcat gctggggatg cggtgggctc 4140
tatggcttct gaggcggaaa gaaccagctg gggctctagg gggtatcccc acgcgccctg 4200
tagcggcgca ttaagcgcgg cgggtgtggt ggttacgcgc agcgtgaccg ctacacttgc 4260
cagcgcccta gcgcccgctc ctttcgcttt cttcccttcc tttctcgcca cgttcgccgg 4320
ctttccccgt caagctctaa atcgggggct ccctttaggg ttccgattta gtgctttacg 4380
gcacctcgac cccaaaaaac ttgattaggg tgatggttca cgtagtgggc catcgccctg 4440
atagacggtt tttcgccctt tgacgttgga gtccacgttc tttaatagtg gactcttgtt 4500
ccaaactgga acaacactca accctatctc ggtctattct tttgatttat aagggatttt 4560
gccgatttcg gcctattggt taaaaaatga gctgatttaa caaaaattta acgcgaatta 4620
attctgtgga atgtgtgtca gttagggtgt ggaaagtccc caggctcccc agcaggcaga 4680
agtatgcaaa gcatgcatct caattagtca gcaaccaggt gtggaaagtc cccaggctcc 4740
ccagcaggca gaagtatgca aagcatgcat ctcaattagt cagcaaccat agtcccgccc 4800
ctaactccgc ccatcccgcc cctaactccg cccagttccg cccattctcc gccccatggc 4860
tgactaattt tttttattta tgcagaggcc gaggccgcct ctgcctctga gctattccag 4920
aagtagtgag gaggcttttt tggaggccta ggcttttgca aaaagctccc gggagcttgt 4980
atatccattt tcggatctga tcagcacgtg atgaaaaagc ctgaactcac cgcgacgtct 5040
gtcgagaagt ttctgatcga aaagttcgac agcgtctccg acctgatgca gctctcggag 5100

```
ggcgaagaat ctcgtgcttt cagcttcgat gtaggagggc gtggatatgt cctgcgggta   5160
aatagctgcg ccgatggttt ctacaaagat cgttatgttt atcggcactt tgcatcggcc   5220
gcgctcccga ttccggaagt gcttgacatt ggggaattca gcgagagcct gacctattgc   5280
atctcccgcc gtgcacaggg tgtcacgttg caagacctgc ctgaaaccga actgcccgct   5340
gttctgcagc cggtcgcgga ggccatggat gcgatcgctg cggccgatct tagccagacg   5400
agcgggttcg gcccattcgg accgcaagga atcggtcaat acactacatg gcgtgatttc   5460
atatgcgcga ttgctgatcc ccatgtgtat cactggcaaa ctgtgatgga cgacaccgtc   5520
agtgcgtccg tcgcgcaggc tctcgatgag ctgatgcttt gggccgagga ctgccccgaa   5580
gtccggcacc tcgtgcacgc ggatttcggc tccaacaatg tcctgacgga caatggccgc   5640
ataacagcgg tcattgactg gagcgaggcg atgttcgggg attcccaata cgaggtcgcc   5700
aacatcttct tctggaggcc gtggttggct tgtatggagc agcagacgcg ctacttcgag   5760
cggaggcatc cggagcttgc aggatcgccg cggctccggg cgtatatgct ccgcattggt   5820
cttgaccaac tctatcagag cttggttgac ggcaatttcg atgatgcagc ttgggcgcag   5880
ggtcgatgcg acgcaatcgt ccgatccgga gccgggactg tcgggcgtac acaaatcgcc   5940
cgcagaagcg cggccgtctg gaccgatggc tgtgtagaag tactcgccga tagtggaaac   6000
cgacgcccca gcactcgtcc gagggcaaag gaatagcacg tgctacgaga tttcgattcc   6060
accgccgcct tctatgaaag gttgggcttc ggaatcgttt tccgggacgc cggctggatg   6120
atcctccagc gcggggatct catgctggag ttcttcgccc accccaactt gtttattgca   6180
gcttataatg gttacaaata aagcaatagc atcacaaatt tcacaaataa agcatttttt   6240
tcactgcatt ctagttgtgg tttgtccaaa ctcatcaatg tatcttatca tgtctgtata   6300
ccgtcgacct ctagctagag cttggcgtaa tcatggtcat agctgtttcc tgtgtgaaat   6360
tgttatccgc tcacaattcc acacaacata cgagccggaa gcataaagtg taaagcctgg   6420
ggtgcctaat gagtgagcta actcacatta attgcgttgc gctcactgcc cgctttccag   6480
tcgggaaacc tgtcgtgcca gctgcattaa tgaatcggcc aacgcgcggg gagaggcggt   6540
ttgcgtattg ggcgctcttc cgcttcctcg ctcactgact cgctgcgctc ggtcgttcgg   6600
ctgcggcgag cggtatcagc tcactcaaag gcggtaatac ggttatccac agaatcaggg   6660
gataacgcag gaaagaacat gtgagcaaaa ggccagcaaa aggccaggaa ccgtaaaaag   6720
gccgcgttgc tggcgttttt ccataggctc cgcccccctg acgagcatca caaaaatcga   6780
cgctcaagtc agaggtggcg aaacccgaca ggactataaa gataccaggc gtttccccct   6840
ggaagctccc tcgtgcgctc tcctgttccg accctgccgc ttaccggata cctgtccgcc   6900
tttctccctt cgggaagcgt ggcgctttct catagctcac gctgtaggta tctcagttcg   6960
gtgtaggtcg ttcgctccaa gctgggctgt gtgcacgaac cccccgttca gcccgaccgc   7020
tgcgccttat ccggtaacta tcgtcttgag tccaacccgg taagacacga cttatcgcca   7080
ctggcagcag ccactggtaa caggattagc agagcgaggt atgtaggcgg tgctacagag   7140
ttcttgaagt ggtggcctaa ctacggctac actagaagaa cagtatttgg tatctgcgct   7200
ctgctgaagc cagttacctt cggaaaaaga gttggtagct cttgatccgg caaacaaacc   7260
accgctggta gcggtttttt tgtttgcaag cagcagatta cgcgcagaaa aaaaggatct   7320
caagaagatc ctttgatctt ttctacgggg tctgacgctc agtggaacga aaactcacgt   7380
taagggattt tggtcatgag attatcaaaa aggatcttca cctagatcct tttaaattaa   7440
```

aaatgaagtt ttaaatcaat ctaaagtata tatgagtaaa cttggtctga cagttaccaa 7500
tgcttaatca gtgaggcacc tatctcagcg atctgtctat ttcgttcatc catagttgcc 7560
tgactccccg tcgtgtagat aactacgata cgggagggct taccatctgg ccccagtgct 7620
gcaatgatac cgcgagaccc acgctcaccg gctccagatt tatcagcaat aaaccagcca 7680
gccggaaggg ccgagcgcag aagtggtcct gcaactttat ccgcctccat ccagtctatt 7740
aattgttgcc gggaagctag agtaagtagt tcgccagtta atagtttgcg caacgttgtt 7800
gccattgcta caggcatcgt ggtgtcacgc tcgtcgtttg gtatggcttc attcagctcc 7860
ggttcccaac gatcaaggcg agttacatga tcccccatgt tgtgcaaaaa agcggttagc 7920
tccttcggtc ctccgatcgt tgtcagaagt aagttggccg cagtgttatc actcatggtt 7980
atggcagcac tgcataattc tcttactgtc atgccatccg taagatgctt ttctgtgact 8040
ggtgagtact caaccaagtc attctgagaa tagtgtatgc ggcgaccgag ttgctcttgc 8100
ccggcgtcaa tacgggataa taccgcgcca catagcagaa ctttaaaagt gctcatcatt 8160
ggaaaacgtt cttcggggcg aaaactctca aggatcttac cgctgttgag atccagttcg 8220
atgtaaccca ctcgtgcacc caactgatct tcagcatctt ttactttcac cagcgtttct 8280
gggtgagcaa aaacaggaag gcaaaatgcc gcaaaaaagg gaataagggc gacacggaaa 8340
tgttgaatac tcatactctt cctttttcaa tattattgaa gcatttatca gggttattgt 8400
ctcatgagcg gatacatatt tgaatgtatt tagaaaaata aacaaatagg ggttccgcgc 8460
acatttcccc gaaaagtgcc acctgacgtc 8490

<210> SEQ ID NO 4
<211> LENGTH: 5612
<212> TYPE: DNA
<213> ORGANISM: Artificial Sequence
<220> FEATURE:
<223> OTHER INFORMATION: Synthetic Construct - pET15b-SHT-ccd-PE40

<400> SEQUENCE: 4
ttcttgaaga cgaaagggcc tcgtgatacg cctattttta taggttaatg tcatgataat 60
aatggtttct tagacgtcag gtggcacttt tcggggaaat gtgcgcggaa cccctatttg 120
tttatttttc taaatacatt caaatatgta tccgctcatg agacaataac cctgataaat 180
gcttcaataa tattgaaaaa ggaagagtat gagtattcaa catttccgtg tcgcccttat 240
tccctttttt gcggcatttt gccttcctgt ttttgctcac ccagaaacgc tggtgaaagt 300
aaaagatgct gaagatcagt tgggtgcacg agtgggttac atcgaactgg atctcaacag 360
cggtaagatc cttgagagtt ttcgccccga agaacgtttt ccaatgatga gcacttttaa 420
agttctgcta tgtggcgcgg tattatcccg tgttgacgcc gggcaagagc aactcggtcg 480
ccgcatacac tattctcaga atgacttggt tgagtactca ccagtcacag aaaagcatct 540
tacggatggc atgacagtaa gagaattatg cagtgctgcc ataaccatga gtgataacac 600
tgcggccaac ttacttctga caacgatcgg aggaccgaag gagctaaccg cttttttgca 660
caacatgggg gatcatgtaa ctcgccttga tcgttgggaa ccggagctga atgaagccat 720
accaaacgac gagcgtgaca ccacgatgcc tgcagcaatg gcaacaacgt tgcgcaaact 780
attaactggc gaactactta ctctagcttc ccggcaacaa ttaatagact ggatggaggc 840
ggataaagtt gcaggaccac ttctgcgctc ggcccttccg gctggctggt ttattgctga 900
taaatctgga gccggtgagc gtgggtctcg cggtatcatt gcagcactgg ggccagatgg 960
taagccctcc cgtatcgtag ttatctacac gacggggagt caggcaacta tggatgaacg 1020

```
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc ctttttgata atctcatgac caaaatccct taacgtgagt tttcgttcca   1200
ctgagcgtca gaccccgtag aaaagatcaa aggatcttct tgagatcctt tttttctgcg   1260
cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg tttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tgcgccgcgt gcggctgctg gagatggcgg acgcgatgga tatgttctgc caagggttgg   3000
tttgcgcatt cacagttctc cgcaagaatt gattggctcc aattcttgga gtggtgaatc   3060
cgttagcgag gtgccgccgg cttccattca ggtcgaggtg gcccggctcc atgcaccgcg   3120
acgcaacgcg gggaggcaga caaggtatag ggcggcgcct acaatccatg ccaacccgtt   3180
ccatgtgctc gccgaggcgg cataaatcgc cgtgacgatc agcggtccag tgatcgaagt   3240
taggctggta agagccgcga gcgatccttg aagctgtccc tgatggtcgt catctacctg   3300
cctggacagc atggcctgca acgcgggcat cccgatgccg ccggaagcga gaagaatcat   3360
```

```
aatggggaag gccatccagc ctcgcgtcgc gaacgccagc aagacgtagc ccagcgcgtc   3420
ggccgccatg ccggcgataa tggcctgctt ctcgccgaaa cgtttggtgg cgggaccagt   3480
gacgaaggct tgagcgaggg cgtgcaagat tccgaatacc gcaagcgaca ggccgatcat   3540
cgtcgcgctc cagcgaaagc ggtcctcgcc gaaaatgacc cagagcgctg ccggcacctg   3600
tcctacgagt tgcatgataa agaagacagt cataagtgcg gcgacgatag tcatgccccg   3660
cgcccaccgg aaggagctga ctgggttgaa ggctctcaag ggcatcggtc gagatcccgg   3720
tgcctaatga gtgagctaac ttacattaat tgcgttgcgc tcactgcccg ctttccagtc   3780
gggaaacctg tcgtgccagc tgcattaatg aatcggccaa cgcgcgggga gaggcggttt   3840
gcgtattggg cgccagggtg gtttttcttt tcaccagtga gacgggcaac agctgattgc   3900
ccttcaccgc ctggccctga gagagttgca gcaagcggtc cacgctggtt tgccccagca   3960
ggcgaaaatc ctgtttgatg gtggttaacg gcgggatata acatgagctg tcttcggtat   4020
cgtcgtatcc cactaccgag atatccgcac caacgcgcag cccggactcg gtaatggcgc   4080
gcattgcgcc cagcgccatc tgatcgttgg caaccagcat cgcagtggga acgatgccct   4140
cattcagcat ttgcatggtt tgttgaaaac cggacatggc actccagtcg ccttcccgtt   4200
ccgctatcgg ctgaatttga ttgcgagtga gatatttatg ccagccagcc agacgcagac   4260
gcgccgagac agaacttaat gggcccgcta acagcgcgat ttgctggtga cccaatgcga   4320
ccagatgctc cacgcccagt cgcgtaccgt cttcatggga gaaaataata ctgttgatgg   4380
gtgtctggtc agagacatca agaaataacg ccggaacatt agtgcaggca gcttccacag   4440
caatggcatc ctggtcatcc agcggatagt taatgatcag cccactgacg cgttgcgcga   4500
gaagattgtg caccgccgct ttacaggctt cgacgccgct tcgttctacc atcgacacca   4560
ccacgctggc acccagttga tcggcgcgag atttaatcgc cgcgacaatt tgcgacggcg   4620
cgtgcagggc cagactggag gtggcaacgc caatcagcaa cgactgtttg cccgccagtt   4680
gttgtgccac gcggttggga atgtaattca gctccgccat cgccgcttcc actttttccc   4740
gcgttttcgc agaaacgtgg ctggcctggt tcaccacgcg ggaaacggtc tgataagaga   4800
caccggcata ctctgcgaca tcgtataacg ttactggttt cacattcacc accctgaatt   4860
gactctcttc cgggcgctat catgccatac cgcgaaaggt tttgcgccat tcgatggtgt   4920
ccgggatctc gacgctctcc cttatgcgac tcctgcatta ggaagcagcc cagtagtagg   4980
ttgaggccgt tgagcaccgc cgccgcaagg aatggtgcat gcaaggagat ggcgcccaac   5040
agtcccccgg ccacggggcc tgccaccata cccacgccga aacaagcgct catgagcccg   5100
aagtggcgag cccgatcttc cccatcggtg atgtcggcga tataggcgcc agcaaccgca   5160
cctgtggcgc cggtgatgcc ggccacgatg cgtccggcgt agaggatcga gatctcgatc   5220
ccgcgaaatt aatacgactc actatagggg aattgtgagc ggataacaat tcccctctag   5280
aaataatttt gtttaacttt aagaaggaga tataccatgt ggtcccatcc tcaattcgag   5340
aagcatcacc atcaccatca ccatcacgga tctgaaaatc tctacttcca gcatacaagt   5400
ttgtacaaaa aagctgaacg agaaacgtaa aatgatataa atatcaatat attaaattag   5460
attttgcata aaaaacagac tacataatac tgtaaaacac aacatatcca gtcactatgg   5520
cggccgcatt aggcacccca ggctttacac tttatgcttc cggctcgtat aatgtgtgga   5580
ttttgagtta ggatccgtcg agattttcag ga                                 5612
```

<210> SEQ ID NO 5
<211> LENGTH: 8805

<212> TYPE: DNA
<213> ORGANISM: Artificial Sequence
<220> FEATURE:
<223> OTHER INFORMATION: Synthetic Construct - pcDNA3.1-ccdB-PE38-6xHis

<400> SEQUENCE: 5
gttaggcgtt ttgcgctgct tcgcgatgta cgggccagat atacgcgttg acattgatta 60
ttgactagtt attaatagta atcaattacg gggtcattag ttcatagccc atatatggag 120
ttccgcgtta cataacttac ggtaaatggc ccgcctggct gaccgcccaa cgacccccgc 180
ccattgacgt caataatgac gtatgttccc atagtaacgc caatagggac tttccattga 240
cgtcaatggg tggagtattt acggtaaact gcccacttgg cagtacatca agtgtatcat 300
atgccaagta cgccccctat tgacgtcaat gacggtaaat ggcccgcctg gcattatgcc 360
cagtacatga ccttatggga ctttcctact tggcagtaca tctacgtatt agtcatcgct 420
attaccatgg tgatgcggtt ttggcagtac atcaatgggc gtggatagcg gtttgactca 480
cggggatttc caagtctcca ccccattgac gtcaatggga gtttgttttg gcaccaaaat 540
caacgggact ttccaaaatg tcgtaacaac tccgccccat tgacgcaaat gggcggtagg 600
cgtgtacggt gggaggtcta tataagcaga gctcgtttag tgaaccgtca gatcgcctgg 660
agacgccatc cacgctgttt tgacctccat agaagacacc gggaccgatc cagcctccgg 720
actctagagg atcgaaccct tgaattcaca agtttgtaca aaaaagctga acgagaaacg 780
taaaatgata taaatatcaa tatattaaat tagattttgc ataaaaaaca gactacataa 840
tactgtaaaa cacaacatat ccagtcacta tggcggccgc attaggcacc ccaggcttta 900
cactttatgc ttccggctcg tataatgtgt ggattttgag ttaggatccg tcgagatttt 960
caggagctaa ggaagctaaa atggagaaaa aaatcactgg atataccacc gttgatatat 1020
cccaatggca tcgtaaagaa cattttgagg catttcagtc agttgctcaa tgtacctata 1080
accagaccgt tcagctggat attacggcct ttttaaagac cgtaaagaaa aataagcaca 1140
agttttatcc ggcctttatt cacattcttg cccgcctgat gaatgctcat ccggaattcc 1200
gtatggcaat gaaagacggt gagctggtga tatgggatag tgttcaccct tgttacaccg 1260
ttttccatga gcaaactgaa acgttttcat cgctctggag tgaataccac gacgatttcc 1320
ggcagtttct acacatatat tcgcaagatg tggcgtgtta cggtgaaaac ctggcctatt 1380
tccctaaagg gtttattgag aatatgtttt tcgtctcagc caatccctgg gtgagtttca 1440
ccagttttga tttaaacgtg gccaatatgg acaacttctt cgcccccgtt ttcaccatgg 1500
gcaaatatta tacgcaaggc gacaaggtgc tgatgccgct ggcgattcag gttcatcatg 1560
ccgtttgtga tggcttccat gtcggcagaa tgcttaatga attacaacag tactgcgatg 1620
agtggcaggg cggggcgtaa agatctggat ccggcttact aaaagccaga taacagtatg 1680
cgtatttgcg cgctgatttt tgcggtataa gaatatatac tgatatgtat acccgaagta 1740
tgtcaaaaag aggtatgcta tgaagcagcg tattacagtg acagttgaca gcgacagcta 1800
tcagttgctc aaggcatata tgatgtcaat atctccggtc tggtaagcac aaccatgcag 1860
aatgaagccc gtcgtctgcg tgccgaacgc tggaaagcgg aaaatcagga agggatggct 1920
gaggtcgccc ggtttattga aatgaacggc tcttttgctg acgagaacag gggctggtga 1980
aatgcagttt aaggtttaca cctataaaag agagagccgt tatcgtctgt ttgtggatgt 2040
acagagtgat attattgaca cgcccgggcg acggatggtg atccccctgg ccagtgcacg 2100
tctgctgtca gataaagtct cccgtgaact ttacccggtg gtgcatatcg ggatgaaag 2160 ctggcgcatg atgaccaccg atatggccag tgtgccggtc tccgttatcg gggaagaagt 2220
ggctgatctc agccaccgcg aaaatgacat caaaaacgcc attaacctga tgttctgggg 2280
aatataaatg tcaggctccc ttatacacag ccagtctgca ggtcgaccat agtgactgga 2340
tatgttgtgt tttacagtat tatgtagtct gtttttatg caaaatctaa tttaatatat 2400
tgatatttat atcattttac gtttctcgtt cagctttctt gtacaaagtg gttgatgggg 2460
gtggcggatc caccggtgca agtggcggac ctgagggcgg atctcttgct gcgctcacag 2520
ctcatcaagc ttgtcatctg cctcttgaaa cgtttaccag acatcgccag ccacggggat 2580
gggaacagct ggagcagtgt ggatatccgg tgcagagact tgtggctctt tacttggcgg 2640
cccggctttc ctggaaccaa gtggatcaag tcataaggaa tgcattggct tcacctggga 2700
gcggtggtga cttgggggaa gctataagag aacagcccga acaggcacgc cttgcgctta 2760
cattggcagc ggcagagagc gagaggttcg taagacaagg tacgggaaat gatgaagcgg 2820
gagcagccaa tgggcccgca gattctggtg atgcactttt ggagcggaac tatcctaccg 2880
gagcggagtt tctgggtgac ggaggtgacg tatcattcag tactcgcggg acccagaatt 2940
ggacagttga gcggctcctg caggcacaca ggcaactcga agagcgggga tacgtctttg 3000
ttggatatca cggtaccttt cttgaggcag cgcagtcaat agtgtttggc ggtgtgcgag 3060
caagatctca ggatctcgac gctatttgga ggggctttta catagcaggg gaccctgctt 3120
tggcctacgg ctatgcccaa gatcaggagc ccgatgctcg gggacggata aggaatgggg 3180
cgctcctccg agtctatgtt cctcgatctt ccctgccagg gttctaccga acaagtttga 3240
cacttgcggc cccggaagcg gccggtgagg tagagcggtt gattggacat cctcttccct 3300
tgcggttgga tgccatcacg ggcccgaggg aagagggggg tagactggag acaatcttgg 3360
ggtggccact cgcagagcgg acggtggtga ttccatcagc gatccccacc gatccgcgca 3420
atgtgggcgg ggatttggat ccttcttcta tacctgacaa ggagcaggcg atctccgcct 3480
tgcccgatta cgcaagtcaa ccaggtaagc cgcctcacca ccatcatcac catcgggaag 3540
acctgaagta agggccctag taatgagttt gatatctcga caatcaacct ctggattaca 3600
aaatttgtga aagattgact ggtattctta actatgttgc tccttttacg ctatgtggat 3660
acgctgcttt aatgcctttg tatcatgcta ttgcttcccg tatggctttc attttctcct 3720
ccttgtataa atcctggttg ctgtctcttt atgaggagtt gtggcccgtt gtcaggcaac 3780
gtggcgtggt gtgcactgtg tttgctgacg caacccccac tggttggggc attgccacca 3840
cctgtcagct cctttccggg actttcgctt tccccctccc tattgccacg gcggaactca 3900
tcgccgcctg ccttgcccgc tgctggacag gggctcggct gttgggcact gacaattccg 3960
tggtgttgtc ggggaagctg acgtcctttc catggctgct cgcctgtgtt gccacctgga 4020
ttctgcgcgg gacgtccttc tgctacgtcc cttcggccct caatccagcg gaccttcctt 4080
cccgcggcct gctgccggct ctgcggcctc ttccgcgtct tcgccttcgc cctcagacga 4140
gtcggatctc cctttgggcc gcctccccgc ctggaacggg ggaggctaac tgaaacacgg 4200
aaggagacaa taccggaagg aacccgcgct atgacggcaa taaaaagaca gaataaaacg 4260
cacgggtgtt gggtcgtttg ttcataaacg cggggttcgg tcccagggct ggcactctgt 4320
cgataccccca ccgagacccc attggggcca atacgcccgc gtttcttcct tttccccacc 4380
ccaccccccca agttcgggtg aaggcccagg gctcgcagcc aacgtcgggg cggcaggccc 4440
tgccatagca gatctgcgca gctggggctc tagggggtat ccccacgcgc cctgtagcgg 4500
cgcattaagc gcggcgggtg tggtggttac gcgcagcgtg accgctacac ttgccagcgc 4560
cctagcgccc gctcctttcg ctttcttccc ttcctttctc gccacgttcg ccggctttcc 4620
ccgtcaagct ctaaatcggg ggctcccttt agggttccga tttagtgctt tacggcacct 4680
cgaccccaaa aaacttgatt agggtgatgg ttcacgtagt gggccatcgc cctgatagac 4740
ggtttttcgc cctttgacgt tggagtccac gttctttaat agtggactct tgttccaaac 4800
tggaacaaca ctcaacccta tctcggtcta ttcttttgat ttataaggga ttttgccgat 4860
ttcggcctat tggttaaaaa atgagctgat ttaacaaaaa tttaacgcga attaattctg 4920
tggaatgtgt gtcagttagg gtgtggaaag tccccaggct ccccagcagg cagaagtatg 4980
caaagcatgc atctcaatta gtcagcaacc aggtgtggaa agtccccagg ctccccagca 5040
ggcagaagta tgcaaagcat gcatctcaat tagtcagcaa ccatagtccc gcccctaact 5100
ccgcccatcc cgcccctaac tccgcccagt tccgcccatt ctccgcccca tggctgacta 5160
atttttttta tttatgcaga ggccgaggcc gcctctgcct ctgagctatt ccagaagtag 5220
tgaggaggct tttttggagg cctaggcttt tgcaaaaagc tcccgggagc ttgtatatcc 5280
attttcggat ctgatcaaga gacaggatga ggatcgtttc gcatgattga acaagatgga 5340
ttgcacgcag gttctccggc cgcttgggtg gagaggctat tcggctatga ctgggcacaa 5400
cagacaatcg gctgctctga tgccgccgtg ttccggctgt cagcgcaggg gcgcccggtt 5460
ctttttgtca agaccgacct gtccggtgcc ctgaatgaac tgcaggacga ggcagcgcgg 5520
ctatcgtggc tggccacgac gggcgttcct tgcgcagctg tgctcgacgt tgtcactgaa 5580
gcgggaaggg actggctgct attgggcgaa gtgccggggc aggatctcct gtcatctcac 5640
cttgctcctg ccgagaaagt atccatcatg gctgatgcaa tgcggcggct gcatacgctt 5700
gatccggcta cctgcccatt cgaccaccaa gcgaaacatc gcatcgagcg agcacgtact 5760
cggatggaag ccggtcttgt cgatcaggat gatctggacg aagagcatca ggggctcgcg 5820
ccagccgaac tgttcgccag gctcaaggcg cgcatgcccg acggcgagga tctcgtcgtg 5880
acccatggcg atgcctgctt gccgaatatc atggtggaaa atggccgctt ttctggattc 5940
atcgactgtg gccggctggg tgtggcggac cgctatcagg acatagcgtt ggctacccgt 6000
gatattgctg aagagcttgg cggcgaatgg gctgaccgct tcctcgtgct ttacggtatc 6060
gccgctcccg attcgcagcg catcgccttc tatcgccttc ttgacgagtt cttctgagcg 6120
ggactctggg gttcgcgaaa tgaccgacca agcgacgccc aacctgccat cacgagattt 6180
cgattccacc gccgccttct atgaaaggtt gggcttcgga atcgttttcc gggacgccgg 6240
ctggatgatc ctccagcgcg gggatctcat gctggagttc ttcgcccacc ccaacttgtt 6300
tattgcagct tataatggtt acaaataaag caatagcatc acaaatttca caaataaagc 6360
atttttttca ctgcattcta gttgtggttt gtccaaactc atcaatgtat cttatcatgt 6420
ctgtataccg tcgacctcta gctagagctt ggcgtaatca tggtcatagc tgtttcctgt 6480
gtgaaattgt tatccgctca caattccaca caacatacga gccggaagca taaagtgtaa 6540
agcctggggt gcctaatgag tgagctaact cacattaatt gcgttgcgct cactgcccgc 6600
tttccagtcg ggaaacctgt cgtgccagct gcattaatga atcggccaac gcgcggggag 6660
aggcggtttg cgtattgggc gctcttccgc ttcctcgctc actgactcgc tgcgctcggt 6720
cgttcggctg cggcgagcgg tatcagctca ctcaaaggcg gtaatacggt tatccacaga 6780
atcaggggat aacgcaggaa agaacatgtg agcaaaaggc cagcaaaagg ccaggaaccg 6840
taaaaaggcc gcgttgctgg cgtttttcca taggctccgc ccccctgacg agcatcacaa 6900

```
aaatcgacgc tcaagtcaga ggtggcgaaa cccgacagga ctataaagat accaggcgtt   6960

tccccctgga agctccctcg tgcgctctcc tgttccgacc ctgccgctta ccggatacct   7020

gtccgccttt ctcccttcgg gaagcgtggc gctttctcat agctcacgct gtaggtatct   7080

cagttcggtg taggtcgttc gctccaagct gggctgtgtg cacgaacccc ccgttcagcc   7140

cgaccgctgc gccttatccg gtaactatcg tcttgagtcc aacccggtaa gacacgactt   7200

atcgccactg gcagcagcca ctggtaacag gattagcaga gcgaggtatg taggcggtgc   7260

tacagagttc ttgaagtggt ggcctaacta cggctacact agaagaacag tatttggtat   7320

ctgcgctctg ctgaagccag ttaccttcgg aaaaagagtt ggtagctctt gatccggcaa   7380

acaaaccacc gctggtagcg gtggtttttt tgtttgcaag cagcagatta cgcgcagaaa   7440

aaaaggatct caagaagatc ctttgatctt ttctacgggg tctgacgctc agtggaacga   7500

aaactcacgt taagggattt tggtcatgag attatcaaaa aggatcttca cctagatcct   7560

tttaaattaa aaatgaagtt ttaaatcaat ctaaagtata tatgagtaaa cttggtctga   7620

cagttaccaa tgcttaatca gtgaggcacc tatctcagcg atctgtctat ttcgttcatc   7680

catagttgcc tgactccccg tcgtgtagat aactacgata cgggagggct taccatctgg   7740

ccccagtgct gcaatgatac cgcgagaccc acgctcaccg gctccagatt tatcagcaat   7800

aaaccagcca gccggaaggg ccgagcgcag aagtggtcct gcaactttat ccgcctccat   7860

ccagtctatt aattgttgcc gggaagctag agtaagtagt tcgccagtta atagtttgcg   7920

caacgttgtt gccattgcta caggcatcgt ggtgtcacgc tcgtcgtttg gtatggcttc   7980

attcagctcc ggttcccaac gatcaaggcg agttacatga tcccccatgt tgtgcaaaaa   8040

agcggttagc tccttcggtc ctccgatcgt tgtcagaagt aagttggccg cagtgttatc   8100

actcatggtt atggcagcac tgcataattc tcttactgtc atgccatccg taagatgctt   8160

ttctgtgact ggtgagtact caaccaagtc attctgagaa tagtgtatgc ggcgaccgag   8220

ttgctcttgc ccggcgtcaa tacgggataa taccgcgcca catagcagaa ctttaaaagt   8280

gctcatcatt ggaaaacgtt cttcggggcg aaaactctca aggatcttac cgctgttgag   8340

atccagttcg atgtaaccca ctcgtgcacc caactgatct tcagcatctt ttactttcac   8400

cagcgtttct gggtgagcaa aaacaggaag gcaaaatgcc gcaaaaaagg gaataagggc   8460

gacacggaaa tgttgaatac tcatactctt cctttttcaa tattattgaa gcatttatca   8520

gggttattgt ctcatgagcg gatacatatt tgaatgtatt tagaaaaata aacaaatagg   8580

ggttccgcgc acatttcccc gaaaagtgcc acctgacgtc gacggatcgg gagatctccc   8640

gatcccctat ggtcgactct cagtacaatc tgctctgatg ccgcatagtt aagccagtat   8700

ctgctccctg cttgtgtgtt ggaggtcgct gagtagtgcg cgagcaaaat ttaagctaca   8760

acaaggcaag gcttgaccga caattgcatg aagaatctgc ttagg                   8805
```

<210> SEQ ID NO 6
<211> LENGTH: 3
<212> TYPE: DNA
<213> ORGANISM: Artificial Sequence
<220> FEATURE:
<223> OTHER INFORMATION: Synthetic Construct - type II CRISPR-Cas
protospacer-adjacent motif (PAM)
<220> FEATURE:
<221> NAME/KEY: misc_feature
<222> LOCATION: (1)..(1)
<223> OTHER INFORMATION: n is a, c, g, or t

<400> SEQUENCE: 6 ngg 3

<210> SEQ ID NO 7
<211> LENGTH: 23
<212> TYPE: DNA
<213> ORGANISM: Artificial Sequence
<220> FEATURE:
<223> OTHER INFORMATION: Synthetic Construct - type II CRISPR-Cas target site sequence with protospacer-adjacent motif (PAM)
<220> FEATURE:
<221> NAME/KEY: misc_feature
<222> LOCATION: (1)..(21)
<223> OTHER INFORMATION: n is a, c, g, or t

<400> SEQUENCE: 7
nnnnnnnnnn nnnnnnnnnn ngg 23

<210> SEQ ID NO 8
<211> LENGTH: 4
<212> TYPE: DNA
<213> ORGANISM: Artificial Sequence
<220> FEATURE:
<223> OTHER INFORMATION: Synthetic Construct - type V CRISPR-Cas protospacer-adjacent motif (PAM)
<220> FEATURE:
<221> NAME/KEY: misc_feature
<222> LOCATION: (4)..(4)
<223> OTHER INFORMATION: v is a, c, or g

<400> SEQUENCE: 8 tttv 4

<210> SEQ ID NO 9
<211> LENGTH: 27
<212> TYPE: DNA
<213> ORGANISM: Artificial Sequence
<220> FEATURE:
<223> OTHER INFORMATION: Synthetic Construct - type V CRISPR-Cas target site sequence with protospacer-adjacent motif (PAM)
<220> FEATURE:
<221> NAME/KEY: misc_feature
<222> LOCATION: (4)..(4)
<223> OTHER INFORMATION: v is a, c, or g
<220> FEATURE:
<221> NAME/KEY: misc_feature
<222> LOCATION: (5)..(27)
<223> OTHER INFORMATION: n is a, c, g, or t

<400> SEQUENCE: 9
tttvnnnnnn nnnnnnnnnn nnnnnnn 27

<210> SEQ ID NO 10
<211> LENGTH: 86
<212> TYPE: DNA
<213> ORGANISM: Artificial Sequence
<220> FEATURE:
<223> OTHER INFORMATION: Synthetic Construct - tracrRNA

<400> SEQUENCE: 10
gtttcagagc tatgctggaa acagcatagc aagttgaaat aaggctagtc cgttatcaac 60
ttgaaaaagt ggcaccgagt cggtgc 86

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct - optimized direct repeat Lachnospiraceae bacterium Cpf1

<400> SEQUENCE: 11
taatttctac tcttgtagat 20

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct - optimized direct repeat Acidaminococcus sp. Cpf1

<400> SEQUENCE: 12
taatttctac taagtgtaga t 21

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct - DPH1 gRNA DNA sequence

<400> SEQUENCE: 13
tccagcaccc acctctgcca 20

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct - DPH1 gRNA DNA sequence

<400> SEQUENCE: 14
gtggccttgc aaatgccgga 20

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct - DPH1 gRNA DNA sequence

<400> SEQUENCE: 15
tgtggatgac ttcacagcga 20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct - DPH1 gRNA DNA sequence

<400> SEQUENCE: 16
aatggtgctg accagggcaa 20

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct - DPH2 gRNA DNA sequence

<400> SEQUENCE: 17
gatgtttagc agccctgccg 20

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct - DPH2 gRNA DNA sequence

<400> SEQUENCE: 18
tgggtgacac agcctacggc 20

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct - DPH2 gRNA DNA sequence

<400> SEQUENCE: 19
agaacgttga cgaagcacga 20

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct - DPH2 gRNA DNA sequence

<400> SEQUENCE: 20
gagggccaga gatgcccgcg 20

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct - DPH3 gRNA DNA sequence

<400> SEQUENCE: 21
agataacttc tccatcacca 20

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct - DPH3 gRNA DNA sequence

<400> SEQUENCE: 22
atggagaagt tatctccaca 20

<210> SEQ ID NO 23
<211> LENGTH: 20
<212> TYPE: DNA
<213> ORGANISM: Artificial Sequence
<220> FEATURE:
<223> OTHER INFORMATION: Synthetic Construct - DPH3 gRNA DNA sequence

<400> SEQUENCE: 23
tggagaagtt atctccacat 20

<210> SEQ ID NO 24
<211> LENGTH: 20
<212> TYPE: DNA
<213> ORGANISM: Artificial Sequence
<220> FEATURE:
<223> OTHER INFORMATION: Synthetic Construct - DPH3 gRNA DNA sequence

<400> SEQUENCE: 24
ctcgtcatga aacactgcca 20

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct - DPH5 gRNA DNA sequence

<400> SEQUENCE: 25
caaatggatc accaaccaca 20

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct - DPH5 gRNA DNA sequence

<400> SEQUENCE: 26
tggtttacac tcatataccg 20

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct - DPH5 gRNA DNA sequence

<400> SEQUENCE: 27
tttacactca tataccgtgg 20

<210> SEQ ID NO 28
<211> LENGTH: 20
<212> TYPE: DNA
<213> ORGANISM: Artificial Sequence
<220> FEATURE:
<223> OTHER INFORMATION: Synthetic Construct - DPH5 gRNA DNA sequence

<400> SEQUENCE: 28
aggaggcagc atacatccaa 20

<210> SEQ ID NO 29
<211> LENGTH: 20
<212> TYPE: DNA
<213> ORGANISM: Artificial Sequence
<220> FEATURE:
<223> OTHER INFORMATION: Synthetic Construct - DPH7 gRNA DNA sequence

<400> SEQUENCE: 29
gcgggaccta ccagctgcgg 20

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct - DPH7 gRNA DNA sequence

<400> SEQUENCE: 30
agacggccta aacggacctg 20

<210> SEQ ID NO 31
<211> LENGTH: 20

<212> TYPE: DNA
<213> ORGANISM: Artificial Sequence
<220> FEATURE:
<223> OTHER INFORMATION: Synthetic Construct - DPH7 gRNA DNA sequence

<400> SEQUENCE: 31
agccagacac tgctcctcca 20

<210> SEQ ID NO 32
<211> LENGTH: 20
<212> TYPE: DNA
<213> ORGANISM: Artificial Sequence
<220> FEATURE:
<223> OTHER INFORMATION: Synthetic Construct - DPH7 gRNA DNA sequence

<400> SEQUENCE: 32
cctcaggtgt cacatcccgg 20

<210> SEQ ID NO 33
<211> LENGTH: 20
<212> TYPE: DNA
<213> ORGANISM: Artificial Sequence
<220> FEATURE:
<223> OTHER INFORMATION: Synthetic Construct - DNAJC24 gRNA DNA sequence

<400> SEQUENCE: 33
aaaggattgg tacagcatcc 20

<210> SEQ ID NO 34
<211> LENGTH: 20
<212> TYPE: DNA
<213> ORGANISM: Artificial Sequence
<220> FEATURE:
<223> OTHER INFORMATION: Synthetic Construct - DNAJC24 gRNA DNA sequence

<400> SEQUENCE: 34
ttgcagatgg gtctgctccc 20

<210> SEQ ID NO 35
<211> LENGTH: 20
<212> TYPE: DNA
<213> ORGANISM: Artificial Sequence
<220> FEATURE:
<223> OTHER INFORMATION: Synthetic Construct - DNAJC24 gRNA DNA sequence

<400> SEQUENCE: 35
caaagtacag atgtaccagc 20

<210> SEQ ID NO 36
<211> LENGTH: 20
<212> TYPE: DNA
<213> ORGANISM: Artificial Sequence
<220> FEATURE:
<223> OTHER INFORMATION: Synthetic Construct - DNAJC24 gRNA DNA sequence

<400> SEQUENCE: 36
agatgtacca gcaggaacag 20

<210> SEQ ID NO 37
<211> LENGTH: 20
<212> TYPE: DNA
<213> ORGANISM: Artificial Sequence
<220> FEATURE:
<223> OTHER INFORMATION: Synthetic Construct - HBEGF gRNA DNA sequence

<400> SEQUENCE: 37
aagagcttca gcaccaccga 20

<210> SEQ ID NO 38
<211> LENGTH: 20
<212> TYPE: DNA
<213> ORGANISM: Artificial Sequence
<220> FEATURE:
<223> OTHER INFORMATION: Synthetic Construct - HBEGF gRNA DNA sequence

<400> SEQUENCE: 38
ggtccgtgga tacagtggga 20

<210> SEQ ID NO 39
<211> LENGTH: 20
<212> TYPE: DNA
<213> ORGANISM: Artificial Sequence
<220> FEATURE:
<223> OTHER INFORMATION: Synthetic Construct - HBEGF gRNA DNA sequence

<400> SEQUENCE: 39
tcatgggctg agcctcccag 20

<210> SEQ ID NO 40
<211> LENGTH: 20
<212> TYPE: DNA
<213> ORGANISM: Artificial Sequence
<220> FEATURE:
<223> OTHER INFORMATION: Synthetic Construct - HBEGF gRNA DNA sequence

<400> SEQUENCE: 40
actggccaca ccaaacaagg 20

<210> SEQ ID NO 41
<211> LENGTH: 20
<212> TYPE: DNA
<213> ORGANISM: Artificial Sequence
<220> FEATURE:
<223> OTHER INFORMATION: Synthetic Construct - FURIN gRNA DNA sequence

<400> SEQUENCE: 41
gaaggtcttc accaacacgt 20

<210> SEQ ID NO 42
<211> LENGTH: 20
<212> TYPE: DNA
<213> ORGANISM: Artificial Sequence
<220> FEATURE:
<223> OTHER INFORMATION: Synthetic Construct - FURIN gRNA DNA sequence

<400> SEQUENCE: 42
tctgcagccg gctgtgccgc 20

<210> SEQ ID NO 43
<211> LENGTH: 20
<212> TYPE: DNA
<213> ORGANISM: Artificial Sequence
<220> FEATURE:
<223> OTHER INFORMATION: Synthetic Construct - FURIN gRNA DNA sequence

<400> SEQUENCE: 43
gtggtctcca ttctggacga 20

<210> SEQ ID NO 44
<211> LENGTH: 20
<212> TYPE: DNA
<213> ORGANISM: Artificial Sequence
<220> FEATURE:
<223> OTHER INFORMATION: Synthetic Construct - FURIN gRNA DNA sequence

<400> SEQUENCE: 44
gcacggcaca cggtgtgcgg 20

<210> SEQ ID NO 45
<211> LENGTH: 20
<212> TYPE: DNA
<213> ORGANISM: Artificial Sequence
<220> FEATURE:
<223> OTHER INFORMATION: Synthetic Construct - MESDC2 gRNA DNA sequence

<400> SEQUENCE: 45
tcgcgatggg agctacgcct 20

<210> SEQ ID NO 46
<211> LENGTH: 20
<212> TYPE: DNA
<213> ORGANISM: Artificial Sequence
<220> FEATURE:
<223> OTHER INFORMATION: Synthetic Construct - MESDC2 gRNA DNA sequence

<400> SEQUENCE: 46
agaggcacaa agcaggacca 20

<210> SEQ ID NO 47
<211> LENGTH: 20
<212> TYPE: DNA
<213> ORGANISM: Artificial Sequence
<220> FEATURE:
<223> OTHER INFORMATION: Synthetic Construct - MESDC2 gRNA DNA sequence

<400> SEQUENCE: 47
gaaattacga gcctctggca 20

<210> SEQ ID NO 48
<211> LENGTH: 20
<212> TYPE: DNA
<213> ORGANISM: Artificial Sequence
<220> FEATURE:
<223> OTHER INFORMATION: Synthetic Construct - MESDC2 gRNA DNA sequence

<400> SEQUENCE: 48
gctatcttca tgcttcgcga 20

<210> SEQ ID NO 49
<211> LENGTH: 20
<212> TYPE: DNA
<213> ORGANISM: Artificial Sequence
<220> FEATURE:
<223> OTHER INFORMATION: Synthetic Construct - LRP1 gRNA DNA sequence

<400> SEQUENCE: 49
gcgaccagag ctgagagcag 20

<210> SEQ ID NO 50
<211> LENGTH: 20
<212> TYPE: DNA
<213> ORGANISM: Artificial Sequence
<220> FEATURE:
<223> OTHER INFORMATION: Synthetic Construct - LRP1 gRNA DNA sequence

<400> SEQUENCE: 50
gcggaactcg cccacaccac 20

<210> SEQ ID NO 51
<211> LENGTH: 20
<212> TYPE: DNA
<213> ORGANISM: Artificial Sequence
<220> FEATURE:
<223> OTHER INFORMATION: Synthetic Construct - LRP1 gRNA DNA sequence

<400> SEQUENCE: 51
agtgagttcc gctgtgccaa 20

<210> SEQ ID NO 52
<211> LENGTH: 20
<212> TYPE: DNA
<213> ORGANISM: Artificial Sequence
<220> FEATURE:
<223> OTHER INFORMATION: Synthetic Construct - LRP1 gRNA DNA sequence

<400> SEQUENCE: 52
tgtggacgag ttccgctgca 20

<210> SEQ ID NO 53
<211> LENGTH: 20
<212> TYPE: DNA
<213> ORGANISM: Artificial Sequence
<220> FEATURE:
<223> OTHER INFORMATION: Synthetic Construct - LRP1B gRNA DNA sequence

<400> SEQUENCE: 53
attgccaggg tgctgaccgt 20

<210> SEQ ID NO 54
<211> LENGTH: 20
<212> TYPE: DNA
<213> ORGANISM: Artificial Sequence
<220> FEATURE:
<223> OTHER INFORMATION: Synthetic Construct - LRP1B gRNA DNA sequence

<400> SEQUENCE: 54
gacgaaggag tacattgtca 20

<210> SEQ ID NO 55
<211> LENGTH: 20
<212> TYPE: DNA
<213> ORGANISM: Artificial Sequence
<220> FEATURE:
<223> OTHER INFORMATION: Synthetic Construct - LRP1B gRNA DNA sequence

<400> SEQUENCE: 55
ggtgacacat acagaaccgt 20

<210> SEQ ID NO 56
<211> LENGTH: 20
<212> TYPE: DNA
<213> ORGANISM: Artificial Sequence
<220> FEATURE:
<223> OTHER INFORMATION: Synthetic Construct - LRP1B gRNA DNA sequence

<400> SEQUENCE: 56
cgtgaaagtc taaagcacga 20

METHODS AND KITS FOR IDENTIFYING A PROTEIN ASSOCIATED WITH RECEPTOR-LIGAND INTERACTIONS

RELATED APPLICATION

This application claims priority to U.S. Provisional Patent Application No. 62/677,875 filed on May 30, 2018, the content of which is hereby incorporated by reference in its entirety.

FIELD

The disclosure relates to methods, probes, recombinant cell lines, recombinant toxin fusion, and kits for identifying a protein associated with receptor-ligand interactions.

BACKGROUND

Cells secrete thousands of proteins, collectively known as the secretome. These proteins, which include hormones, growth factors, and other autocrine/paracrine signaling factors, play a vital role in development, growth control, and tissue homeostasis. Disruption of intercellular signaling is causally implicated in developmental disorders, cancer, and immune disorders. Secreted or otherwise released signaling factors trigger a specific signaling cascade once bound to their specific (cognate) receptor at the surface of the target cell. Thus, the identification of ligand/receptor interactions has far-reaching implications for both fundamental biomedical research and therapeutics. For example, 70% of drugs currently in the clinic target cell surface receptors and the success of antibody therapeutics in cancer and inflammatory diseases has further emphasized the exceptionally high therapeutic potential of the receptor-targeted medicines. Therefore, binding secreted proteins to their cognate cell-surface receptors is a critical step in understanding the basic signaling mechanisms underlying intercellular communication and in developing novel therapeutics.

However, connecting the estimated 3,000 secreted proteins to 2,500 cell-surface proteins remains a daunting task. Modern protein-protein interaction assays have been very successful in characterizing interactions between soluble intracellular proteins but there are no easily scalable methods for studying receptor/ligand interactions in an unbiased fashion. One of the few existing high-throughput assays, avidity based extracellular interaction screening (AVEXIS), utilizes multimerized extracellular domains of receptors to screen for putative ligands fixed on a plate. Consequently, this assay is not compatible with multi-spanning membrane receptors (such as GPCRs) or multi-subunit receptors. Moreover, it is possible that the observed receptor-ligand interaction is specific to the tested in vitro condition and may not hold true in vivo. Finally, the assay depends on cloning, expression and purification of every protein tested in the assay, which is particularly challenging for extracellular proteins. Thus, identifying ligand/receptor pairs has remained challenging and, consequently, a substantial fraction of known transmembrane receptors and soluble ligands remain orphans. These hurdles significantly slow both the basic understanding of extracellular signaling mechanisms and therapeutically relevant research.

SUMMARY

The present inventors have developed a method to identify receptors for extracellular proteins. This method overcomes one or more limitations of existing assays. The methods and compositions described herein exploit toxins, such as bacterial exotoxins. Toxins such as bacterial exotoxins, when fused to for example a secreted protein, can intoxicate cells in a receptor-dependent manner, which facilitates the identification of the cognate receptor through a genome-wide selection screen such as a Clustered Regularly Interspaced Short Palindromic Repeats (CRISPR)/Cas9-based positive selection screen. In some embodiments, in addition to a receptor, the present methods can also identify other factors for example factors required for receptor surface expression and functionalization, such as genes involved in receptor biogenesis, maturation, or trafficking, factors involved in ligand and/or receptor endocytosis, and intoxication factors that are required for toxin activity.

Accordingly, an aspect of the disclosure includes a method for identifying a protein associated with a receptor-ligand interaction, comprising the steps of:

(a) providing a population of engineered cells comprising a targeting library, wherein an individual engineered cell of the population contains a nucleic acid molecule of the targeting library, and wherein the nucleic acid molecule comprises a nucleic acid sequence complementary to a target gene, (b) contacting the population of cells for sufficient time with a recombinant toxin fusion comprising a toxin domain, a binding domain and optionally a translocation domain, thereby producing a selection pool of cells; and (c) sequencing one or more of the nucleic acid molecules of the targeting library comprised in one or more cells of the selection pool of cells, and identifying the target gene in the one or more cells, the target gene encoding protein associated with a receptor-ligand interaction.

In an embodiment, a population of engineered cells comprising a targeting library is contacted with a toxin. For example, this can be used as a control.

In an embodiment, the nucleic acid molecule comprising a nucleic acid sequence complementary to a target gene comprises or is a gRNA, siRNA, shRNA or miRNA, preferably a gRNA.

In an embodiment, the gRNA is part of a CRISPR-Cas system.

In another embodiment, the CRISPR-Cas system comprises Cas9.

In an embodiment, the CRISPR-Cas system comprises Cpf1.

In another embodiment, the targeting library is a mammalian library, preferably a human or mouse library.

In another embodiment, the targeting library is a whole genome library.

In another embodiment, the targeting library comprises nucleic acid molecules targeting cell surface receptors, preferably G protein coupled receptors (GPCRs).

In another embodiment, the targeting library comprises nucleic acid molecules targeting genes encoding proteins of cell surface receptor-mediated pathways.

In another embodiment, the targeting library comprises nucleic acid molecules targeting receptor maturation factor genes.

In another embodiment, the population of cells comprises cells from a mammalian cell line, preferably a human or mouse cell line.

In another embodiment, the mammalian cell line is A431, A549, HCT116, K562, HeLa, preferably HeLa-Kyoto, or HEK-293, preferably HEK-293T, or a haploid or near haploid cell line, preferably HAP1.

In another embodiment, the targeting library is transduced into the cells with at least one retroviral vector, preferably at least one lentiviral vector.

In another embodiment, the toxin or toxin domain is or comprises Diphtheria toxin (DTA), *Pseudomonas* exotoxin A (PE), saporin, gelonin, perfringolysin, listeriolysin, α-hemolysin, subtilase cytotoxin, bouganin, or ricin toxin domain, or a toxic fragment thereof.

In another embodiment, the binding domain is or comprises a receptor-binding molecule or a binding fragment thereof, a peptide or a binding fragment thereof, an antibody or a binding fragment thereof, a carbohydrate, a small molecule, or a lipid.

In another embodiment, the receptor-binding molecule is or comprises a ligand, or a binding fragment thereof, optionally an orphan ligand, or a binding fragment thereof.

In an embodiment, the receptor-binding molecule is or comprises a growth factor. In an embodiment, the growth factor is Epidermal Growth Factor (EGF), pleiotrophin (PTN), or Fibroblast Growth Factor (FGF). In an embodiment, the receptor-binding molecule is or comprises a cytokine. In an embodiment, the cytokine is chemokine (C-X-C motif) ligand 9 (CXCL9). In an embodiment, the receptor-binding molecule is or comprises a lysosomal enzyme. In an embodiment, the lysosomal enzyme is N-acetylglucosamine-6-sulfatase (GNS) or GM2 ganglioside activator (GM2A). In another embodiment, the receptor-binding molecule is or comprises EGF, PTN, CXCL9, GNS, GM2A or FGF, or a binding fragment thereof.

In another embodiment, the peptide is or comprises a TAT peptide, Aβ40 or Aβ42, or a binding fragment thereof.

In another embodiment, the binding domain comprises a post-translational modification.

In another embodiment, the post-translational modification is or comprises phosphorylation, acetylation, glycosylation, amidation, hydroxylation, methylation, ubiquitylation, or mannose-6-phosphate addition.

In another embodiment, the post-translational modification is or comprises mannose-6-phosphate addition.

In another embodiment, the translocation domain is or comprises DTA or PE translocation domain, or a transmembrane passage forming fragment thereof.

In some embodiments, the toxin domain is at the amino terminus of the recombinant toxin fusion. In other embodiments, the toxin domain is at the carboxyl terminus of the recombinant toxin fusion.

In other embodiments comprising a translocation domain, the binding domain is at an opposite terminus of the toxin domain. In some embodiments, the binding domain is fused to the toxin domain.

In another embodiment, the recombinant toxin fusion when administered to cells kills at least 99% of non-engineered cells (e.g. cells not comprising the targeting library).

In an embodiment, the sequencing comprises high-throughput sequencing.

Another aspect includes a method of producing a toxin-resistant cell line, comprising the steps of:

(a) introducing into cells of a selected cell line and expressing at least one nucleic acid molecule comprising nucleic acid sequence encoding Cas or Cpf1, and a nucleic acid sequence encoding at least one gRNA targeting DPH1, DPH2, DPH3, DPH5, DPH7, or DNAJC24, preferably DNAJC24; and (b) contacting the cells with a toxin for sufficient time to produce the toxin-resistant cell line, optionally at least 0.1 nM toxin for at least 2 days.

In one embodiment, the method is for producing a Diphtheria toxin (DTA)-resistant cell line, comprising the steps of:

(a) introducing into cells of a selected cell line and expressing at least one nucleic acid molecule comprising a nucleic acid sequence encoding Cas or Cpf1, and a nucleic acid sequence encoding at least one gRNA targeting HBEGF, DPH1, DPH2, DPH3, DPH5, DPH7, or DNAJC24, preferably DNAJC24; and (b) contacting the cells with DTA for sufficient time to produce the DTA-resistant cell line, optionally at least 0.1 nM DTA for at least 2 days.

Also provided in yet another aspect is a method of producing a *Pseudomonas* exotoxin A (PE)-resistant cell line, comprising the steps of:

(a) introducing into cells of a selected cell line and expressing at least one nucleic acid molecule comprising a nucleic acid sequence encoding Cas or Cpf1, and a nucleic acid sequence encoding at least one gRNA targeting FURIN, MESDC2, LRP1, LRP1B, DPH1, DPH2, DPH3, DPH5, DPH7, or DNAJC24, preferably DNAJC24; and (b) contacting the cells with PE for sufficient time to produce the PE-resistant cell line, optionally at least 0.1 nM PE for at least 2 days.

Also provided in another aspect is a method of producing a toxin-producing cell line, comprising the steps of:

(a) introducing into cells of a selected cell line and expressing at least one nucleic acid molecule comprising a nucleic acid sequence encoding Cas or Cpf1 and a nucleic acid sequence encoding at least one gRNA targeting DPH1, DPH2, DPH3, DPH5, DPH7, or DNAJC24, preferably DNAJC24;

(b) contacting the cells with a toxin for sufficient time, optionally at least 0.1 nM toxin for at least 2 days; and (c) introducing into the cells of step (b) and expressing a nucleic acid molecule comprising a nucleic acid sequence encoding the toxin or a recombinant toxin fusion.

Also provided in another aspect is a method of producing a toxin, comprising the steps of:

(a) introducing into cells of a selected cell line and expressing at least one nucleic acid molecule comprising a nucleic acid sequence encoding Cas or Cpf1 and a nucleic acid sequence encoding at least one gRNA targeting DPH1, DPH2, DPH3, DPH5, DPH7, or DNAJC24, preferably DNAJC24;

(b) contacting the cells with a toxin for sufficient time, optionally at least 0.1 nM toxin for at least 2 days; and (c) introducing into the cells of step (b) and expressing a nucleic acid molecule comprising a nucleic acid sequence encoding the toxin or a recombinant toxin fusion;

(d) growing the cell in media; and (e) collecting the media containing the toxin or the recombinant toxin fusion and optionally isolating the toxin or the recombinant toxin fusion.

Also provided in one aspect is a toxin-resistant cell line, each of the cells of the cell line comprising and expressing at least one nucleic acid molecule, comprising a nucleic acid sequence encoding Cas or Cpf1, and a nucleic acid sequence encoding at least one gRNA targeting DPH1, DPH2, DPH3, DPH5, DPH7, or DNAJC24, preferably DNAJC24.

In one embodiment, the cell line is a Diphtheria toxin (DTA)-resistant cell line comprising a population of cells comprising and expressing at least one nucleic acid molecule comprising a nucleic acid sequence encoding Cas or Cpf1, and a nucleic acid sequence encoding at least one gRNA targeting HBEGF, DPH1, DPH2, DPH3, DPH5, DPH7, or DNAJC24, preferably DNAJC24.

In an embodiment, the cell line is a *Pseudomonas* exotoxin A (PE)-resistant cell line, each of the cells of the cell line comprising and expressing at least one a nucleic acid molecule, comprising a nucleic acid sequence encoding Cas or Cpf1, and a nucleic acid sequence encoding at least one gRNA targeting FURIN, MESDC2, LRP1, LRP1B, DPH1, DPH2, DPH3, DPH5, DPH7, or DNAJC24, preferably DNAJC24.

Also provided in one aspect is a toxin-producing cell line, each of the cells of the cell line comprising at least one nucleic acid molecule, comprising a nucleic acid sequence encoding Cas or Cpf1, and a nucleic acid sequence encoding at least one gRNA targeting DPH1, DPH2, DPH3, DPH5, DPH7, or DNAJC24, preferably DNAJC24, and a nucleic acid sequence encoding a toxin or a recombinant toxin fusion.

Also provided is a nucleic acid molecule comprising a nucleic acid sequence encoding and capable of expressing a recombinant toxin fusion, wherein the recombinant toxin fusion comprising a toxin domain, a binding domain, and optionally a translocation domain, wherein the toxin domain is at the amino or carboxyl terminus of the recombinant toxin fusion, wherein the binding domain is at an opposite terminus of the toxin domain, and wherein the binding domain is or comprises a receptor-binding molecule, a peptide, an antibody, or a binding fragment thereof.

Also provided is a recombinant toxin fusion comprising a toxin domain, a binding domain, and optionally a translocation domain, wherein the toxin domain is at the amino or carboxyl terminus of the recombinant toxin fusion, wherein the binding domain is at an opposite terminus of the toxin domain, and wherein the binding domain is or comprises a receptor-binding molecule or a binding fragment thereof, a peptide or a binding fragment thereof, an antibody or a binding fragment thereof, a carbohydrate, a small molecule, or a lipid.

Also provided is a kit for identifying a protein associated with a receptor-ligand interaction comprising:

(a) a first cell line, (b) at least one nucleic acid molecule comprising a nucleic acid sequence encoding a recombinant toxin fusion and capable of expressing the recombinant toxin fusion or at least one recombinant toxin fusion, and (c) a targeting library comprising a plurality of nucleic acid molecules, wherein individual nucleic acid molecules target gene expression of specific genes, wherein the first cell line is resistant to the recombinant toxin fusion, and wherein the recombinant toxin fusion comprises a toxin domain, a binding domain, and optionally a translocation domain.

Also provided is a kit for identifying a protein associated with a receptor-ligand interaction comprising:

(a) a first cell line, (b) at least one recombinant toxin fusion, and wherein the recombinant toxin fusion comprises a toxin domain, a binding domain, and optionally a translocation domain, and optionally a targeting library comprising a plurality of nucleic acid molecules, wherein individual nucleic acid molecules target gene expression of specific genes.

In some embodiments, the kit includes instructions or is for performing a method described herein. The kit can include one or more components described herein.

Also provided is a comprising a polypeptide comprising an amino acid sequence encoding a recombinant toxin fusion, wherein the recombinant toxin fusion comprises a toxin domain, a binding domain, and optionally a translocation domain, wherein the toxin domain is at the amino or carboxyl terminus of the recombinant toxin fusion, wherein the binding domain is at an opposite terminus of the toxin domain, and wherein the binding domain is or comprises a receptor-binding molecule, a peptide, an antibody, or a binding fragment thereof, optionally the recombinant toxin fusion further comprises a multimerization domain. In an embodiment, the recombinant toxin fusion comprises multiple toxin domains. In an embodiment, the probe is for identifying a protein associated with a receptor-ligand interaction.

Other features and advantages of the present disclosure will become apparent from the following detailed description. It should be understood, however, that the detailed description and the specific examples while indicating embodiments of the disclosure are given by way of illustration only, the scope of the claims should not be limited by the embodiments set forth in the examples, but should be given the broadest interpretation consistent with the description as a whole.

BRIEF DESCRIPTION OF THE DRAWINGS

An embodiment of the present disclosure will now be described in relation to the drawings in which.

DETAILED DESCRIPTION

A. Definitions

Figure 1:
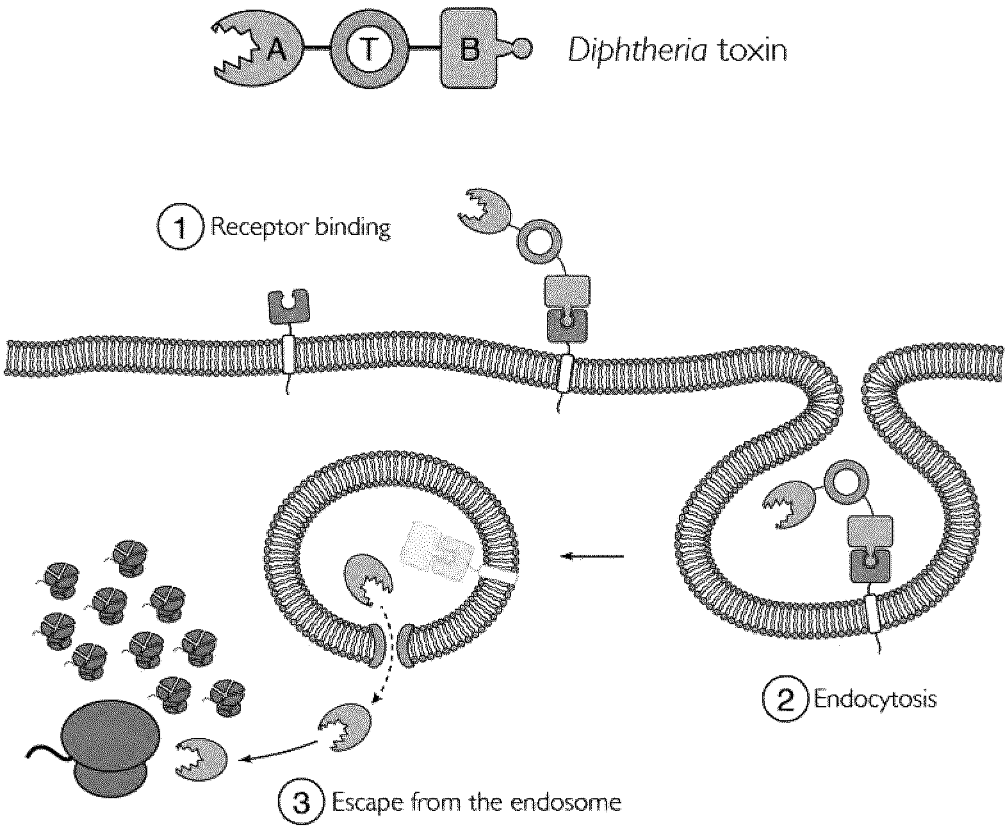
FIG. 1 shows a schematic diagram of an AB-type toxin as represented by Diphtheria toxin binding to receptor, undergoing endocytosis and escaping from the endosome.

Unless otherwise indicated, the definitions and embodiments described in this and other sections are intended to be applicable to all embodiments and aspects of the disclosure herein described for which they are suitable as would be understood by a person skilled in the art.

As used in this disclosure, the singular forms "a", "an" and "the" include plural references unless the content clearly dictates otherwise. For example, an embodiment including "a compound" should be understood to present certain aspects with one compound, or two or more additional compounds.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "nucleic acid molecule" or its derivatives, as used herein, is intended to include unmodified DNA or RNA or modified DNA or RNA and includes cDNA. For example, the nucleic acid molecules can be composed of single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triple-stranded regions comprising RNA or DNA or both RNA and DNA. The nucleic acid molecules may also contain one or more modified bases or DNA or RNA backbones modified for stability or for other reasons. "Modified" bases include, for example, tritiated bases and unusual bases such as inosine that bind naturally occurring bases. A variety of modifications can be made to DNA and RNA; thus "nucleic acid molecule" embraces chemically, enzymatically, or metabolically modified forms. The term "polynucleotide" shall have a corresponding meaning.

The nucleic acid can be either double stranded or single stranded, and represents the sense or antisense strand. The term "nucleic acid" includes the complementary nucleic acid sequences as well as the codon optimized or the synonymous codon equivalents.

In some embodiments, the expression "a plurality of nucleic acid molecules" is used to refer to nucleic acid molecules comprised in a targeting library that are introduced into a population of cells.

The term "engineered" when referring to cells means that the cells have been manipulated to contain a non-native nucleic acid molecule. The non-native nucleic acid molecule can be introduced into the cells in a number of ways known to the person skilled in art, for example, by way of transformation, transduction, transfection, transposition, and electroporation. Transformation typically refers to introduction of nucleic acid molecule in bacteria by methods known in art, for example, by heat shocking the bacterial cells. Transfection is the process of introducing a nucleic acid molecule into a eukaryotic cell, which may for example, involve lipid based methods. Transposition may involve the machinery of transposons, including target DNA sequences used by the transposon translocation machinery. Electroporation technique involves applying an electrical field to cells so to increase the permeability of the cell membrane, which would allow a nucleic acid molecule to be introduced into the cell. Transduction is the process by which a nucleic acid molecule is introduced into a cell by a virus or viral vector. Therefore, an "engineered" cell can be derived by various methods of introducing a nucleic acid molecule into a cell.

The expression "protein associated with a receptor-ligand interaction" encompasses proteins such as the receptor and the ligand themselves, as well as proteins involved in cell surface receptor-mediated pathways and receptor maturation factors. For example, a protein associated with a receptor-ligand interaction includes factors required for receptor surface expression and functionalization, such as genes involved in receptor biogenesis, maturation, or trafficking, and factors involved in ligand and/or receptor endocytosis. Proteins associated with a receptor-ligand interaction include, for example, proteins localized to the plasma membrane, endoplasmic reticulum (ER) membrane and other intracellular membranes; trafficking factors regulating endocytosis and receptor maturation; and transcription factors regulating the expression of cell surface proteins or any proteins.

The term "toxin" refers to poisonous or toxic material or product of plants, animals, microorganisms, including, but not limited to, bacteria, viruses, fungi, rickettsia or protozoa, or infectious substances, or a recombinant or synthesized molecule, whatever their origin and method of production, and includes any poisonous substance or biological product that may be engineered as a result of biotechnology, produced by a living organism; or any poisonous isomer or biological product, homolog, or derivative of such a substance. A toxin has a toxin domain that imparts toxicity to a cell. A toxin includes recombinant toxin fusion as described hereinbelow. A toxin as used herein intoxicates cells with picomolar potency. The skilled person recognizes that as long as the toxin can cause growth inhibition via receptor-mediated pathway, it can be used in the method for identifying a protein associated with a receptor-ligand interaction described herein. Growth inhibition at 25%, or even at 10%, may be adequate provided the cells have been incubated with the toxin for sufficient time. The skilled person can readily adjust toxicity in relation to incubation time or vice versa. The skilled person can also readily recognize "sufficient time" for incubating the cells with the toxin, for example, when non-engineered control cells incubated with toxin are all dead and there are survivors in the gRNA treated cell population.

The term "recombinant toxin fusion" refers to a fusion molecule that has a binding domain (for example, a ligand), a toxin domain, and optionally a translocation domain fused in any orientation which permits target binding and cell toxicity. As described herein, the toxin domain can be the toxin domain of a toxin, or a toxic fragment thereof. A recombinant toxin fusion as used herein intoxicates cells with picomolar potency. Similarly the binding domain can be a molecule that specifically binds a cell surface molecule such as a cell surface receptor with a specificity described herein, such as an antibody, carbohydrate, peptide etc. or a binding fragment of any thereof. The binding domain can be from a member of a secretome, for example, a secreted protein or fragment of the secreted protein that is capable of binding to a cell surface entity such as a receptor. The binding domain can also be from a cleaved products or extracellular domains of membrane proteins, so long that they are capable of binding to a cell surface entity. The recombinant toxin fusion may further comprises a multimeric domain which allows multimerization of the fusion.

The term "receptor-ligand interaction" as used herein refers to any cell surface molecule (e.g. the "receptor") that can be specifically bound by another molecule (e.g. the "ligand"). Examples include a traditional cell surface receptor such as the EGFR and its cognate ligand EGF, as well as other moiety embedded, extending from or otherwise exposed on the cell surface of a cell that is used by the another molecule ligand to affect cell signaling and/or enter the cell.

The term "binding domain" as used herein means a moiety that interacts with a host cell surface molecule and facilitates its entry and the entry of fused cargo (i.e. the recombinant toxin) into the cell, and can be for example a receptor-binding molecule such as a ligand or a binding fragment thereof that binds a cognate receptor; a peptide or a binding fragment thereof that binds a receptor or positively charged phospholipids; an antibody or a binding fragment thereof that binds a cell surface protein; a carbohydrate that binds for example a lectin; a small molecule that interacts for example with a cell surface protein; or a lipid that interacts with a cell surface lipid binding protein. The binding domain may be a molecule such as an antibody or binding fragment that binds a receptor or interest, or a receptor binding molecule (e.g. a ligand) whose receptor is not known (e.g. an orphan ligand). For a receptor-binding molecule or a binding fragment thereof, a peptide or a binding fragment thereof, an antibody or a binding fragment thereof, a carbohydrate, a small molecule or a lipid to be a functional binding domain, it needs to bind to a host cell surface molecule and be internalized in at least one cell type. The receptor-binding molecule can be a growth factor, a cytokine, or a lysosomal enzyme. A growth factor refers to a molecule capable of stimulating cellular growth, proliferation, healing, and cellular differentiation. Some examples of growth factor include Epidermal Growth Factor (EGF), pleiotrophin (PTN), and Fibroblast Growth Factor (FGF). A cytokine refers to a category of small proteins, typically about 5 to 20 kDa that are important in cell signaling, which includes chemokines, interferons, interleukins, lymphokines, and tumour necrosis factors. Cytokines are involved in autocrine signaling, paracrine signaling and endocrine signaling as immunomodulating agents. An example of cytokine is chemokine (C-X-C motif) ligand 9 (CXCL9). A lysosomal enzyme is an enzyme that is found in the lysosome involving in cell processes including secretion, plasma membrane repair, cell signaling, and energy metabolism. In an embodiment, the receptor-binding molecule is or comprises a growth factor. For example, N-acetylglucosamine-6-sulfatase (GNS) or GM2 ganglioside activator (GM2A) are lysosomal enzymes. In an embodiment, the receptor-binding molecule comprises or is a growth factor, a cytokine, or a lysosomal enzyme. In an embodiment, the growth factor is EGF, PLN or FGF. In an embodiment, the receptor-binding molecule is or comprises a cytokine. In an embodiment, the cytokine is CXCL9. In an embodiment, the receptor-binding molecule is or comprises a lysosomal enzyme. In an embodiment, the lysosomal enzyme is N-acetylglucosamine-6-sulfatase (GNS) or GM2 ganglioside activator (GM2A). The affinity as measured in monovalent dissociation constant between the host cell surface molecule and said binding domain including receptor binding molecules, peptide, antibody or binding fragment thereof, carbohydrate, small molecule or lipid is below 50 μM, measured for example by ligand binding assay. A receptor-binding molecule (e.g. ligand) or binding fragment thereof, peptide, antibody or binding fragment thereof, carbohydrate, small molecule or lipid that is not capable of entering a cell is excluded as binding domain. "Small molecule" binding domains as used herein refer to a low molecular weight compound of less than 900 daltons, or less than 1,000 daltons.

The binding domain can be a molecule such as a ligand that binds a cell surface receptor of interest or an unknown cell surface receptor or other cell surface molecule. The binding domain specificity permits for screening for a receptor or a protein that associates with the binding domain. The present disclosure is not limited to conventional secreted proteins, as cleaved products or extracellular domains of membrane proteins can also be used.

The binding domain can be the binding domain or a binding fragment thereof of a naturally occurring toxin. For example, for Diphtheria toxin (DTA) the binding domain includes at least residues 1-193 (Uniprot accession Q5PY51_CORDP), for *Pseudomonas* exotoxin A (PE) the binding domain includes at least residues 405-638 (TOXA_PSEAE), for saporin the binding domain includes at least residues 22-277 (RIP6_SAPOF), for gelonin the binding domain includes at least residues 47-297 (RIPG_SURMU), for perfringolysin the binding domain includes at least residues 29-500 (TACY_CLOPE), for listeriolysin the binding domain includes at least residues 26-529 (TACY_LISMO), for α-hemolysin the binding domain includes at least residues 27-319 (HLA_STAAU), for subtilase cytotoxin the binding domain includes at least residues 22-347 (SUBA_ECOLX), for bouganin the binding domain includes at least residues 1-305 (Q8W4U4_9 CARY), and for ricin the binding domain includes at least residues 36-302 (RICI_RICCO). Such binding domains can be used for example in methods disclosed herein, to identify "background" hits that provide resistance to the particular toxin domain.

The term "toxin domain" as used herein means the minimal domain of a toxin that imparts toxicity when internalized in a cell. For example for Diphtheria toxin (DTA) the toxin domain includes at least residues 1-193 (Uniprot accession Q5PY51_CORDP), for *Pseudomonas* exotoxin A (PE) the toxin domain includes at least residues 405-638 (TOXA_PSEAE), for saporin the toxin domain includes at least residues 22-277 (RIP6_SAPOF), for gelonin the toxin domain includes at least residues 47-297 (RIPG_SURMU), for perfringolysin the toxin domain includes at least residues 29-500 (TACY_CLOPE), for listeriolysin the toxin domain includes at least residues 26-529 (TACY_LISMO), for α-hemolysin the toxin domain includes at least residues 27-319 (HLA_STAAU), for subtilase cytotoxin the toxin domain includes at least residues 22-347 (SUBA_ECOLX), for bouganin the toxin domain includes at least residues 1-305 (Q8W4U4_9 CARY), and for ricin the toxin domain includes at least residues 36-302 (RICI_RICCO). Some toxins only have the toxin domain (e.g. saporin), others have a toxin domain and a binding domain (e.g. α-hemolysin). Some others have a toxin domain, a binding domain and a translocation domain (e.g. Diphtheria toxin).

The term "translocation domain" as used herein refers to the minimal domain of a toxin or other molecule that provides transmembrane passage of the toxin and any fused cargo from an endosome into the cytosol. The translocation domain can be naturally occurring in a toxin or from another toxin in a recombinant toxin fusion, or a transmembrane passage forming fragment thereof. For Diphtheria toxin (DTA) the translocation domain includes at least residues 201-380 (Uniprot accession Q5PY51_CORDP), for *Pseudomonas* exotoxin A (PE) the translocation domain includes at least residues 278-389 (TOXA_PSEAE). In a recombinant toxin fusion, the translocation of the recombinant toxin fusion from endosomes to the cytoplasm can be facilitated by the translocation domain. In an embodiment, the translocation domain is or comprises DTA or PE translocation domain, or a transmembrane passage forming fragment thereof. Some toxins do not contain separate or specific translocation domains or receptor-binding molecules as these domains are embedded in a single domain. For example, saporin is a ribosome-inactivating toxin that does not have a translocating domain. As well, subtilase cytotoxin (SubAB) does not have to translocate to the cytoplasm since its target BiP chaperone resides in the endoplasmic reticulum.

The term "multimerization domain" as used herein refers to the minimal domain for multimerization of a toxin or molecule. Multimerization of a recombinant toxin fusion, for example, enhances the biological and/or binding activity of the fusion. This domain is readily recognized by the person skilled in the art, which includes, for example, cytoplasmic domain of syndecan-4, or a coiled coil domain, for example from GCN4 transcription factor or cartilage oligomeric matrix protein (COMP), which may form a dimer, timer, tetramer, pentamer, hexamer, heptamer, octamer, nanomer, and decamer, etc. For instance, multimerization involves, for example, pentamerization domain that is used in extracellular screens. The pentamerization domain can bring multiple toxin fusions together and increase avidity for the receptor.

The term "vector" as used herein comprises any intermediary vehicle for a nucleic acid molecule which enables said nucleic acid molecule, for example, to be introduced into prokaryotic and/or eukaryotic cells and/or integrated into a genome, and include plasmids, phagemids, bacteriophages or viral vectors such as retroviral based vectors, Adeno Associated viral vectors and the like. The term "plasmid" as used herein generally refers to a construct of extrachromosomal genetic material, usually a circular DNA duplex, which can replicate independently of chromosomal DNA.

The nucleic acid molecule or fragments thereof may be used to regulate expression of a gene. Silencing using a nucleic acid molecule of the present disclosure may be accomplished in a number of ways generally known in the art, for example, RNA interference techniques using shRNA or siRNA, microRNA (miRNA) techniques, CRISPR-Cas or CRISPR-Cpf1 system using gRNA and targeted mutagenesis techniques.

The term "CRISPR-Cas", "CRISPR system", or "CRISPR-Cas System" as used herein refers collectively to transcripts and other elements involved in the expression of or directing the activity of CRISPR-associated ("Cas") genes, including nucleic acids encoding a Cas gene, a tracr (trans-activating CRISPR) sequence (e.g. an active partial tracrRNA), a tracr-mate sequence (comprising a "direct repeat" and a tracrRNA-processed partial direct repeat in the context of an endogenous CRISPR system), a guide sequence (gRNA, e.g. RNA to guide Cas, such as Cas9; CRISPR RNA and transactivating (tracer) RNA or a single guide RNA (sgRNA)) or other sequences and transcripts from a CRISPR locus. The CRISPR-Cas is optionally a class II monomeric Cas protein for example a type II Cas, or a type V Cas. The type II Cas protein may be a Cas9 protein, such as Cas9 from *Streptococcus pyogenes, Francisella novicida, A. Naesulndii, Staphylococcus aureus* or *Neisseria meningitidis*. Optionally the Cas9 is from *S. pyogenes*. The type V Cas protein may possess RNA processing activity.

The type V Cas protein may be a Cas12a (also known as Cpf1) Cas protein, such as a Cas12a from Lachnospiraceae bacterium (Lb-Cas12a) or from *Acidaminococcus* sp. BV3L6 (As-Cas12a). The terms "Cpf1" and "Cas12a" are used interchangeably throughout. As such, a CRISPR system can also be a CRISPR-Cpf1 system, in which Cas such as Cas9 is substituted by Cpf1. A CRISPR system is typically characterized by elements that promote the formation of a CRISPR complex at the site of a target sequence.

The terms "gRNA" or "guide RNA" as used herein refer to an RNA molecule that hybridizes with a specific DNA sequence (e.g. a crRNA) and further comprises a protein binding segment that binds a CRISPR-Cas protein that is referred to as the tracrRNA. The gRNA can also include direct repeats. The portion of the guide RNA that hybridizes with a specific DNA sequence is referred to herein as the nucleic acid-targeting sequence, or crRNA or spacer sequence. The gRNA can also refer to or be represented by the corresponding DNA sequence that encodes the gRNA as would be understood from the context. As the target specific portion or crRNA can be combined with different tracrRNAs, guide sequences provided herein include minimally the crRNA sequence.

The term "crRNA" also referred to as the "spacer sequence" or comprising the spacer sequence as used herein refers to the portion of the gRNA that forms, or is capable of forming, an RNA-DNA duplex with the target sequence. The sequence may be complementary or correspond to a specific CRISPR target sequence. The nucleotide sequence of the crRNA/spacer sequence may determine the CRISPR target sequence and may be designed to target a desired CRISPR target site. The crRNA can also refer to or be represented by the corresponding DNA sequence that encodes the crRNA as would be understood from the context.

The term "CRISPR target site" or "CRISPR-Cas target site" as used herein means a nucleic acid to which an activated CRISPR-Cas protein will bind under suitable conditions. A CRISPR target site comprises a protospacer-adjacent motif (PAM) and a CRISPR target sequence (i.e. corresponding to the crRNA/spacer sequence of the gRNA to which the activated CRISPR-Cas protein is bound). The sequence and relative position of the PAM with respect to the CRISPR target sequence will depend on the type of CRISPR-Cas protein. For example, the CRISPR target site of type II CRISPR-Cas protein such as Cas9 may comprise, from 5' to 3', a 20 nucleotide target sequence followed by a 3 nucleotide PAM having the sequence NGG (SEQ ID NO:6). Accordingly, a type II CRISPR target site may have the sequence 5'-n1-n2-n3-n4-n5-n6-n7-n8-n9-n10-n11-n12-n13-n14-n15-n16-n17-n18-n19-n20-NGG-3' (SEQ ID NO:7). As another example, the CRISPR-target site of a type V CRISPR-Cas protein such as Cpf1 may comprise, from 5' to 3', a 4 nucleotide PAM having the sequence TTTV (SEQ ID NO:8; where V is A, C, or G), followed by a 23 nucleotide target sequence. Accordingly, a type V CRISPR target site may have the sequence 5'-TTTV—n1-n2-n3-n4-n5-n6-n7-n8-n9-n10-n11-n12-n13-n14-n15-n16-n17-n18-n19-n20-n21-n22-n23-3' (SEQ ID NO:9).

The skilled person will understand that for binding a CRISPR target site, the DNA containing the CRISPR target site will be accessible to the CRISPR-Cas protein. Accordingly, the CRISPR-Cas protein may comprise for example one or more a nuclear localization signals, optionally a nucleoplasmin nuclear localization signal.

The term "tracrRNA" also "trans-encoded crRNA" as used herein is a RNA which may, for example, interact with a CRISPR-Cas protein such as Cas9 and may be connected to, or form part of, a gRNA. The tracrRNA may be a tracrRNA from for example *S. pyogenes*. A tracrRNA may have for example the sequence of 5'-gtttcagagctatgctg-gaaacagcatagcaagttgaaataaggctagtccgttatcaactt-gaaaaagtggcaccgagtcggtgc-3' (SEQ ID NO:10). Other tracrRNAs may also be used. The trRNA can also refer to or be represented by the corresponding DNA sequence that encodes the trRNA as would be understood from the context.

The terms "direct repeat" as used herein refers to an RNA that forms a stem-loop and may, for example, interact with a CRISPR-Cas protein such as Cpf1 and may be connected to, or form part of, a guide RNA. The direct repeat may be a direct repeat from for example Lachnospiraceae bacterium or *Acidaminococcus* sp. BV3L6. A direct repeat may have for example the sequence of 5'-taatttctactcttgtagat-3' (for Lb-Cpf1) (SEQ ID NO:11) or 5'-taatttctactaagtgtagat-3' (for As-Cpf1) (SEQ ID NO:12). Other direct repeats may also be used. The direct repeats can also refer to or be represented by the corresponding DNA sequence that encodes the direct repeats as would be understood from the context.

The term "targeting library" as used herein refers to a collection or a plurality of nucleic acid molecules that targets and downregulates (e.g. silences, inhibits or reduces) expression of a set of genes which can for example be used for identifying (e.g. screening) genes related to a phenotype of interest. The targeting library can be broadly based or focused (also referred to as a defined library). A whole genome library is a broadly based targeting library that contains nucleic acid molecules which target all or nearly all the genes, for example, at least 85%, 90%, 95%, 96%, 97%, 98%, or 99%, of the genome of a single organism. A focused library can be a library that comprises nucleic acids that target a plurality of genes related to all or nearly all pathways involved in a category or field of interest. For example, a targeting library can contain nucleic acid molecules related to all or nearly all pathways associated with a category of genes such as cell surface receptor genes, where being associated means for example factors required for receptor surface expression and functionalization, such as genes involved in receptor biogenesis, maturation, or trafficking and factors involved in ligand and/or receptor endocytosis. A focused library may for example include targeting genes that encode proteins which are localized to the plasma membrane, ER membrane and other intracellular membranes; trafficking factors regulating endocytosis and receptor maturation; transcription factors regulating the expression of cell surface proteins or any proteins for that matter.

Each of the nucleic acid molecules in the whole genome library targets a specific gene of the organism. The targeting of a specific gene refers to targeting gene expression. Where the targeting uses gRNA, siRNA, shRNA or miRNA, the nucleic acid molecule express a nucleic acid sequence that includes a portion that is complementary to a portion of the targeted gene. Multiple nucleic acid molecules can target the same gene. Suitable targeting libraries include gRNA whole genome libraries and focused libraries available from Addgene and Toronto Knockout Library (www.addgene.org/crispr/libraries and tko.ccbr.utoronto.ca). As shown in the Examples, targeting libraries such as the TKOV3 library can be used.

The phrase "a population of engineered cells comprising a targeting library" means as used herein a population of cells that has been transduced, electroporated or otherwise manipulated so that different components of the library are comprised and expressed in different cells of the population.

In an embodiment, the targeting library is a whole genome library. In another embodiment, the targeting library comprises nucleic acid molecules targeting cell surface receptor genes, preferably GPCRs. In an embodiment, the targeting library comprises nucleic acid molecules targeting genes encoding cell surface receptor-mediated pathways. In an embodiment, the targeting library comprises nucleic acid molecules targeting at least one of trafficking factors regulating endocytosis and receptor maturation factor genes. In an embodiment, the targeting library comprises nucleic acid molecules targeting receptor maturation factor genes. In an embodiment, the targeting library comprises nucleic acid molecules targeting proteins localized to the plasma membrane, ER membrane and other intracellular membranes. In an embodiment, the targeting library comprises nucleic acid molecules targeting transcription factors regulation expression of protein, optionally expression of cell surface proteins.

B. Methods

Figure 3:
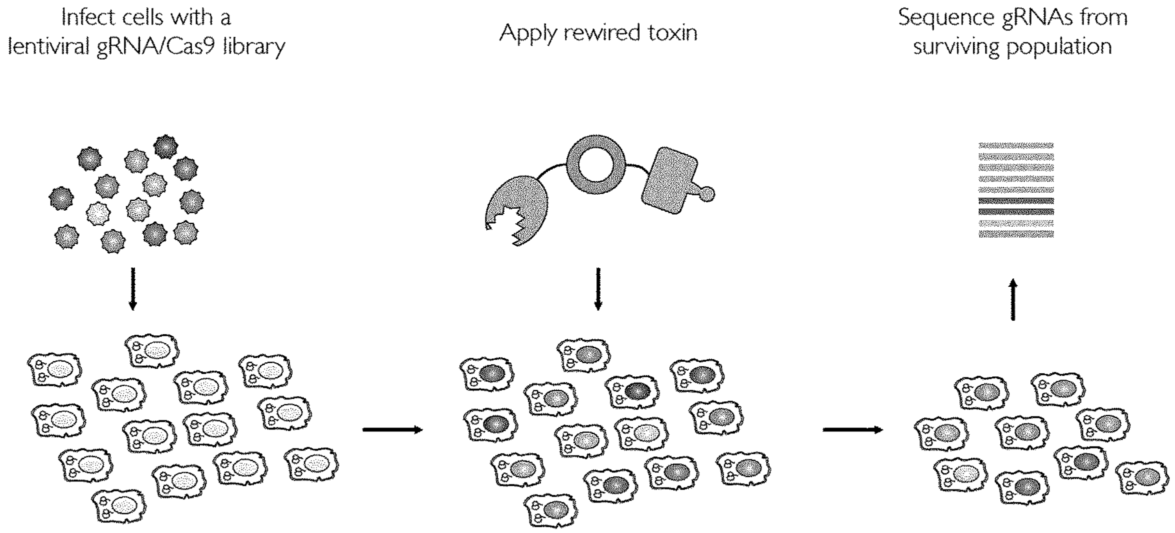
FIG. 3 shows a schematic diagram of identifying toxin receptors with Clustered Regularly Interspaced Short Palindromic Repeats (CRISPR) screening.

As described herein, the inventors have determined methods and components for genome-wide genetic screens such as the CRISPR/Cas9-based positive genetic screen described herein. The inventors have demonstrated that infecting cells with a genome-wide gRNA library followed by recombinant toxin fusion treatment allows the identification of rare resistant cells. Sequencing of gRNAs from resistant cells can identify the cognate receptor and factors required for receptor surface expression and functionalization (FIG. 3).

Described herein in one aspect are methods for identifying a protein associated with a receptor-ligand interaction in a screen.

Accordingly, an aspect of the disclosure provides a method for identifying a protein associated with a receptor-ligand interaction, comprising the steps of:

(a) providing a population of engineered cells comprising a targeting library, wherein an individual engineered cell of the population contains a nucleic acid molecule of the targeting library, and wherein the nucleic acid molecule comprises a nucleic acid sequence complementary to a target gene;

(b) contacting the population of cells for sufficient time with a recombinant toxin fusion comprising a toxin domain, a binding domain and optionally a translocation domain, thereby producing a selection pool of cells; and (c) sequencing one or more of the nucleic acid molecule comprised in the selection pool of cells, thereby identifying the target gene.

Some embodiments include a control screen where the population of cells are contacted with a toxin for sufficient time, optionally at least 0.1 nM toxin for at least 2 days. Some embodiments include performing a control screen where the binding domain is the binding domain corresponding to the toxin domain (e.g. both the toxin domain and the binding domain are from DT). For example, in a control screen, some genes identified in (c) above can be genes required for intoxication by a toxin and serve as control genes in subsequent screens, as these genes regulate intoxication independently of the specificity of the binding domain (e.g. when the binding domain is for a desired target such as an orphan ligand). For example, as shown in Example 1, FURIN, MESDC2, DPH1, DPH2, DPH3, DPH5, DPH7, and DNAJC24 have been identified as required genes for *Pseudomonas* exotoxin A (PE)-mediated toxicity, and DPH1, DPH2, DPH3, DPH5, DPH7, and DNAJC24 have been identified as required genes for Diphtheria toxin (DTA)-mediated toxicity. Accordingly, in some embodiments, a control or background screen is done to identify genes that that are required for intoxication by a toxin and/or which are general toxin resistance genes not related to the pathway engaged by the binding domain protein and which can serve as controls. Genes of interest screens use recombinant toxin fusions comprising a selected binding domain which is different from the binding domain in the control screen in that the binding domain of the recombinant toxin fusions is replaced by a targeting moiety for identifying genes of interest (e.g. replaced by a ligand for identifying its cognate receptor). Genes identified in genes of interest screens may contain the control genes as well as the genes of interest. For identifying the genes of interest, a comparison is carried out by which control genes are identified and subtracted from the genes identified by the recombinant toxin fusion in a genes of interest screen. In some embodiments, identifying genes of interest comprises comparing control genes identified in a control screen with a toxin and genes identified by a recombinant toxin fusion in a genes of interest screen, wherein binding specificity of the binding domain of the recombinant toxin fusion in a genes of interest screen is different from binding specificity of the binding domain of the toxin in a control screen. In some embodiments, a toxin in a control screen is different from a recombinant toxin fusion in a genes of interest screen, wherein the binding domain of the toxin in the control screen is replaced in a genes of interest screen by a different binding domain comprised in the recombinant toxin fusion.

The targeting library can have nucleic acid molecules including gRNA, siRNA, shRNA or miRNA. In an embodiment, the nucleic acid molecule targeting specific gene expression comprises a gRNA, siRNA, shRNA or miRNA, preferably a gRNA. In another embodiment, the CRISPR-Cas system comprises Cas9.

The targeting library can target genes in a species of interest, including "mammalian library" which is a screening library for genes in a species of mammal. In another embodiment, the targeting library is a mammalian library, preferably a human or mouse library. A "targeted gene" or derivative thereof refers to a gene which expression is being downregulated by a mechanism described herein through the introduction into a cell of a nucleic acid molecule having a nucleic acid sequence that is complementary to a part of the target gene.

The targeting library can be broadly based or focused. In an embodiment, the targeting library is a whole genome library. In another embodiment, the targeting library comprises nucleic acid molecules targeting cell surface receptor genes, preferably GPCR genes. In an embodiment, the targeting library comprises nucleic acid molecules targeting genes encoding proteins of cell surface receptor-mediated pathways. In an embodiment, the targeting library comprises nucleic acid molecules targeting receptor maturation factor genes.

In an embodiment, the population of cells comprises cells from a mammalian cell line, preferably a human or mouse cell line. In another embodiment, the mammalian cell line is A431, A549, HCT116, K562, HeLa, preferably HeLa-Kyoto, or HEK-293, preferably HEK-293T, or a haploid or near haploid cell line, preferably HAP1. The skilled person can readily recognize alternative cell lines suitable for identifying a protein associated a receptor-ligand interaction.

The targeting library can be introduced into the population of cells of a cell line by a number of methods. One method is transduction using viral vectors, such as retroviral based vectors, Adeno Associated viral vectors and the like. In an embodiment, the targeting library is transduced into the cells with at least one retroviral vector, preferably at least one lentiviral vector. In an embodiment, the transduced cells are maintained for 2 to 10 days, or at least 2, 3, 4, 5, 6, 7, or 8 days, or at most 3, 4, 5, 6, 7, 8, 9, or 10 days, prior to treatment with a toxin. In an embodiment, the transduced cells are contacted with a toxin for 1 to 5 days, or at least 1, 2, 3, or 4, or at most 2, 3, 4, or 5 days.

The presently described methods use recombinant toxin fusions as agents for screening for protein associated with a receptor-ligand interaction in a pool of cells. The recombinant toxin fusion comprises a toxin domain, a binding domain, and optionally a translocation domain.

Diphtheria toxin (DTA) and *Pseudomonas* exotoxin A (PE) are bacterial exotoxins that are toxic to cells, in particular mammalian cells, with picomolar potency. The toxin domain of these toxins potently inhibits protein synthesis, leading to rapid cell death. For DTA, the toxin domain is the catalytic domain known as the C domain which has an unusual beta+alpha fold. The C domain blocks protein synthesis by transfer of ADP-ribose from NAD to a diphthamide residue of eukaryotic elongation factor 2 (eEF-2). Protein synthesis inhibition by PE follows a similar mechanism. In an embodiment, the recombinant toxin fusion comprises Diphtheria toxin (DTA) or *Pseudomonas* exotoxin A (PE) toxin domain, or a toxic fragment thereof. In another embodiment, the toxin domain is at the amino or carboxyl terminus of the recombinant toxin fusion. A recombination toxin fusion can be expressed from pcDNA3.1-SP-DTA-GS-ccdB (SEQ ID NO:1), pET15b-SHT-SUMO-DTA-ccdB (SEQ ID NO:2), pcDNA3.1-SP-codB-GSlinker-PE40 (SEQ ID NO:3), pET15b-SHT-ccd-PE40 (SEQ ID NO:4), or pcDNA3.1-ccdB-PE38-6×His (SEQ ID NO:5) that has a nucleic acid sequence encoding a ligand cloned in between the two attR sites.

In a recombinant toxin fusion, the binding domain provides the "optionality" for screening for receptor or proteins associated with a ligand-receptor interaction. The binding domain can be or comprise any molecule by which the cognate receptor or proteins associated with the ligand-receptor interaction are to be identified. The molecule can be a receptor-binding molecule or a binding fragment thereof, a peptide or a binding fragment thereof, an antibody or a binding fragment thereof, a carbohydrate, a small molecule, or a lipid. In an embodiment, the binding domain is a receptor-binding molecule of a desired molecule or a binding fragment thereof, a peptide, an antibody or a binding fragment thereof, a carbohydrate, a small molecule, or a lipid.

In some embodiments, the binding domain is conjugated directly to the toxin domain and/or the translocation domain. In other embodiments, a linker is used for one or more of these conjugations. Any linker can be used. For example, a glycine-serine rich linker increases flexibility. In some embodiments, the linker is a glycine-serine rich linker. Examples of suitable linkers are provided in the Examples.

In another embodiment, the receptor-binding molecule is or comprises a ligand or a binding fragment thereof, optionally an orphan ligand, or a binding fragment thereof. In another embodiment, the receptor-binding molecule is or comprises EGF (Accession number NM_001963), PTN (Accession number NM_002825), CXCL9 (Accession number NM_002416), GNS (Accession number P15586), GM2A (Accession number P17900), FGF2 (Accession number P09038), or a binding fragment thereof. In another embodiment, the peptide is or comprises a TAT peptide, Aβ40 or Aβ42, or a binding fragment thereof.

The binding domain or the binding fragment thereof can have undergone post-translational modifications which can affect its binding to receptor. Post-translational modifications that can have effect on binding includes phosphorylation, acetylation, glycosylation, amidation, hydroxylation, methylation, ubiquitylation, or mannose-6-phosphate addition. Phosphorylation refers to the attachment of a phosphoryl group to a molecule. When the molecule is a protein, phosphorylation typically occurs at serine, threonine and tyrosine. Acetylation refers to the introduction of an acetyl group to a molecule. Glycosylation refers to the addition of a carbohydrate, e.g. a glycosyl donor, to a molecule, for example, by enzymatic process that attaches glycans to proteins or lipids. Common glycosylation includes N-linked glycosylation and O-linked glycosylation. N-linked glycosylation typically requires dolichol phosphate and it involves N-linked glycans attached to a nitrogen of asparagine or arginine side-chains. In O-linked glycosylation, glycans are attached to the hydroxyl oxygen of serine, threonine, tyrosine, hydroxylysine, or hydroxyproline side-chains, or to oxygen on lipids such as ceramide. Amidation refers to the addition of an amide to a molecule, for example, where a peptide has amidation at their C-terminal. The amino acid to be modified is typically followed by a glycine, which provides the amide group. For example, the glycine is oxidized to form alpha-hydroxy-glycine, and the oxidized glycine cleaves into the C-terminally amidated peptide and an N-glyoxylated peptide. Hydroxylation is an oxidative process which refers to the introduction of a hydroxyl group to a molecule. Hydroxylases are enzymes that are capable of catalyzing hydroxylation reactions. Methylation refers to the addition of a methyl group to a molecule. In cells, methylation is accomplished by enzymes, and where the substrate of methylation is a protein, it typically takes place on arginine or lysine amino acid residues in the protein sequence. Ubiquitylation is addition of ubiquitin to a molecule. Where the molecule is a protein, the ubiquitylation can be a single ubiquitin protein (i.e. monoubiquitylation) or a chain of ubiquitin polyubiquitylation). Mannose-6-phosphate is a targeting signal for proteins that are destined for transport to lysosomes. The addition of mannose-6-phosphate to a protein typically occurs in the cis-Golgi apparatus, and is usually referred to as tagging, i.e. the mannose-6-phosphate on the modified protein is referred to as a mannose-6-phosphate tag. For example, in a reaction involving uridine diphosphate (UDP) and N-acetylglucosamine, the enzyme N-acetylglucosamine-1-phosphate transferase catalyzes N-linked glycosylation of asparagine residues with mannose-6-phosphate. The mannose-6-phosphate tagged proteins are moved to trans-Golgi, where the mannose-6-phosphate tag can be recognized and bound by mannose 6-phosphate receptor (MPR) proteins. In an embodiment, the binding domain comprises a post-translational modification. In another embodiment, the post-translational modification is or comprises phosphorylation, acetylation, glycosylation, amidation, hydroxylation, methylation, ubiquitylation, or mannose-6-phosphate addition. In another embodiment, the post-translational modification is or comprises mannose-6-phosphate addition.

In another embodiment, the recombinant toxin fusion when administered to cells kills at least about 99%, 99.5%, 99.9% or 100% of engineered cells. In another embodiment, the recombinant toxin fusion when administered to cells inhibits growth of cells at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9% or 100% of engineered cells.

The identities of proteins associated with a receptor-ligand interaction from the presently described methods are determined by sequencing one or more of the nucleic acid molecules targeting specific gene expression comprised in the selection pool of cells. In an embodiment, the sequencing comprises high-throughput sequencing. A number of genes have been identified by the present disclosure as being essential for enabling the toxic effects of toxins. For example, the downregulation or silencing of DPH1 (Accession number NM_001383), DPH2 (Accession number NM_001384), DPH3 (Accession number NM_206831), DPH5 (Accession number NM_001077394), DPH7 (Accession number NM_138778), or DNAJC24 (Accession number NM_181706) renders HEK-293T cells resistant to DTA or PE.

Also provided is specifically a method of producing a toxin-resistant cell line, comprising the steps of:

(a) introducing into cells of a selected cell line and expressing at least one nucleic acid molecule comprising a nucleic acid sequence encoding Cas or Cpf1, and a nucleic acid sequence encoding at least one gRNA targeting DPH1, DPH2, DPH3, DPH5, DPH7, or DNAJC24, preferably DNAJC24; and
(b) contacting the cells with a toxin for sufficient time to produce the toxin-resistant cell line, optionally at least 0.1 nM toxin for at least 2 days.

In an embodiment, the cells were contacted with between about 0.1 nM and 100 nM toxin. In an embodiment, the cells were contacted with toxin for 1 to 4 days, or 2, 3, or 4 days. In an embodiment, the cells were contact with between about 0.1 nM toxin and 100 nM toxin for at least 2, 3, 4, or 5 days, up to 6, 7, 8, 9, 10, 11, 12, 13, or 14 days.

In an embodiment, the method involves the toxin DTA or PE. In another embodiment, the Cas of the method is Cas9. In another embodiment, the cell line of the method is HEK-293, preferably HEK-293T.

For DTA-resistance, in addition to downregulation or silencing of DPH1, DPH2, DPH3, DPH5, DPH7, or DNAJC24, the downregulation or silencing of HBEGF also renders HEK-293T cells resistant to DTA.

Accordingly, also provided is specifically a method of producing a Diphtheria toxin (DTA)-resistant cell line, comprising the steps of:

(a) introducing into cells of a selected cell line and expressing at least one nucleic acid molecule comprising a nucleic acid sequence encoding Cas or Cpf1, and a nucleic acid sequence encoding at least one gRNA targeting HBEGF, DPH1, DPH2, DPH3, DPH5, DPH7, or DNAJC24, preferably DNAJC24; and
(b) contacting the cells with DTA for sufficient time to produce the DTA-resistant cell line, optionally at least 0.1 nM DTA for at least 2 days.

In an embodiment, the Cas in the method of producing a DTA-resistant cell line is Cas9. In another embodiment, the DTA-resistant cell line is HEK-293, preferably HEK-293T. In an embodiment, the cells were contacted with between about 0.1 nM and 100 nM DTA. In an embodiment, the cells were contacted with DTA for 1 to 4 days, or 2, 3, or 4 days. In an embodiment, the cells were contact with between about 0.1 nM DTA and 100 nM DTA for at least 2, 3, 4, or 5 days, up to 6, 7, 8, 9, 10, 11, 12, 13, or 14 days.

For PE-resistance, in addition to downregulation or silencing of DPH1, DPH2, DPH3, DPH5, DPH7, or DNAJC24, the downregulation or silencing of FURIN (Accession number NM_002569), MESDC2 or LRP1 (Accession number NM_002332) also renders HEK-293T cells resistant to PE.

Accordingly, also provided is a method of producing a PE-resistant cell line, comprising the steps of:

(a) introducing into cells of a selected cell line and expressing at least one nucleic acid molecule comprising a nucleic acid sequence encoding Cas or Cpf1, and a nucleic acid sequence encoding at least one gRNA targeting FURIN, MESDC2, LRP1, LRP1B, DPH1, DPH2, DPH3, DPH5, DPH7, or DNAJC24, preferably DNAJC24; and
(b) contacting the cells with PE for sufficient time to produce the PE-resistant cell line, optionally at least 0.1 nM PE for at least 2 days.

In an embodiment, the cells were contacted with between about 0.1 nM and 100 nM PE. In an embodiment, the cells were contacted with 12 nM PE. In an embodiment, the cells were contacted with PE for 1 to 4 days, or 2, 3, or 4 days. In an embodiment, the cells were contact with between about 0.1 nM PE and 100 nM PE for at least 2, 3, 4, or 5 days, up to 6, 7, 8, 9, 10, 11, 12, 13, or 14 days. In an embodiment, the cells were contact with 0.1 nM PE for at least 2 days. In a specific embodiment, the cells were contacted with 12 nM PE for 2 days.

In an embodiment, the Cas in the method of producing a PE-resistant cell line is Cas9. In another embodiment, the PE-resistant cell line is HEK-293, preferably HEK-293T.

For subtilase cytotoxin-resistance, the downregulation or silencing of SLC35A1 (Accession numbers NM_001168398 and NM_006416), SLC35A2 (Accession numbers NM_001032289, NM_001042498, NM_001282647, NM_001282648, NM_001282649, NM_001282650, NM_001282651, and NM_005660), CMAS (Accession number NM_018686) or conserved oligomeric golgi (COG) complex which includes COG1 (Accession number NM_018714), COG2 (Accession numbers NM_001145036 and NM_007357), COG3 (Accession number NM_031431), COG4 (Accession numbers NM_001195139, NM_001365426, and NM_015386), COG5 (Accession numbers NM_001161520, NM_006348, and NM_181733), COG6 (Accession numbers NM_001145079 and NM_020751), COG7 (Accession number NM_153603), COG8 (Accession number NM_032382), renders HEK-293T cells resistant to subtilase cytotoxin.

Accordingly, also provided is a method of producing a subtilase cytotoxin-resistant cell line, comprising the steps of:

(a) introducing into cells of a selected cell line and expressing at least one nucleic acid molecule comprising a nucleic acid sequence encoding Cas or Cpf1, and a nucleic acid sequence encoding at least one gRNA targeting SLC35A1, SLC35A2, CMAS, COG1, COG2, COG3, COG4, COG5, COG6, COG7 or COG81; and
(b) contacting the cells with subtilase cytotoxin for sufficient time to produce the subtilase cytotoxin-resistant cell line, optionally at least 0.1 nM subtilase cytotoxin for at least 2 days.

In an embodiment, the cells were contacted with between about 0.1 nM and 100 nM subtilase cytotoxin. In an embodiment, the cells were contacted with subtilase cytotoxin for 1 to 4 days, or 2, 3, or 4 days. In an embodiment, the cells were contact with between about 0.1 nM subtilase cytotoxin and 100 nM subtilase cytotoxin for at least 2, 3, 4, or 5 days, up to 6, 7, 8, 9, 10, 11, 12, 13, or 14 days.

For a cell line to be able to produce a toxin or a recombinant toxin fusion, the cell line needs to be resistant to the toxin or the recombinant toxin fusion as well as encompassing the genetic material for producing the toxin or the recombinant toxin fusion.

Accordingly, also provided is a method of producing a toxin-producing cell line, comprising the steps of:

(a) introducing into cells of a selected cell line and expressing at least one nucleic acid molecule comprising a nucleic acid sequence encoding Cas or Cpf1, and a nucleic acid sequence encoding at least one gRNA targeting DPH1, DPH2, DPH3, DPH5, DPH7, or DNAJC24, preferably DNAJC24;
(b) contacting the cells with a toxin for sufficient time, optionally at least 0.1 nM toxin for at least 2 days; and
(c) introducing into the cells of step (b) and expressing a nucleic acid molecule comprising a nucleic acid sequence encoding the toxin or a recombinant toxin fusion.

In an embodiment, the toxin of (b) or (c) is Diphtheria toxin (DTA) or *Pseudomonas* exotoxin A (PE). In another embodiment, the recombinant toxin fusion of (c) comprises a toxin domain, a binding domain, and optionally a translocation domain. In another embodiment, the toxin domain is at the amino or carboxyl terminus of the recombinant toxin fusion. In another embodiment, the binding domain is at an opposite terminus of the toxin domain. In another embodiment, the binding domain is or comprises a receptor-binding molecule or a binding fragment thereof, a peptide or a binding fragment thereof, an antibody or a binding fragment thereof, a carbohydrate, a small molecule, or a lipid. In another embodiment, the toxin domain is or comprises DTA or PE toxin domain, or a toxic fragment thereof. In another embodiment, the receptor-binding molecule is or comprises a ligand, or a binding fragment thereof, optionally an orphan ligand, or a binding fragment thereof. In another embodiment, the receptor-binding molecule is or comprises EGF, PTN, CXCL9, GNS, GM2A or FGF, or a binding fragment thereof. In another embodiment, the peptide is or comprises a TAT peptide, Aβ40 or Aβ42, or a binding fragment thereof. In another embodiment, the binding domain comprises a post-translational modification. In another embodiment, the post-translational modification is or comprises phosphorylation, acetylation, glycosylation, amidation, hydroxylation, methylation, ubiquitylation, or mannose-6-phosphate addition. In another embodiment, the post-translational modification is or comprises mannose-6-phosphate addition. In another embodiment, the translocation domain is or comprises DTA or PE translocation domain, or a transmembrane passage forming fragment thereof. In another embodiment, the Cas is Cas9. In another embodiment, the cell line is HEK-293, preferably HEK-293T.

A toxin-producing cell line allows for production of the toxin. Also provided is a method of producing a toxin, comprising the steps of:

(a) introducing into cells of a selected cell line and expressing at least one nucleic acid molecule comprising a nucleic acid sequence encoding Cas or Cpf1, and a nucleic acid sequence encoding at least one gRNA targeting DPH1, DPH2, DPH3, DPH5, DPH7, or DNAJC24, preferably DNAJC24;
(b) contacting the cells with a toxin for sufficient time;
(c) introducing into the cells of step (b) and expressing a nucleic acid molecule comprising a nucleic acid sequence encoding the toxin or a recombinant toxin fusion;
(d) growing the cell in media; and
(e) collecting the media containing the toxin or the recombinant toxin fusion.

In an embodiment, the method of producing a toxin produces Diphtheria toxin (DTA) or *Pseudomonas* exotoxin A (PE). In another embodiment, the method produces a recombinant toxin fusion comprising a toxin domain, a binding domain, and optionally a translocation domain. In another embodiment, the toxin domain is at the amino or carboxyl terminus of the recombinant toxin fusion. In another embodiment, the binding domain is at an opposite terminus of the toxin domain. In another embodiment, the binding domain is or comprises a receptor-binding molecule or a binding fragment thereof, a peptide or a binding fragment thereof, an antibody or a binding fragment thereof, a carbohydrate, a small molecule, or a lipid. In another embodiment, the toxin or toxin domain is or comprises DTA or PE toxin domain, or a toxic fragment thereof. In another embodiment, the receptor-binding molecule is or comprises a ligand, or a binding fragment thereof, optionally an orphan ligand, or a binding fragment thereof. In another embodiment, the receptor-binding molecule is or comprises EGF, PTN, CXCL9, GNS, GM2A or FGF, or a binding fragment thereof. In another embodiment, the peptide is or comprises a TAT peptide, Aβ40 or Aβ42, or a binding fragment thereof. In another embodiment, the binding domain comprises a post-translational modification. In another embodiment, the post-translational modification is or comprises phosphorylation, acetylation, glycosylation, amidation, hydroxylation, methylation, ubiquitylation, or mannose-6-phosphate addition. In another embodiment, the post-translational modification is or comprises mannose-6-phosphate addition. In another embodiment, the translocation domain is or comprises DTA or PE translocation domain, or a transmembrane passage forming fragment thereof. In another embodiment, the Cas is Cas9. In another embodiment, the cell line is HEK-293, preferably HEK-293T.

A toxin can also be produced by a cell such as a bacterial, insect or yeast cell. Also provided is a method of producing a toxin in a cell such as a bacterial, insect or yeast cell, comprising the steps of:

(a) introducing into the cell and expressing a nucleic acid molecule comprising a nucleic acid sequence encoding the toxin or a recombinant toxin fusion;
(b) growing the cell in media; and
(c) collecting the media containing the toxin or the recombinant toxin fusion.

In an embodiment, the toxin of (a) is Diphtheria toxin (DTA), *Pseudomonas* exotoxin A (PE), saporin, gelonin, perfringolysin, listeriolysin, α-hemolysin, subtilase cytotoxin, bouganin, or ricin. In another embodiment, the recombinant toxin fusion of (a) comprises a toxin domain, a binding domain, and optionally a translocation domain. In another embodiment, the toxin domain is at the amino or carboxyl terminus of the recombinant toxin fusion. In another embodiment, the binding domain is at an opposite terminus of the toxin domain. In another embodiment, the binding domain is or comprises a receptor-binding molecule or a binding fragment thereof, a peptide or a binding fragment thereof, an antibody or a binding fragment thereof. In another embodiment, the toxin domain is or comprises DTA, PE, saporin, gelonin, perfringolysin, listeriolysin, α-hemolysin, subtilase cytotoxin, bouganin, or ricin toxin domain, or a toxic fragment thereof. In another embodiment, the receptor-binding molecule is or comprises a ligand, or a binding fragment thereof, optionally an orphan ligand, or a binding fragment thereof. In another embodiment, the receptor-binding molecule is or comprises EGF, PTN, CXCL9, GNS, GM2A or FGF, or a binding fragment thereof. In another embodiment, the peptide is or comprises a TAT peptide, Aβ40 or Aβ42, or a binding fragment thereof. In another embodiment, the binding domain comprises a post-translational modification. In another embodiment, the post-translational modification is or comprises phosphorylation, acetylation, glycosylation, amidation, hydroxylation, methylation, ubiquitylation, or mannose-6-phosphate addition. In another embodiment, the post-translational modification is or comprises mannose-6-phosphate addition. In another embodiment, the translocation domain is or comprises DTA or PE translocation domain, or a transmembrane passage forming fragment thereof. In another embodiment, the bacterial cell is *E. coli*. In another embodiment, the yeast cell is *S. cerevisiae* or *P. pastoris*.

C. Cell Lines and Toxin-Producing Cells

In another aspect, the present disclosure provides a toxin-resistant cell line, in particular, a Diphtheria toxin (DTA)-resistant and a *Pseudomonas* exotoxin A (PE)-resistant cell line.

Accordingly, also provided is a toxin-resistant cell line, comprising a population of cells comprises and expresses at least one nucleic acid molecule, wherein the nucleic acid molecule comprises a nucleic acid sequence encoding Cas or Cpf1, and a nucleic acid sequence encoding at least one gRNA targeting DPH1, DPH2, DPH3, DPH5, DPH7, or DNAJC24, preferably DNAJC24. In an embodiment, the cell line comprises a population of cells resistant to a toxin. In another embodiment, the toxin is Diphtheria toxin (DTA) or *Pseudomonas* exotoxin A (PE). In another embodiment, the population of cells is resistant to a toxin up to 50, 100, 150 or 200 μM, optionally 100 μM. In another embodiment, the Cas is Cas9. In another embodiment, the cell line is HEK-293, preferably HEK-293T.

Also provided is specifically a Diphtheria toxin (DTA)-resistant cell line comprising a population of cells comprises and expresses at least one nucleic acid molecule, wherein the nucleic acid molecule comprises a nucleic acid sequence encoding Cas or Cpf1, and a nucleic acid sequence encoding at least one gRNA targeting HBEGF, DPH1, DPH2, DPH3, DPH5, DPH7, or DNAJC24, preferably DNAJC24. In an embodiment, the population of cells is resistant to DTA up to 50, 100, 150, or 200 μM, optionally 100 μM. In another embodiment, the Cas is Cas9. In another embodiment, the DTA-resistant cell line is HEK-293, preferably HEK-293T.

Also provided is specifically a *Pseudomonas* exotoxin A (PE)-resistant cell line comprising a population of cells comprises and expresses at least one nucleic acid molecule, wherein the nucleic acid molecule comprises a nucleic acid sequence encoding Cas or Cpf1, and a nucleic acid sequence encoding at least one gRNA targeting FURIN, MESDC2, LRP1, LRP1B, DPH1, DPH2, DPH3, DPH5, DPH7, or DNAJC24, preferably DNAJC24. In an embodiment, the population of cells is resistant to PE up to 50, 100, 150, or 200 μM, optionally 100 μM. In another embodiment, the Cas is Cas9. In another embodiment, the PE-resistant cell line is HEK-293, preferably HEK-293T.

In another aspect, the present disclosure provides a toxin-producing cell line comprising a population of cells comprises and expresses at least one nucleic acid molecule, wherein the nucleic acid molecule comprises a nucleic acid sequence encoding Cas or Cpf1, a nucleic acid sequence encoding at least one gRNA targeting DPH1, DPH2, DPH3, DPH5, DPH7, or DNAJC24, preferably DNAJC24, and a nucleic acid sequence encoding a toxin or a recombinant toxin fusion. In embodiment, the toxin is Diphtheria toxin (DTA) or *Pseudomonas* exotoxin A (PE). In another embodiment, the recombinant toxin fusion comprises a toxin domain, a binding domain, and optionally a translocation domain. In another embodiment, the toxin domain is at the amino or carboxyl terminus of the recombinant toxin fusion. In another embodiment, binding domain is at an opposite terminus of the toxin domain. In another embodiment, the binding domain is or comprises a receptor-binding molecule, a peptide, an antibody, or a binding fragment thereof. In another embodiment, the toxin or toxin domain is or comprises DTA or PE toxin domain, or a toxic fragment thereof. In another embodiment, the receptor-binding molecule is or comprises a ligand, or a binding fragment thereof, optionally an orphan ligand, or a binding fragment thereof. In another embodiment, the receptor-binding molecule is or comprises EGF, PTN, CXCL9, GNS, GM2A or FGF, or a binding fragment thereof. In another embodiment, the peptide is or comprises a TAT peptide, Aβ40 or Aβ42, or a binding fragment thereof. In another embodiment, the binding domain comprises a post-translational modification. In another embodiment, the post-translational modification is or comprises phosphorylation, acetylation, glycosylation, amidation, hydroxylation, methylation, ubiquitylation, or mannose-6-phosphate addition. In another embodiment, the post-translational modification is or comprises mannose-6-phosphate addition. In another embodiment, the translocation domain is or comprises DTA or PE translocation domain, or a transmembrane passage forming fragment thereof. In another embodiment, the Cas is Cas9. In another embodiment, the toxin-producing cell line is HEK-293, preferably HEK-293T. In an embodiment, the nucleic acid molecule comprises a nucleic acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, or 99.999% sequence identity to SEQ ID NO:1. In an embodiment, the nucleic acid molecule comprises a nucleic acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, or 99.999% sequence identity to SEQ ID NO:3. In an embodiment, the nucleic acid molecule comprises a nucleic acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, or 99.999% sequence identity to SEQ ID NO:5. In an embodiment, the gRNA targeting DPH1 having nucleic acid sequence comprises at least one of SEQ ID NO: 13, 14, 15, and 16. In an embodiment, the gRNA targeting DPH2 having nucleic acid sequence comprises at least one of SEQ ID NO: 17, 18, 19, and 20. In an embodiment, the gRNA targeting DPH3 having nucleic acid sequence comprises at least one of SEQ ID NO: 21, 22, 23, and 24. In an embodiment, the gRNA targeting DPH5 having nucleic acid sequence comprises at least one of SEQ ID NO: 25, 26, 27, and 28. In an embodiment, the gRNA targeting DPH7 having nucleic acid sequence comprises at least one of SEQ ID NO: 29, 30, 31, and 32. In an embodiment, the gRNA targeting DNAJC24 having nucleic acid sequence comprises at least one of SEQ ID NO: 33, 34, 35, and 36. In an embodiment, the gRNA targeting HBEGF having nucleic acid sequence comprises at least one of SEQ ID NO: 37, 38, 39, and 40. In an embodiment, the gRNA targeting FURIN having nucleic acid sequence comprises at least one of SEQ ID NO: 41, 42, 43, and 44. In an embodiment, the gRNA targeting MESDC2 having nucleic acid sequence comprises at least one of SEQ ID NO: 45, 46, 47, and 48. In an embodiment, the gRNA targeting LRP1 having nucleic acid sequence comprises at least one of SEQ ID NO: 49, 50, 51, and 52. In an embodiment, the gRNA targeting LRP1B having nucleic acid sequence comprises at least one of SEQ ID NO: 53, 54, 55, and 56.

In another aspect, the present disclosure provides a toxin-producing cell, optionally a bacterial, insect or yeast cell comprising a nucleic acid molecule, wherein the nucleic acid molecule comprises a nucleic acid sequence expressing a toxin or a recombinant toxin fusion. In an embodiment, the toxin-producing cell is a bacteria cell. In an embodiment, the nucleic acid molecule comprises a nucleic acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, or 99.999% sequence identity to SEQ ID NO:2. In an embodiment, the nucleic acid molecule comprises a nucleic acid sequence having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, or 99.999% sequence identity to SEQ ID NO:4.

In an embodiment, the toxin is DTA, PE, saporin, gelonin, perfringolysin, listeriolysin, α-hemolysin, subtilase cytotoxin, bouganin, or ricin. In another embodiment, the recombinant toxin fusion comprises a toxin domain, a binding domain, and optionally a translocation domain. In another embodiment, the toxin domain is DTA, PE, saporin, gelonin, perfringolysin, listeriolysin, α-hemolysin, subtilase cytotoxin, bouganin, or ricin toxin domain, or a toxic fragment thereof. In another embodiment, the toxin domain is at the amino or carboxyl terminus of the recombinant toxin fusion. In another embodiment, the binding domain is at an opposite terminus of the toxin domain. In another embodiment, the binding domain is or comprises a receptor-binding molecule, a peptide, an antibody, or a binding fragment thereof. In another embodiment, the receptor-binding molecule is or comprises a ligand, or a binding fragment thereof optionally an orphan ligand, or a binding fragment thereof. In another embodiment, the receptor-binding molecule is or comprises EGF, PTN, CXCL9, GNS, GM2A or FGF, or a binding fragment thereof. In another embodiment, the peptide is or comprises a TAT peptide, Aβ40 or Aβ42, or a binding fragment thereof. In another embodiment, the binding domain comprises a post-translational modification. In another embodiment, the post-translational modification is or comprises phosphorylation, acetylation, glycosylation, amidation, hydroxylation, methylation, ubiquitylation, or mannose-6-phosphate addition. In another embodiment, the post-translational modification is or comprises mannose-6-phosphate addition. In another embodiment, the translocation domain is or comprises DTA or PE translocation domain, or a transmembrane passage forming fragment thereof. In another embodiment, the bacterial cell is *E. coli*. In another embodiment, the yeast cell is *S. cerevisiae* or *P. pastoris*.

D. Nucleic Acid Molecules and Recombinant Toxin Fusions

The present disclosure also provides a nucleic acid molecule comprising a nucleic acid sequence encoding a recombinant toxin fusion, wherein the recombinant toxin fusion comprising a toxin domain, a binding domain, and optionally a translocation domain, wherein the toxin domain is at the amino or carboxyl terminus of the recombinant toxin fusion, wherein the binding domain is at an opposite terminus of the toxin domain, and wherein the binding domain is or comprises a receptor-binding molecule, a peptide, an antibody, or a binding fragment thereof. In an embodiment, the toxin domain is or comprises Diphtheria toxin (DTA), *Pseudomonas* exotoxin A (PE), saporin, gelonin, perfringolysin, listeriolysin, α-hemolysin, subtilase cytotoxin, bouganin, or ricin toxin domain, or a toxic fragment thereof. In another embodiment, the receptor-binding molecule is or comprises a ligand, or a binding fragment thereof, optionally an orphan ligand, or a binding fragment thereof. In another embodiment, the receptor-binding molecule is or comprises EGF, PTN, CXCL9, GNS, GM2A or FGF, or a binding fragment thereof. In another embodiment, the peptide is or comprises a TAT peptide, Aβ40 or Aβ42, or a binding fragment thereof. In another embodiment, the binding domain comprises a post-translational modification. In another embodiment, the post-translational modification is or comprises phosphorylation, acetylation, glycosylation, amidation, hydroxylation, methylation, ubiquitylation, or mannose-6-phosphate addition. In another embodiment, the post-translational modification is or comprises mannose-6-phosphate addition. In another embodiment, the translocation domain is or comprises DTA or PE translocation domain, or a transmembrane passage forming fragment thereof.

The nucleic acid encoding the recombinant toxin fusion can be comprised in a vector such as a plasmid, optionally as described in the Examples. The plasmid may include one or more sequence parts or components of the plasmids described in the Examples. For example, the vector can be a PE fusion vector, optionally comprising a tag such as a histidine tag optionally the PE fusion vector or a vector comprising components thereof as described in the Examples.

Also provided by the present disclosure is a recombinant toxin fusion comprising a toxin domain, a binding domain, and optionally a translocation domain, wherein the toxin domain is at the amino or carboxyl terminus of the recombinant toxin fusion, wherein the binding domain is at an opposite terminus of the toxin domain, and wherein the binding domain is or comprises a receptor-binding molecule or a binding fragment thereof, a peptide or a binding fragment thereof, an antibody or a binding fragment thereof, a carbohydrate, a small molecule, or a lipid. In an embodiment, the toxin domain is or comprises DTA, PE, saporin, gelonin, perfringolysin, listeriolysin, α-hemolysin, subtilase cytotoxin, bouganin, or ricin toxin domain, or a toxic fragment thereof. In another embodiment, the receptor-binding molecule is or comprises a ligand, or a binding fragment thereof, optionally an orphan ligand, or a binding fragment thereof. In another embodiment, the receptor-binding molecule is or comprises EGF, PTN, CXCL9, GNS, GM2A or FGF, or a binding fragment thereof. In another embodiment, the peptide is or comprises a TAT peptide, Aβ40 or Aβ42, or a binding fragment thereof. In another embodiment, the binding domain comprises a post-translational modification. In another embodiment, the post-translational modification is or comprises phosphorylation, acetylation, glycosylation, amidation, hydroxylation, methylation, ubiquitylation, or mannose-6-phosphate addition. In another embodiment, the post-translational modification is or comprises mannose-6-phosphate addition. In another embodiment, the translocation domain is or comprises DTA or PE translocation domain, or a transmembrane passage forming fragment thereof.

E. Kits and Probes

In another aspect, the present disclosure provides kits for performing the methods disclosed herein.

According, the present disclosure provides a kit for identifying a protein associated with a receptor-ligand interaction comprising one or more of the following:

(a) a first cell line, (b) at least one nucleic acid molecule comprising a nucleic acid sequence encoding a recombinant toxin fusion and capable of expressing the recombinant toxin fusion, optionally comprised in a vector, and optionally (c) a targeting library comprising a plurality of nucleic acid molecules, wherein individual nucleic acid molecules target gene expression of specific genes, wherein the first cell line is resistant to the recombinant toxin fusion, and wherein the recombinant toxin fusion comprises a toxin domain, a binding domain, and optionally a translocation domain.

In an embodiment, the first cell line is HAP1, A431, A549, HCT116, K562, HeLa, preferably HeLa-Kyoto, or HEK-293. The recombinant toxin fusion can be produced from the first cell line which is resistant to the recombinant toxin fusion. The recombinant toxin fusion can also be produced from a bacterial cell, an insect cell or a yeast cell. In an embodiment, the kit further comprises (d) a bacterial cell, optionally *E. coli*, an insect cell, or a yeast cell, optionally *S. cerevisiae* or *P. pastoris.*

The kit can also contain a second cell line which can be used as the target or recipient cells for the targeting library containing nucleic acid molecules targeting gene expression of specific genes. In an embodiment, the kit further comprises (e) a second cell line, optionally A431, A549, HCT116, K562, HAP1, HeLa-Kyoto or HEK-293T cells In another embodiment, the toxin-resistant cell line comprises cells having and expressing at least one nucleic acid molecule comprising a nucleic acid sequence encoding Cas or Cpf1, and a nucleic acid sequence encoding at least one gRNA targeting DPH1, DPH2, DPH3, DPH5, DPH7, or DNAJC24, preferably DNAJC24. In an embodiment, the toxin is a recombinant toxin fusion comprising a toxin domain and a binding domain. In another embodiment, the toxin domain is at the amino or carboxyl terminus of the recombinant toxin fusion. In another embodiment, the binding domain is at an opposite terminus of the toxin domain. In another embodiment, the binding domain is or comprises a receptor-binding molecule or a binding fragment thereof, a peptide or a binding fragment thereof, an antibody or a binding fragment thereof, a carbohydrate, a small molecule, or a lipid. In an embodiment, the toxin domain is or comprises DTA, PE, saporin, gelonin, perfringolysin, listeriolysin, α-hemolysin, subtilase cytotoxin, bouganin, or ricin toxin domain, or a toxic fragment thereof. In another embodiment, the toxin domain is or comprises DTA or PE toxin domain, or a toxic fragment thereof. In another embodiment, the receptor-binding molecule is or comprises a ligand, or a binding fragment thereof, optionally an orphan ligand, or a binding fragment thereof. In another embodiment, the receptor-binding molecule is or comprises EGF, PTN, CXCL9, GNS, GM2A or FGF, or a binding fragment thereof. In another embodiment, the peptide is or comprises a TAT peptide, Aβ40 or Aβ42, or a binding fragment thereof. In another embodiment, the binding domain comprises a post-translational modification. In another embodiment, the post-translational modification is or comprises phosphorylation, acetylation, glycosylation, amidation, hydroxylation, methylation, ubiquitylation, or mannose-6-phosphate addition. In another embodiment, the post-translational modification is or comprises mannose-6-phosphate addition. In another embodiment, the translocation domain is or comprises DTA or PE translocation domain, or a transmembrane passage forming fragment thereof. In another embodiment, the targeting library is comprised in at least one lentiviral vector. In another embodiment, the kit further comprises a set of instructions for identifying the protein. In another embodiment, the kit further comprises a container for packaging at least one cell line, the nucleic acid molecule, the targeting library and the set of instructions, optionally the bacterial cell or the yeast cell.

The nucleic acid encoding the recombinant toxin fusion can be comprised in a vector such as a plasmid, optionally as described in the Examples.

Also provided is a kit for identifying a protein associated with a receptor-ligand interaction comprising:

(a) a first cell line, (b) at least one recombinant toxin fusion, and wherein the recombinant toxin fusion comprises a toxin domain, a binding domain, and optionally a translocation domain, and optionally a targeting library comprising a plurality of nucleic acid molecules, wherein individual nucleic acid molecules target gene expression of specific genes.

In an embodiment, the toxin domain is at the amino or carboxyl terminus of the recombinant toxin fusion. In another embodiment, the binding domain is at an opposite terminus of the toxin domain. In another embodiment, the binding domain is or comprises a receptor-binding molecule or a binding fragment thereof, a peptide or a binding fragment thereof, an antibody or a binding fragment thereof, a carbohydrate, a small molecule, or a lipid. In an embodiment, the toxin domain is or comprises DTA, PE, saporin, gelonin, perfringolysin, listeriolysin, α-hemolysin, subtilase cytotoxin, bouganin, or ricin toxin domain, or a toxic fragment thereof. In another embodiment, the toxin domain is or comprises DTA or PE toxin domain, or a toxic fragment thereof. In another embodiment, the receptor-binding molecule is or comprises a ligand, or a binding fragment thereof, optionally an orphan ligand, or a binding fragment thereof. In another embodiment, the receptor-binding molecule is or comprises EGF, PTN, CXCL9, GNS, GM2A or FGF, or a binding fragment thereof. In another embodiment, the peptide is or comprises a TAT peptide, Aβ40 or Aβ42, or a binding fragment thereof.

Also provided is a probe for identifying a protein associated with a receptor-ligand interaction comprising a polypeptide comprising an amino acid sequence encoding a recombinant toxin fusion, wherein the recombinant toxin fusion comprises a toxin domain, a binding domain, and optionally a translocation domain, wherein the toxin domain is at the amino or carboxyl terminus of the recombinant toxin fusion, wherein the binding domain is at an opposite terminus of the toxin domain, and wherein the binding domain is or comprises a receptor-binding molecule, a peptide, an antibody, or a binding fragment thereof. In an embodiment, the toxin domain is or comprises DTA, PE, saporin, gelonin, perfringolysin, listeriolysin, α-hemolysin, subtilase cytotoxin, bouganin, or ricin toxin domain, or a toxic fragment thereof. In another embodiment, the receptor-binding molecule is or comprises a ligand, or a binding fragment thereof, optionally an orphan ligand, or a binding fragment thereof. In another embodiment, the receptor-binding molecule is or comprises EGF, PTN, CXCL9, GNS, GM2A or FGF, or a binding fragment thereof. In another embodiment, the peptide is or comprises a TAT peptide, Aβ40 or Aβ42, or a binding fragment thereof. In another embodiment, the binding domain comprises a post-translational modification. In another embodiment, the post-translational modification is or comprises phosphorylation, acetylation, glycosylation, amidation, hydroxylation, methylation, ubiquitylation, or mannose-6-phosphate addition. In another embodiment, the post-translational modification is or comprises mannose-6-phosphate addition. In another embodiment, the translocation domain is or comprises DTA or PE translocation domain, or a transmembrane passage forming fragment thereof.

The methods described herein can be used to decipher the wiring of the extracellular protein/protein interaction network to identify novel drug targets. In regenerative medicine, the methods can for example be used to identify receptors and pathways that regulate the response of host tissue to engineered and engrafted cells. Furthermore, the identification of novel cell-type specific recombinant toxin fusions enables selective depletion of undesired cell types during in vitro differentiation. These identified toxins can be applied to a cultured population of multiple cell types for killing specific cell types. In cancer therapy, immunology and immuno-oncology, the methods described herein can identify factors that regulate the binding of antibodies and other biologicals to their target cells. For example, conjugate monoclonal antibody/biologics to a toxin can be used to screen for factors that regulate the entry of the antibody or toxin conjugate into cells. The skilled person in the art can readily modify the assay to identify cellular targets of small molecules that act through membrane proteins such as G protein coupled receptors (GPCRs).

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

Example 1

Method for Discovery of Cell Surface Receptors for Extracellular Proteins

Receptor-Ligand Interaction Platform

Without wishing to be bound by theory, bacterial exotoxins, such as Diphtheria toxin (DTA) and *Pseudomonas* exotoxin A (PE), intoxicate cells with picomolar potency by a three-step mechanism (FIG. 1). First, the toxin's receptor-binding molecule binds to a specific receptor or receptors on the host cell surface (e.g. HBEGF for DTA, LRP1 and LRP1B (Accession number NM_018557) for PE), followed by endocytosis. In the second step, the toxin translocates from endosomes to the cytoplasm by employing its translocation domain. Third, the toxin domain causes cell death or inhibits growth, for example, by potently inhibiting protein synthesis, leading to rapid cell death. Different toxins have different mechanisms for inhibiting growth or causing cell death. For example SubA causes excessive ER stress by cleaving an ER resident chaperone BiP, and other toxins inhibit Ras pathway components etc. Notably, if the receptor-binding molecule of the toxin is replaced by an unrelated secreted protein, the toxin retains its potency but enters the cell through the new cognate receptor. The DTA-IL2 fusion denileukin diftitox (ONTAK®), an FDA approved drug targeting cells expressing the IL2 receptor, highlights the specificity and potency of such fusion toxins.

Figure 2:
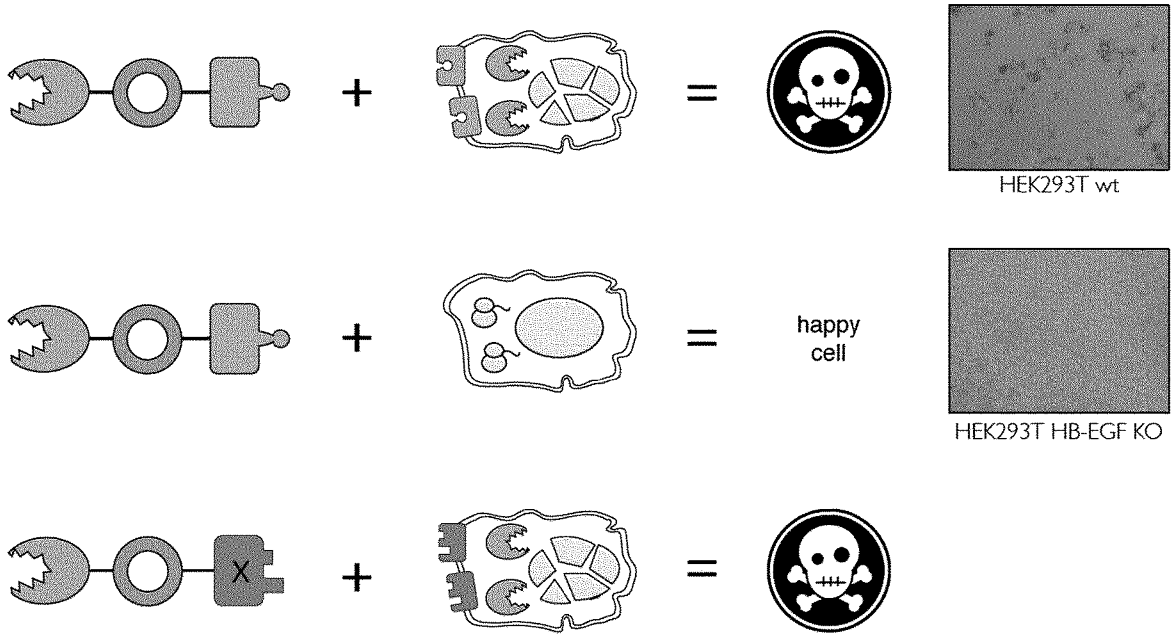
FIG. 2 shows a schematic diagram of engineered exotoxins for ligand-receptor interactions.

Importantly, as shown herein because intoxication requires receptor-mediated endocytosis, cells lacking the cognate receptor to a recombinant fusion toxin are completely resistant to the toxin (see for example, FIG. 2 depicting resistant HEK293T cells lacking HB-EGF, the unique receptor for Diphtheria toxin A). As described herein, on this basis, methods and components for genome-wide genetic screens such as the CRISPR/Cas9-based positive genetic screen described herein are provided. Infecting cells with a genome-wide gRNA library followed by recombinant toxin fusion treatment allows the identification of rare resistant cells. Sequencing of gRNAs from resistant cells will identify the cognate receptor and factors required for receptor surface expression and functionalization (FIG. 3).

Experimental Setup

Plasmids

Figure 4:
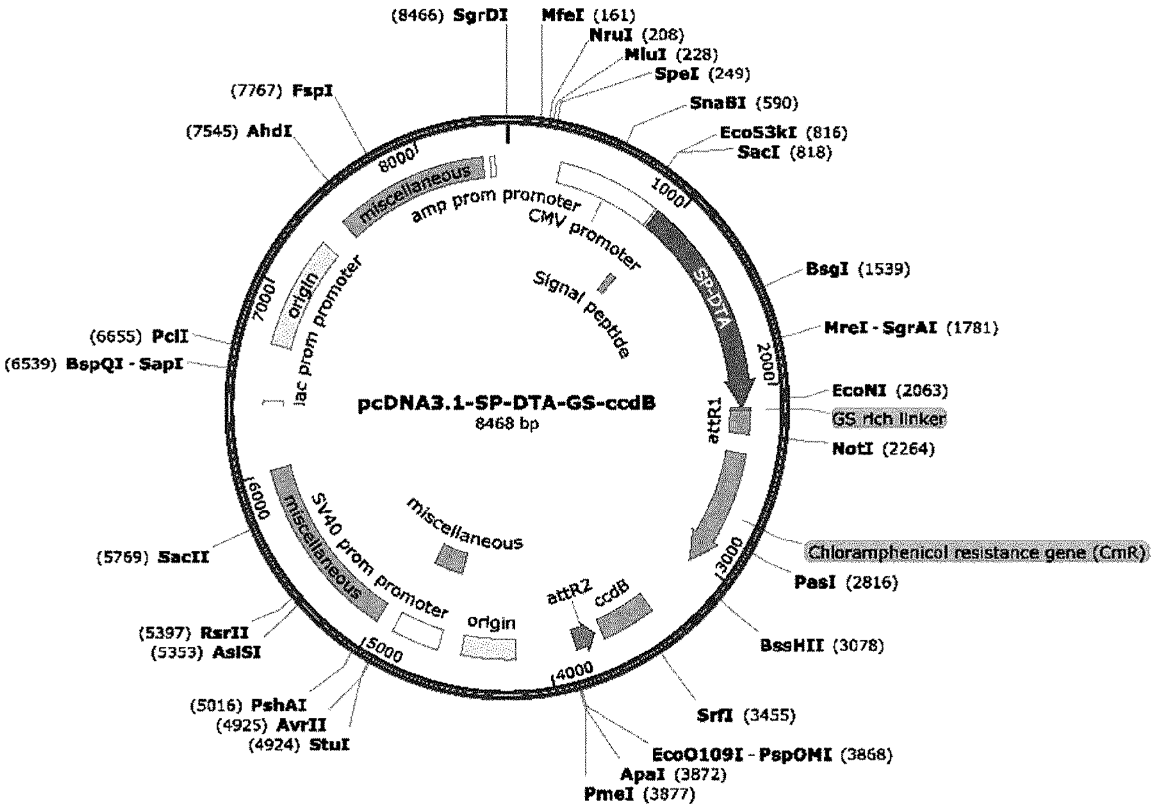
FIG. 4 shows a schematic diagram of destination plasmid pET15b-SHT-SUMO-DTA-ccdB for bacterial expression of Diphtheria toxin-ligands.

The present disclosure provides the following plasmids:

Plasmid 1: Destination plasmid pcDNA3.1-SP-DTA-GS-ccdB for mammalian expression of Diphtheria toxin-ligands (FIG. 4; SEQ ID NO:1). Ligands were cloned in between the two attR sites using Gateway LR cloning.

Figure 5:
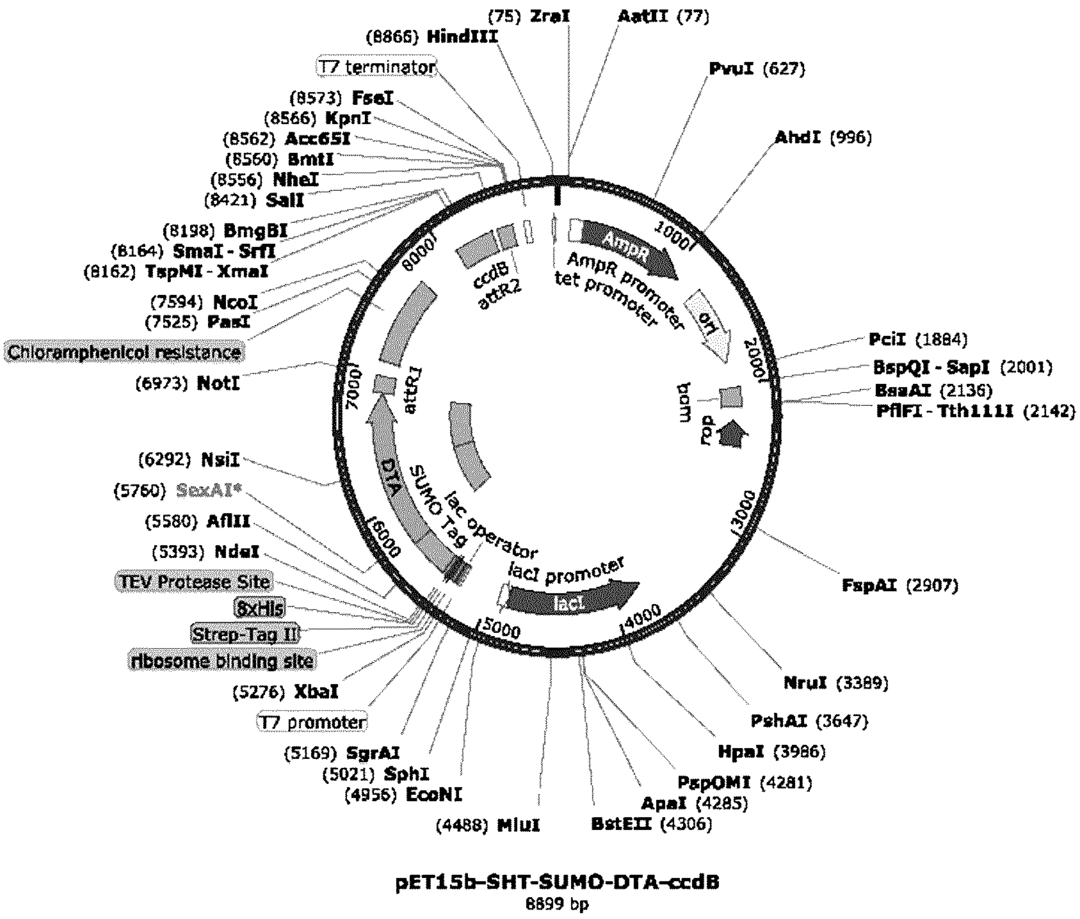
FIG. 5 shows a schematic diagram of destination plasmid pcDNA3.1-SP-ccdB-GSlinker-PE40 for mammalian expression of ligand-exotoxin A.

Plasmid 2: Destination plasmid pET15b-SHT-SUMO-DTA-ccdB for bacterial expression of Diphtheria toxin-ligands (FIG. 5; SEQ ID NO:2). Ligands were cloned in between the two attR sites using Gateway LR cloning.

Figure 6:
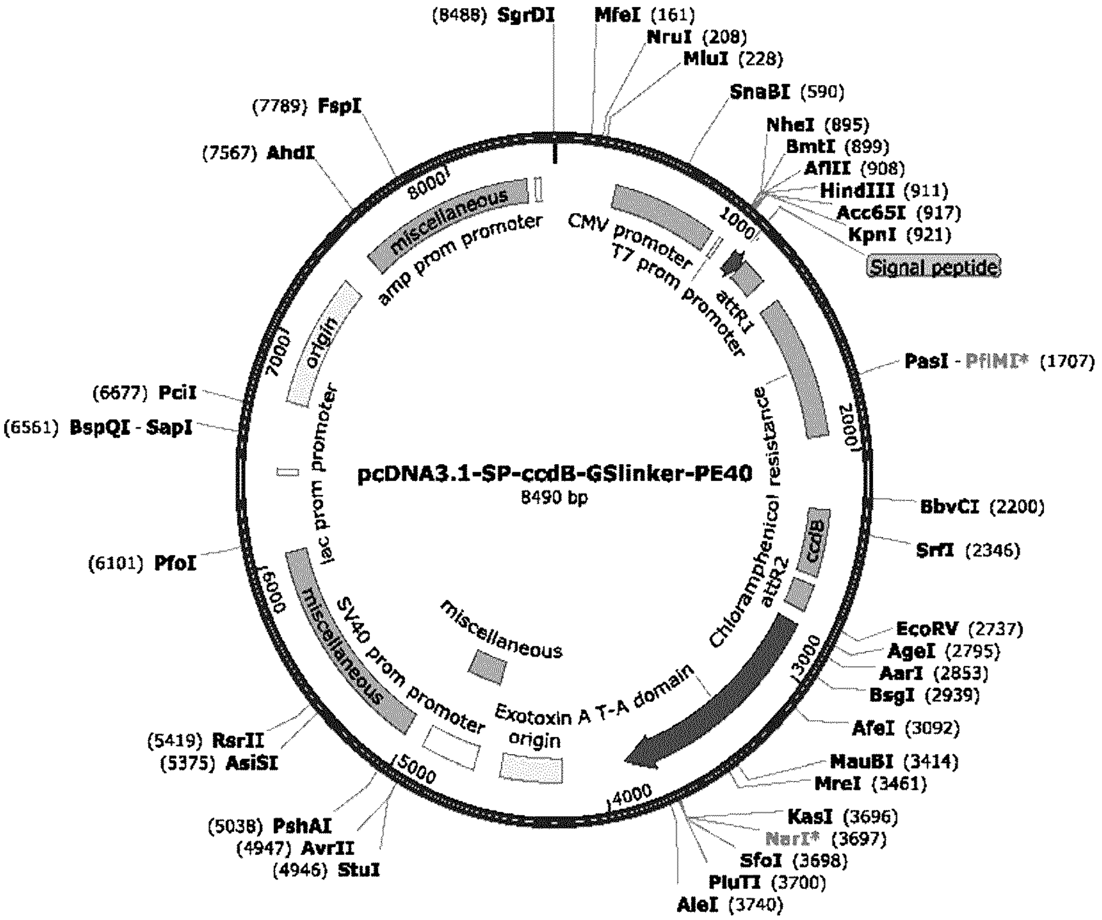
FIG. 6 shows a schematic diagram of destination plasmid pET15b-SHT-ccd-PE40 for bacterial expression of ligand-exotoxin A.

Plasmid 3: Destination plasmid pcDNA3.1-SP-ccdB-GSlinker-PE40 for mammalian expression of ligand-exotoxin A (FIG. 6; SEQ ID NO:3). Ligands are cloned in between the two attR sites using Gateway LR cloning.

Plasmid 4. Destination plasmid pET15b-SHT-ccd-PE40 for bacterial expression of ligand-exotoxin A (FIG. 7; SEQ ID NO:4). Ligands can be cloned in between the two attR sites using Gateway LR cloning.

Figure 21:
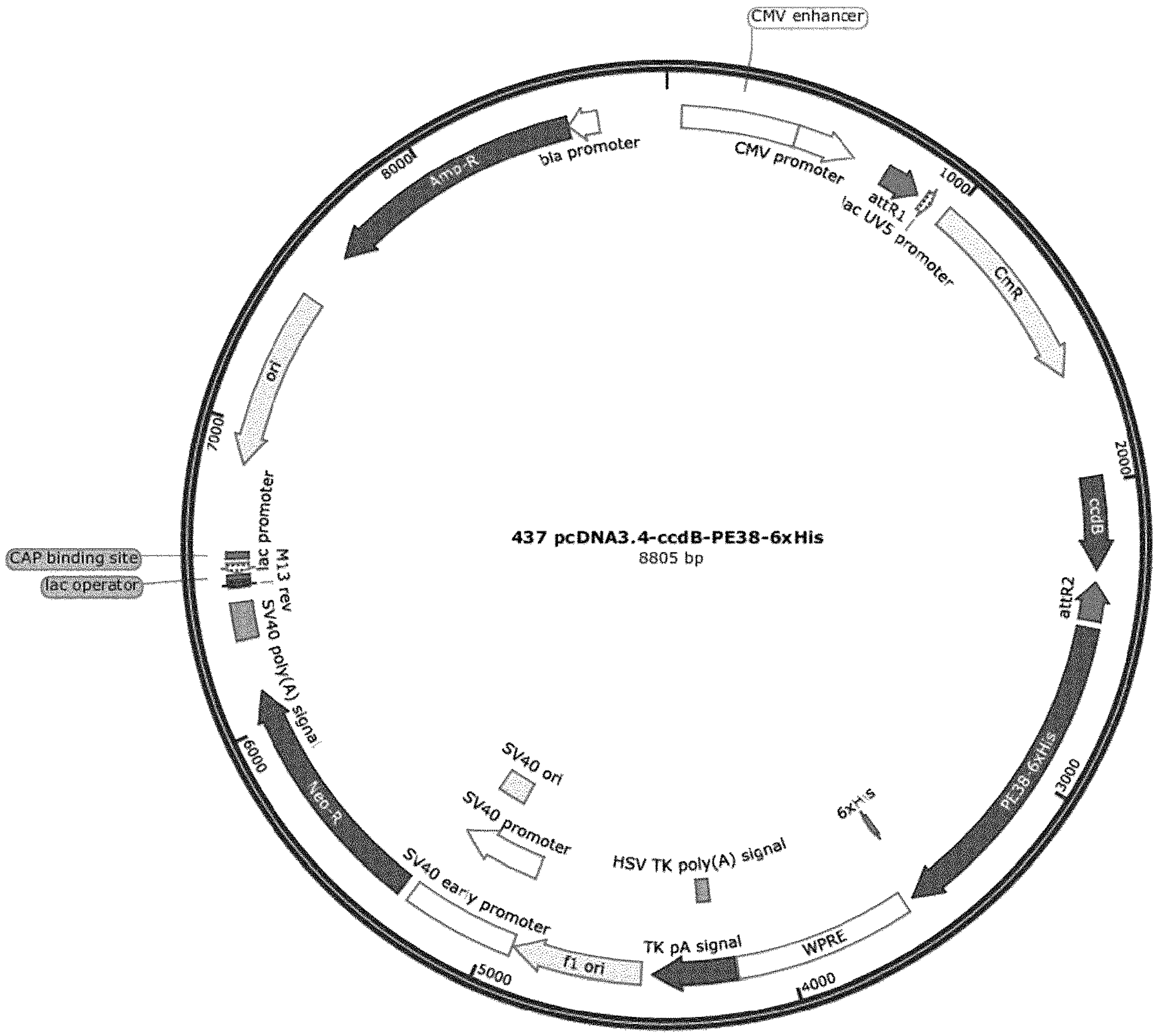
FIG. 21 shows a schematic diagram of destination plasmid pcDNA3.1-ccdB-PE38-6×His for mammalian expression of ligand-exotoxin A.

Plasmid 5. Destination plasmid pcDNA3.1-ccdB-PE38-6×His for mammalian expression of ligand-exotoxin A (FIG. 21; SEQ ID NO:5). Ligands are cloned in between the two attR sites using Gateway LR cloning. This provides a PE fusion vector with a C-terminal 6×His tag.

The difference between plasmid 3 and plasmid 5 is that in plasmid 5, PE38 lacks one loop of the wild-type exotoxin A.

Nucleic acid sequences described herein are set out in Table 1A for the sequences of plasmids, and Table 1B for sequences of CRISPR-Cas PAM sequences, target sites and gRNAs.

TABLE 1A

| Sequences of plasmids | |
|---|---|
| 1 | SEQ ID NO: 1 nucleic acid sequence of plasmid 1 (pcDNA3.1-SP-DTA-GS-ccdB)<br>gacggatcgggagatctcccgatcccctatggtgcactctcagtacaatctgctctgatgccgcatagttaagc<br>cagtatctgctccctgcttgtgtgttggaggtcgctgagtagtgcgcgagcaaaatttaagctacaacaaggca<br>aggcttgaccgacaattgcatgaagaatctgcttagggttaggcgttttgcgctgcttcgcgatgtacgggcca |

TABLE 1A-continued

| Sequences of plasmids |
|---|
| gatatacgcgttgacattgattattgactagttattaatagtaatcaattacggggtcattagttcatagccca<br>tatatggagttccgcgttacataacttacggtaaatggcccgcctggctgaccgcccaacgacccccgcccatt<br>gacgtcaataatgacgtatgttcccatagtaacgccaatagggactttccattgacgtcaatgggtggagtatt<br>tacggtaaactgcccacttggcagtacatcaagtgtatcatatgccaagtacgccccctattgacgtcaatgac<br>ggtaaatggcccgcctggcattatgcccagtacatgaccttatgggactttcctacttggcagtacatctacGT<br>ATTAGTCATCGCTATTACCATGGTGATGCGGTTTTGGCAGTACATCAATGGGCGTGGATAGCGGTTTGACTCAC<br>GGGGATTTCCAAGTCTCCACCCCATTGACGTCAATGGGAGTTTGTTTTGGCACCAAAATCAACGGGACTTTCCA<br>AAATGTCGTAACAACTCCGCCCCATTGACGCAAATGGGCGGTAGGCGTGTACGGTGGGAGGTCTATATAAGCAG<br>AGCTCGTTTAGTGAACCGTCAGATCGCCTGGAGACGCCATCCACGCTGTTTTGACCTCCATAGAAGACACCGAC<br>TCTAGAGGATCCAGCCatgaagctctccctggtggccgcgatgctgctgctgctcagcgcggcgcgggccgagG<br>ATCCTGATGATGTTGTTGATTCTTCTAAATCTTTTGTGATGGAAAACTTTTCTTCGTACCACGGGACTAAACCT<br>GGTTATGTAGATTCCATTCAAAAAGGTATACAAAAGCCAAAATCTGGTACACAAGGAAATTATGACGATGATTG<br>GAAAGGGTTTTATAGTACCGACAATAAATACGACGCTGCGGGATACTCTGTAGATAATGAAAACCCGCTCTCTG<br>GAAAAGCTGGAGGCGTGGTCAAAGTGACGTATCCAGGACTGACGAAGGTTCTCGCACTAAAAGTGGATAATGCC<br>GAAACTATTAAGAAAGAGTTAGGTTTAAGTCTCACTGAACCGTTGATGGAGCAAGTCGGAACGGAAGAGTTTAT<br>CAAAAGGTTCGGTGATGGTGCTTCGCGTGTAGTGCTCAGCCTTCCCTTCGCTGAGGGGAGTTCTAGCGTTGAAT<br>ATATTAATAACTGGGAACAGGCGAAAGCGTTAAGCGTAGAACTTGAGATTAATTTTGAAACCCGTGGAAAACGT<br>GGCCAAGATGCGATGTATGAGTATATGGCTCAAGCCTGTGCAGGAAATCGTGTCAGGCGATCTGTGGGCAGCAG<br>CCTGAGCTGCATCAACCTGGACTGGGACGTGATCCGCGACAAGACCAAGACCAAGATCGAGAGCCTGAAGGAGC<br>ACGGCCCCATCAAGAACAAGATGAGCGAGAGCCCCAACAAGACCGTGAGCGAGGAGAAGGCCAAGCAGTACCTG<br>GAGGAGTTCCACCAGACCGCCCTGGAGCACCCCGAGCTGAGCGAGCTGAAGACCGTGACCGGCACCAACCCCGT<br>GTTCGCCGGCGCCAACTACGCCGCCTGGGCCGTGAACGTGGCCCAGGTGATCGACAGCGAGACCGCCGACAACC<br>TGGAGAAGACCACCGCCGCCCTGAGCATCCTGCCCGGCATCGGCAGCGTGATGGGCATCGCCGACGGCGCCGTG<br>CACCACAACACCGAGGAGATCGTGGCCCAGAGCATCGCCCTGAGCAGCCTGATGGTGGCCCAGGCCATCCCCCT<br>GGTGGGCGAGCTGGTGGACATCGGCTTCGCCGCCTACAACTTCGTGGAGAGCATCATCAACCTGTTCCAGGTGG<br>TGCACAACAGCTACAACCGCCCCGCCTACAGCCCCGGCCACAAGACCTCGAGTGGCTCGGGCTCGACAAGTTTG<br>TACAAAAAAGCTGAACGAGAAACGTAAAATGATATAAATATCAATATATTAAATTAGATTTTGCATAAAAAACA<br>GACTACATAATACTGTAAAACACAACATATCCAGTCACTATGGCGGCCGCATTAGGCACCCCAGGCTTTACACT<br>TTATGCTTCCGGCTCGTATAATGTGTGGATTTTGAGTTAGGATCCGGCGAGATTTTCAGGAGCTAAGGAAGCTA<br>AAATGGAGAAAAAAATCACTGGATATACCACCGTTGATATATCCCAATGGCATCGTAAAGAACATTTTGAGGCA<br>TTTCAGTCAGTTGCTCAATGTACCTATAACCAGACCGTTCAGCTGGATATTACGGCCTTTTTAAAGACCGTAAA<br>GAAAAATAAGCACAAGTTTTATCCGGCCTTTATTCACATTCTTGCCCGCCTGATGAATGCTCATCCGGAATTCC<br>GTATGGCAATGAAAGACGGTGAGCTGGTGATATGGGATAGTGTTCACCCTTGTTACACCGTTTTCCATGAGCAA<br>ACTGAAACGTTTTCATCGCTCTGGAGTGAATACCACGACGATTTCCGGCAGTTTCTACACATATATTCGCAAGA<br>TGTGGCGTGTTACGGTGAAAACCTGGCCTATTTCCCTAAAGGGTTTATTGAGAATATGTTTTTCGTCTCAGCCA<br>ATCCCTGGGTGAGTTTCACCAGTTTTGATTTAAACGTGGCCAATATGGACAACTTCTTCGCCCCCGTTTTCACC<br>ATGGGCAAATATTATACGCAAGGCGACAAGGTGCTGATGCCGCTGGCGATTCAGGTTCATCATGCCGTCTGTGA<br>TGGCTTCCATGTCGGCAGAATGCTTAATGAATTACAACAGTACTGCGATGAGTGGCAGGGCGGGGCGTAAAGAT<br>CTGGATCCGGCTTACTAAAAGCCAGATAACAGTATGCGTATTTGcgcgctgatttttgcggtataagaatatat<br>actgatatgtatacccgaagtatgtcaaaaagaggtatgctatgaagcagcgtattacagtgacagttgacagc<br>gacagctatcagttgctcaaggcatatatgatgtcaatatctccggtctggtaagcacaaccatgcagaatgaa<br>gcccgtcgtctgcgtgccgaacgctggaaagcggaaaatcaggaagggatggctgaggtcgcccggtttattga<br>aatgaacggctcttttgctgacgagaacaggggctggtgaaatgcagtttaaggtttacacctataaaagagag<br>agccgttatcgtctgtttgtggatgtacagagtgatattattgacacgcccgggcgacggatggtgatcccccct<br>ggccagtgcacgtctgctgtcagataaagtctcccgtgaactttacccggtggtgcatatcggggatgaaagct<br>ggcgcatgatgaccaccgatatggccagtgtgccggtctccgttatcggggaagaagtggctgatctcagccac<br>cgcgaaaatgacatcaaaaacgccattaacctgatgttctggggaatataaatgtcaggctcccttatacacag<br>ccagtctgcaggtcgaccatagtgactggatatgttgtgttttacagtattatgtagtctgttttttatgcaaa<br>atctaatttaatatattgatatttatatcattttacgtttctcgttcagctttcttgtacaaagtggtTGCTCT<br>ATAGTAActcgagtctagagggcccgtttaaacccgctgatcagcctcgactgtgccttctagttgccagccat<br>ctgttgtttgcccctcccccgtgccttccttgaccctggaaggtgccactcccactgtcctttcctaataaaat<br>gaggaaattgcatcgcattgtctgagtaggtgtcattctattctggggggtggggtggggcaggacagcaaggg<br>ggaggattgggaagacaatagcaggcatgctggggatgcggtgggctctatggcttctgaggcggaaagaacca<br>gctggggctctagggggtatccccacgcgccctgtagcggcgcattaagcgcggcgggtgtggtggttacgcgc<br>agcgtgaccgctacacttgccagcgccctagcgcccgctcctttcgctttcttcccttcctttctcgccacgtt<br>cgccggctttccccgtcaagctctaaatcgggggctccctttagggttccgatttagtgctttacggcacctcg<br>accccaaaaaacttgattagggtgatggttcacgtagtgggccatcgccctgatagacggtttttcgccctttg<br>acgttggagtccacgttctttaatagtggactcttgttccaaactggaacaacactcaaccctatctcggtcta<br>ttcttttgatttataagggattttgccgatttcggcctattggttaaaaaatgagctgatttaacaaaaattta<br>acgcgaattaattctgtggaatgtgtgtcagttagggtgtggaaagtccccaggctccccagcaggcagaagta<br>tgcaaagcatgcatctcaattagtcagcaaccaggtgtggaaagtccccaggctccccagcaggcagaagtatg<br>caaagcatgcatctcaattagtcagcaaccatagtcccgcccctaactccgcccatcccgcccctaactccgcc<br>cagttccgcccattctccgccccatggctgactaattttttttatttatgcagaggccgaggccgcctctgcct<br>ctgagctattccagaagtagtgaggaggcttttttggaggcctaggcttttgcaaaaagctcccgggagcttgt<br>atatccattttcggatctgatcagcacgtgatgaaaaagcctgaactcaccgcgacgtctgtcgagaagtttct<br>gatcgaaaagttcgacagcgtctccgacctgatgcagctctcggagggcgaagaatctcgtgctttcagcttcg<br>atgtaggagggcgtggatatgtcctgcgggtaaatagctgcgccgatggtttctacaaagatcgttatgtttat<br>cggcactttgcatcggccgcgctcccgattccggaagtgcttgacattggggaattcagcgagagcctgaccta<br>ttgcatctcccgccgtgcacagggtgtcacgttgcaagacctgcctgaaaccgaactgcccgctgttctgcagc<br>cggtcgcggaggccatggatgcgatcgctgcggccgatcttagccagacgagcgggttcggcccattcggaccg<br>caaggaatcggtcaatacactacatggcgtgatttcatatgcgcgattgctgatccccatgtgtatcactggca<br>aactgtgatggacgacaccgtcagtgcgtccgtcgcgcaggctctcgatgagctgatgctttgggccgaggact<br>gccccgaagtccggcacctcgtgcacgcggatttcggctccaacaatgtcctgacggacaatggccgcataaca<br>gcggtcattgactggagcgaggcgatgttcggggattcccaatacgaggtcgccaacatcttcttctggaggcc<br>gtggttggcttgtatggagcagcagacgcgctacttcgagcggaggcatccggagcttgcaggatcgccgcggc<br>tccgggcgtatatgctccgcattggtcttgaccaactctatcagagcttggttgacggcaatttcgatgatgca<br>gcttgggcgcagggtcgatgcgacgcaatcgtccgatccggagccgggactgtcgggcgtacacaaatcgcccg<br>cagaagcgcggccgtctggaccgatggctgtgtagaagtactcgccgatagtggaaaccgacgccccagcactc |

TABLE 1A-continued

Sequences of plasmids gtccgagggcaaaggaatagcacgtgctacgagatttcgattccaccgccgccttctatgaaaggttgggcttc
ggaatcgttttccgggacgccggctggatgatcctccagcgcggggatctcatgctggagttcttcgcccaccc
caacttgtttattgcagcttataatggttacaaataaagcaatagcatcacaaatttcacaaataaagcatttt
tttcactgcattctagttgtggtttgtccaaactcatcaatgtatcttatcatgtctgtataccgtcgacctct
agctagagcttggcgtaatcatggtcatagctgtttcctgtgtgaaattgttatccgctcacaattccacacaa
catacgagccggaagcataaagtgtaaagcctggggtgcctaatgagtgagctaactcacattaattgcgttgc
gctcactgcccgctttccagtcgggaaacctgtcgtgccagctgcattaatgaatcggccaacgcgcggggaga
ggcggtttgcgtattgggcgctcttccgcttcctcgctcactgactcgctgcgctcggtcgttcggctgcggcg
agcggtatcagctcactcaaaggcggtaatacggttatccacagaatcaggggataacgcaggaaagaacatgt
gagcaaaaggccagcaaaaggccaggaaccgtaaaaaggccgcgttgctggcgtttttccataggctccgcccc
cctgacgagcatcacaaaaatcgacgctcaagtcagaggtggcgaaacccgacaggactataaagataccaggc
gtttccccctggaagctccctcgtgcgctctcctgttccgaccctgccgcttaccggatacctgtccgcctttc
tcccttcgggaagcgtggcgctttctcatagctcacgctgtaggtatctcagttcggtgtaggtcgttcgctcc
aagctgggctgtgtgcacgaaccccccgttcagcccgaccgctgcgccttatccggtaactatcgtcttgagtc
caacccggtaagacacgacttatcgccactggcagcagccactggtaacaggattagcagagcgaggtatgtag
gcggtgctacagagttcttgaagtggtggcctaactacggctacactagaagaacagtatttggtatctgcgct
ctgctgaagccagttaccttcggaaaaagagttggtagctcttgatccggcaaacaaaccaccgctggtagcgg
tttttttgtttgcaagcagcagattacgcgcagaaaaaaaggatctcaagaagatcctttgatcttttctacgg
ggtctgacgctcagtggaacgaaaactcacgttaagggattttggtcatgagattatcaaaaaggatcttcacc
tagatccttttaaattaaaaatgaagttttaaatcaatctaaagtatatatgagtaaacttggtctgacagtta
ccaatgcttaatcagtgaggcacctatctcagcgatctgtctatttcgttcatccatagttgcctgactccccg
tcgtgtagataactacgatacgggagggcttaccatctggccccagtgctgcaatgataccgcgagacccacgc
tcaccggctccagatttatcagcaataaaccagccagccggaagggccgagcgcagaagtggtcctgcaacttt
atccgcctccatccagtctattaattgttgccgggaagctagagtaagtagttcgccagttaatagtttgcgca
acgttgttgccattgctacaggcatcgtggtgtcacgctcgtcgtttggtatggcttcattcagctccggttcc
caacgatcaaggcgagttacatgatcccccatgttgtgcaaaaaagcggttagctccttcggtcctccgatcgt
tgtcagaagtaagttggccgcagtgttatcactcatggttatggcagcactgcataattctcttactgtcatgc
catccgtaagatgcttttctgtgactggtgagtactcaaccaagtcattctgagaatagtgtatgcggcgaccg
agttgctcttgcccggcgtcaatacgggataataccgcgccacatagcagaactttaaaagtgctcatcattgg
aaaacgttcttcggggcgaaaactctcaaggatcttaccgctgttgagatccagttcgatgtaacccactcgtg
cacccaactgatcttcagcatcttttactttcaccagcgtttctgggtgagcaaaaacaggaaggcaaaatgcc
gcaaaaaagggaataagggcgacacggaaatgttgaatactcatactcttcctttttcaatattattgaagcat
ttatcagggttattgtctcatgagcggatacatatttgaatgtatttagaaaaataaacaaataggggttccgc
gcacatttccccgaaaagtgccacctgacgtc 2 SEQ ID NO: 2 nucleic acid sequence of plasmid 2 (pET15b-SHT-SUMO-DTA-ccdB)
ttcttgaagacgaaagggcctcgtgatacgcctatttttataggttaatgtcatgataataatggtttcttaga
cgtcaggtggcacttttcggggaaatgtgcgcggaacccctatttgtttatttttctaaatacattcaaatatg
tatccgctcatgagacaataaccctgataaatgcttcaataatattgaaaaaggaagagtatgagtattcaaca
tttccgtgtcgcccttattcccttttttgcggcattttgccttcctgtttttgctcacccagaaacgctggtga
aagtaaaagatgctgaagatcagttgggtgcacgagtgggttacatcgaactggatctcaacagcggtaagatc
cttgagagttttcgccccgaagaacgttttccaatgatgagcacttttaaagttctgctatgtggcgcggtatt
atcccgtgttgacgccgggcaagagcaactcggtcgccgcatacactattctcagaatgacttggttgagtact
caccagtcacagaaaagcatcttacggatggcatgacagtaagagaattatgcagtgctgccataaccatgagt
gataacactgcggccaacttacttctgacaacgatcggaggaccgaaggagctaaccgcttttttgcacaacat
gggggatcatgtaactcgccttgatcgttgggaaccggagctgaatgaagccataccaaacgacgagcgtgaca
ccacgatgcctgcagcaatggcaacaacgttgcgcaaactattaactggcgaactacttactctagcttcccgg
caacaattaatagactggatggaggcggataaagttgcaggaccacttctgcgctcggcccttccggctggctg
gtttattgctgataaatctggagccggtgagcgtgggtctcgcggtatcattgcagcactggggccagatggta
agccctcccgtatcgtagttatctacacgacggggagtcaggcaactatggatgaacgaaatagacagatcgct
gagataggtgcctcactgattaagcattggtaactgtcagaccaagtttactcatatatactttagattgattt
aaaacttcatttttaatttaaaaggatctaggtgaagatcctttttgataatctcatgaccaaaatcccttaac
gtgagttttcgttccactgagcgtcagaccccgtagaaaagatcaaaggatcttcttgagatcctttttttctg
cgcgtaatctgctgcttgcaaacaaaaaaaccaccgctaccagcggtggtttgtttgccggatcaagagctacc
aactctttttccgaaggtaactggcttcagcagagcgcagataccaaatactgtccttctagtgtagccgtagt
taggccaccacttcaagaactctgtagcaccgcctacatacctcgctctgctaatcctgttaccagtggctgct
gccagtggcgataagtcgtgtcttaccgggttggactcaagacgatagttaccggataaggcgcagcggtcggg
ctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaaca
ggagagcgcacgagggagcttccagggggaaacgcctggtatctttatagtcctgtcgggtttcgccacctctg
acttgagcgtcgatttttgtgatgctcgtcaggggggcggagcctatggaaaaacgccagcaacgcggcctttt
tacggttcctggccttttgctggccttttgctcacatgttctttcctgcgttatcccctgattctgtggataac
cgtattaccgcctttgagtgagctgataccgctcgccgcagccgaacgaccgagcgcagcgagtcagtgagcga
ggaagcggaagagcgcctgatgcggtattttctccttacgcatctgtgcggtatttcacaccgcatatatggtg
cactctcagtacaatctgctctgatgccgcatagttaagccagtatacactccgctatcgctacgtgactgggt
catggctgcgccccgacacccgccaacacccgctgacgcgccctgacgggcttgtctgctcccggcatccgctt
acagacaagctgtgaccgtctccgggagctgcatgtgtcagaggttttcaccgtcatcaccgaaacgcgcgagg
cagctgcggtaaagctcatcagcgtggtcgtgaagcgattcacagatgtctgcctgttcatccgcgtccagctc
gttgagtttctccagaagcgttaatgtctggcttctgataaagcgggccatgttaagggcggtttttttcctgtt
tggtcactgatgcctccgtgtaagggggatttctgttcatgggggtaatgataccgatgaaacgagagaggatg
ctcacgatacgggttactgatgatgaacatgcccggttactggaacgttgtgagggtaaacaactggcggtatg
gatgcggcgggaccagagaaaaatcactcagggtcaatgccagcgcttcgttaatacagatgtaggtgttccac
agggtagccagcagcatcctgcgatgcagatccggaacataatggtgcagggcgctgacttccgcgtttccaga
ctttacgaaacacggaaaccgaagaccattcatgttgttgctcaggtcgcagacgttttgcagcagcagtcgct
tcacgttcgctcgcgtatcggtgattcattctgctaaccagtaaggcaaccccgccagcctagccgggtcctca
acgacaggagcacgatcatgcgcacccgtggccaggacccaacgctgcccgagatgcgccgcgtgcggctgctg
gagatggcggacgcgatggatatgttctgccaaggttggtttgcgcattcacagttctccgcaagaattgatt
ggctccaattcttggagtggtgaatccgttagcgaggtgccgccggcttccattcaggtcgaggtggcccggct TABLE 1A-continued

| Sequences of plasmids |
|---|
| ccatgcaccgcgacgcaacgcggggaggcagacaaggtatagggcggcgcctacaatccatgccaacccgttcc |
| atgtgctcgccgaggcggcataaatcgccgtgacgatcagcggtccagtgatcgaagttaggctggtaagagcc |
| gcgagcgatccttgaagctgtccctgatggtcgtcatctacctgcctggacagcatggcctgcaacgcgggcat |
| cccgatgccgccggaagcgagaagaatcataatggggaaggccatccagcctcgcgtcgcgaacgccagcaaga |
| cgtagcccagcgcgtcggccgccatgccggcgataatggcctgcttctcgccgaaacgtttggtggcgggacca |
| gtgacgaaggcttgagcgagggcgtgcaagattccgaataccgcaagcgacaggccgatcatcgtcgcgctcca |
| gcgaaagcggtcctcgccgaaaatgacccagagcgctgccggcacctgtcctacgagttgcatgataaagaaga |
| cagtcataagtgcggcgacgatagtcatgccccgcgcccaccggaaggagctgactgggttgaaggctctcaag |
| ggcatcggtcgagatcccggtgcctaatgagtgagctaacttacattaattgcgttgcgctcactgcccgcttt |
| ccagtcgggaaacctgtcgtgccagctgcattaatgaatcggccaacgcgcggggagaggcggtttgcgtattg |
| ggcgccagggtggtttttcttttcaccagtgagacgggcaacagctgattgcccttcaccgcctggccctgaga |
| gagttgcagcaagcggtccacgctggtttgccccagcaggcgaaaatcctgtttgatggtggttaacggcggga |
| tataacatgagctgtcttcggtatcgtcgtatcccactaccgagatatccgcaccaacgcgcagcccggactcg |
| gtaatggcgcgcattgcg(xcagcgccatctgatcgttggcaaccagcatcgcagtgggaacgatgccctcatt |
| cagcatttgcatggtttgttgaaaaccggacatggcactccagtcgccttcccgttccgctatcggctgaattt |
| gattgcgagtgagatatttatgccagccagccagacgcagacgcgccgagacagaacttaatgggcccgctaac |
| agcgcgatttgctggtgacccaatgcgaccagatgctccacgcccagtcgcgtaccgtcttcatgggagaaaat |
| aatactgttgatgggtgtctggtcagagacatcaagaaataacgccggaacattagtgcaggcagcttccacag |
| caatggcatcctggtcatccagcggatagttaatgatcagcccactgacgcgttgcgcgagaagattgtgcacc |
| gccgctttacaggcttcgacgccgcttcgttctaccatcgacaccaccacgctggcacccagttgatcggcgcg |
| agatttaatcgccgcgacaatttgcgacggcgcgtgcagggccagactggaggtggcaacgccaatcagcaacg |
| actgtttgcccgccagttgttgtgccacgcggttgggaatgtaattcagctccgccatcgccgcttccactttt |
| tcccgcgttttcgcagaaacgtggctggcctggttcaccacgcgggaaacggtctgataagagacaccggcata |
| ctctgcgacatcgtataacgttactggtttcacattcaccaccctgaattgactctcttccgggcgctatcatg |
| ccataccgcgaaaggttttgcgccattcgatggtgtccgggatctcgacgctctcccttatgcgactcctgcat |
| taggaagcagcccagtagtaggttgaggccgttgagcaccgccgccgcaaggaatggtgcatgcaaggagatgg |
| cgcccaacagtcccccggccacggggcctgccaccatacccacgccgaaacaagcgctcatgagcccgaagtgg |
| cgagcccgatcttccccatcggtgatgtcggcgatataggcgccagcaaccgcacctgtggcgccggtgatgcc |
| ggccacgatgcgtccggcgtagaggatcgagatctcgatcccgcgaaattaatacgactcactataggggaatt |
| gtgagcggataacaattcccctctagaaataattttgtttaactttaagaaggagatataccatgtggtcccat |
| cctcaattcgagaagcatcaccatcaccatcaccatcacggatctgaaaatctctacttccagcatatgtcgga |
| ctcagaagtcaatcaagaagctaagccagaggtcaagccagaagtcaagcctgagactcacatcaatttaaagg |
| tgtccgatggatcttcagagatcttcttcaagatcaaaaagaccactcctttaagaaggctgatggaagcgttc |
| gctaaaagacagggtaaggaaatggactccttaagattcttgtacgacggtattagaattcaagctgatcagac |
| ccctgaagatttggacatggaggataacgatattattgaggctcacagagaacagattggtggtggcgctgatg |
| atgttgttgattcttctaaatcttttgtgatggaaaacttttcttcgtaccacgggactaaacctggttatgta |
| gattccattcaaaaaggtatacaaaagccaaaatctggtacacaaggaaattatgacgatgattggaaagggtt |
| ttatagtaccgacaataaatacgacgctgcgggatactctgtagataatgaaaacccgctctctggaaaagctg |
| gaggcgtggtcaaagtgacgtatccaggactgacgaaggttctcgcactaaaagtggataatgccgaaactatt |
| aagaaagagttaggtttaagtctcactgaaccgttgatggagcaagtcggaacggaagagtttatcaaaaggtt |
| cggtgatggtgcttcgcgtgtagtgctcagccttcccttcgctgaggggagttctagcgttgaatatattaata |
| actgggaacaggcgaaagcgttaagcgtagaacttgagattaattttgaaacccgtggaaaacgtggccaagat |
| gcgatgtatgagtatatggctcaagcctgtgcaggaaatcgtgtcaggcgatcagtaggtagctcattgtcatg |
| cataaatcttgattgggatgtcataagggataaaactaagacaaagatagagtctttgaaagagcatggcccta |
| tcaaaaataaaatgagcgaaagtcccaataaaacagtatctgaggaaaaagctaaacaatacctagaagaattt |
| catcaaacggcattagagcatcctgaattgtcagaacttaaaaccgttactgggaccaatcctgtattcgctgg |
| ggctaactatgcggcgtgggcagtaaacgttgcgcaagttatcgatagcgaaacagctgataatttggaaaaga |
| caactgctgctctttcgatacttcctggtatcggtagcgtaatgggcattgcagacggtgccgttcaccacaat |
| acagaagagatagtggcacaatcaatagctttatcgtctttaatggttgctcaagctattccattggtaggaga |
| gctagttgatattggtttcgctgcatataattttgtagagagtattatcaatttatttcaagtagttcataatt |
| cgtataatcgtcccgcgtattctccggggcataaaacgacaagtttgtacaaaaaagctgaacgagaaacgtaa |
| aatgatataaatatcaatatattaaattagattttgcataaaaaacagactacataatactgtaaaacacaaca |
| tatccagtcactatggcggccgcattaggcaccccaggctttacactttatgcttccggctcgtataatgtgtg |
| gattttgagttaggatccgtcgagattttcaggagctaaggaagctaaaatggagaaaaaaatcactggatata |
| ccaccgttgatatatcccaatggcatcgtaaagaacattttgaggcatttcagtcagttgctcaatgtacctat |
| aaccagaccgttcagctggatattacggcctttttaaagaccgtaaagaaaaataagcacaagttttatccggc |
| ctttattcacattcttgcccgcctgatgaatgctcatccggaattccgtatggcaatgaaagacggtgagctgg |
| tgatatgggatagtgttcacccttgttacaccgttttccatgagcaaactgaaacgttttcatcgctctggagt |
| gaataccacgacgatttccggcagtttctacacatatattcgcaagatgtggcgtgttacggtgaaaacctggc |
| ctatttccctaaagggtttattgagaatatgtttttcgtctcagccaatccctgggtgagtttcaccagttttg |
| atttaaacgtggccaatatggacaacttcttcgcccccgttttcaccatgggcaaatattatacgcaaggcgac |
| aaggtgctgatgccgctggcgattcaggttcatcatgccgtttgtgatggcttccatgtcggcagaatgcttaa |
| tgaattacaacagtactgcgatgagtggcagggcggggcgtaaagatctggatccggcttactaaaagccagat |
| aacagtatgcgtatttgcgcgctgatttttgcggtataagaatatatactgatatgtatacccgaagtatgtca |
| aaaagaggtatgctatgaagcagcgtattacagtgacagttgacagcgacagctatcagttgctcaaggcatat |
| atgatgtcaatatctccggtctggtaagcacaaccatgcagaatgaagcccgtcgtctgcgtgccgaacgctgg |
| aaagcggaaaatcaggaagggatggctgaggtcgcccggtttattgaaatgaacggctcttttgctgacgagaa |
| caggggctggtgaaatgcagtttaaggtttacacctataaaagagagagccgttatcgtctgtttgtggatgta |
| cagagtgatattattgacacgcccgggcgacggatggtgatcccccctggccagtgcacgtctgctgtcagataa |
| agtctcccgtgaactttacccggtggtgcatatcggggatgaaagctggcgcatgatgaccaccgatatggcca |
| gtgtgccggtctccgttatcggggaagaagtggctgatctcagccaccgcgaaaatgacatcaaaaacgccatt |
| aacctgatgttctggggaatataaatgtcaggctcccttatacacagccagtctgcaggtcgaccatagtgact |
| ggatatgttgtgttttacagtattatgtagtctgtttttatgcaaaatctaatttaatatattgatatttata |
| tcattttacgtttctcgttcagctttcttgtacaaagtggtgtaggctagcggtaccggccggccggatccggc |
| tgctaacaaagcccgaaaggaagctgagttggctgctgccaccgctgagcaataactagcataaccccttgggg |

TABLE 1A-continued

Sequences of plasmids cctctaaacgggtcttgaggggttttttgctgaaaggaggaactatatccggatatcccgcaagaggcccggca
gtaccggcataaccaagcctatgcctacagcatccagggtgacggtgccgaggatgacgatgagcgcattgtta
gatttcatacacggtgcctgactgcgttagcaatttaactgtgataaactaccgcattaaagcttatcgatgat
aagctgtcaaacatgagaa 3 SEQ ID NO: 3 nucleic acid sequence of plasmid 3
(pcDNA3.1-SP-codB-GSlinker-PE40)
gacggatcgggagatctcccgatcccctatggtgcactctcagtacaatctgctctgatgccgcatagttaagc
cagtatctgctccctgcttgtgtgttggaggtcgctgagtagtgcgcgagcaaaatttaagctacaacaaggca
aggcttgaccgacaattgcatgaagaatctgcttagggttaggcgttttgcgctgcttcgcgatgtacgggcca
gatatacgcgttgacattgattattgactagttattaatagtaatcaattacggggtcattagttcatagccca
tatatggagttccgcgttacataacttacggtaaatggcccgcctggctgaccgcccaacgacccccgcccatt
gacgtcaataatgacgtatgttcccatagtaacgccaatagggactttccattgacgtcaatgggtggagtatt
tacggtaaactgcccacttggcagtacatcaagtgtatcatatgccaagtacgccccctattgacgtcaatgac
ggtaaatggcccgcctggcattatgcccagtacatgaccttatgggactttcctacttggcagtacatctacgt
attagtcatcgctattaccatggtgatgcggttttggcagtacatcaatgggcgtggatagcggtttgactcac
ggggatttccaagtctccaccccattgacgtcaatgggagtttgttttggcaccaaaatcaacgggactttcca
aaatgtcgtaacaactccgccccattgacgcaaatgggcggtaggcgtgtacggtgggaggtctatataagcag
agctctctggctaactagagaacccactgcttactggcttatcgaaattaatacgactcactatagggagaccc
aagctggctagcgtttaaacttaagcttggtaccgagctcggatccactagtccagtgtggtggaattctgatg
gagacagacacactcctgctatggGTACTGCTGCTCTGGGTTCCAGGTTCCACTGGTGACgcggccACAAGTTT
GTACAAAAAAGCTGAACGAGAAACGTAAAATGATATAAATATCAATATATTAAATTAGATTTTGCATAAAAAAC
AGACTACATAATACTGTAAAACACAACATATCCAGTCACTATGGCGGCCGCATTAGGCACCCCAGGCTTTACAC
TTTATGCTTCCGGCTCGTATAATGTGTGGATTTTGAGTTAGGATCCGTCGAGATTTTCAGGAGCTAAGGAAGCT
AAAATGGAGAAAAAAATCACTGGATATACCACCGTTGATATATCCCAATGGCATCGTAAAGAACATTTTGAGGC
ATTTCAGTCAGTTGCTCAATGTACCTATAACCAGACCGTTCAGCTGGATATTACGGCCTTTTTAAAGACCGTAA
AGAAAAATAAGCACAAGTTTTATCCGGCCTTTATTCACATTCTTGCCCGCCTGATGAATGCTCATCCGGAATTC
CGTATGGCAATGAAAGACGGTGAGCTGGTGATATGGGATAGTGTTCACCCTTGTTACACCGTTTTCCATGAGCA
AACTGAAACGTTTTCATCGCTCTGGAGTGAATACCACGACGATTTCCGGCAGTTTCTACACATATATTCGCAAG
ATGTGGCGTGTTACGGTGAAAACCTGGCCTATTTCCCTAAAGGGTTTATTGAGAATATGTTTTTCGTCTCAGCC
AATCCCTGGGTGAGTTTCACCAGTTTTGATTTAAACGTGGCCAATATGGACAACTTCTTCGCCCCCGTTTTCAC
CATGGGCAAATATTATACGCAAGGCGACAAGGTGCTGATGCCGCTGGCGATTCAGGTTCATCATGCCGTTTGTG
ATGGCTTCCATGTCGGCAGAATGCTTAATGAATTACAACAGTACTGCGATGAGTGGCAGGGCGGGGCGTAAAGA
TCTGGATCCGGCTTACTAAAAGCCAGATAACAGTATGCGTATTTGCGCGCTGATTTTTGCGGTATAAGAATATA
TACTGATATGTATACCCGAAGTATGTCAAAAAGAGGTATGCTATGAAGCAGCGTATTACAGTGACAGTTGACAG
CGACAGCTATCAGTTGCTCAAGGCATATATGATGTCAATATCTCCGGTCTGGTAAGCACAACCATGCAGAATGA
AGCCCGTCGTCTGCGTGCCGAACGCTGGAAAGCGGAAAATCAGGAAGGGATGGCTGAGGTCGCCCGGTTTATTG
AAATGAACGGCTCTTTTGCTGACGAGAACAGGGGCTGGTGAAATGCAGTTTAAGGTTTACACCTATAAAAGAGA
GAGCCGTTATCGTCTGTTTGTGGATGTACAGAGTGATATTATTGACACGCCCGGGCGACGGATGGTGATCCCCC
TGGCCAGTGCACGTCTGCTGTCAGATAAAGTCTCCCGTGAACTTTACCCGGTGGTGCATATCGGGGATGAAAGC
TGGCGCATGATGACCACCGATATGGCCAGTGTGCCGGTCTCCGTTATCGGGGAAGAAGTGGCTGATCTCAGCCA
CCGCGAAAATGACATCAAAAACGCCATTAACCTGATGTTCTGGGGAATATAAATGTCAGGCTCCCTTATACACA
GCCAGTCTGCAGGTCGACCATAGTGACTGGATATGTTGTGTTTTACAGTATTATGTAGTCTGTTTTTTATGCAA
AATCTAATTTAATATATTGATATTTATATCATTTTACGTTTCTCGTTCAGCTTTCTTGTACAAAGTGGTTGATa
tccagcacagtggcggccgcTCGAGTGGCTCGGGCTCGACCTCGGGCTCGGGCAAAACCGGTgagggcggcagc
ctggccgcgctgaccgcgcaccaggcttgccacctgccgctggagactttcacccgtcatcgccagccgcgcgg
ctgggaacaactggagcagtgcggctatccggtgcagcggctggtcgccctctacctggcggcgcggctgtcgt
ggaaccaggtcgaccaggtgatccgcaacgccctggccagccccggcagcggcggcgacctgggcgaagcgatc
cgcgagcagccggagcaggcccgtctggccctgaccctggccgccgccgagagcgagcgcttcgtccggcaggg
caccggcaacgacgaggccggcgcggccaacgccgacgtggtgagcctgacctgcccggtcgccgccggtgaat
gcgcgggcccggcggacagcggcgacgccctgctggagcgcaactatcccactggcgcggagttcctcggcgac
ggcggcgacgtcagcttcagcacccgcggcacgcagaactggacggtggagcggctgctccaggcgcaccgcca
actggaggagcgcggctatgtgttcgtcggctaccacggcaccttcctcgaagcggcgcaaagcatcgtcttcg
gcggggtgcgcgcgcgcagccaggacctcgacgcgatctggcgcggtttctatatcgccggcgatccggcgctg
gcctacggctacgcccaggaccaggaacccgacgcacgcggccggatccgcaacggtgccctgctgcgggtcta
tgtgccgcgctcgagcctgccgggcttctaccgcaccagcctgaccctggccgcgccggaggcggcgggcgagg
tcgaacggctgatcggccatccgctgccgctgcgcctggacgccatcaccggccccgaggaggaaggcgggcgc
ctggagaccattctcggctggccgctggccgagcgcaccgtggtgattccctcggcgatccccaccgacccgcg
caacgtcggcggcgacctcgacccgtccagcatccccgacaaggaacaggcgatcagcgccctgccggactacg
ccagccagcccggcaaaccgccgcgcgaggacctgaagtaaGGGCCcgtttaaacccgctgatcagcctcgact
gtgccttctagttgccagccatctgttgtttgcccctcccccgtgccttccttgaccctggaaggtgccactcc
cactgtcctttcctaataaaatgaggaaattgcatcgcattgtctgagtaggtgtcattctattctggggggtg
gggtggggcaggacagcaagggggaggattgggaagacaatagcaggcatgctggggatgcggtgggctctatg
gcttctgaggcggaaagaaccagctggggctctagggggtatccccacgcgccctgtagcggcgcattaagcgc
ggcgggtgtggtggttacgcgcagcgtgaccgctacacttgccagcgccctagcgcccgctcctttcgctttct
tcccttcctttctcgccacgttcgccggctttccccgtcaagctctaaatcgggggctccctttagggttccga
tttagtgctttacggcacctcgaccccaaaaaacttgattagggtgatggttcacgtagtgggccatcgccctg
atagacggtttttcgccctttgacgttggagtccacgttctttaatagtggactcttgttccaaactggaacaa
cactcaaccctatctcggtctattcttttgatttataagggattttgccgatttcggcctattggttaaaaaat
gagctgatttaacaaaaatttaacgcgaattaattctgtggaatgtgtgtcagttagggtgtggaaagtcccca
ggctccccagcaggcagaagtatgcaaagcatgcatctcaattagtcagcaaccaggtgtggaaagtccccagg
ctccccagcaggcagaagtatgcaaagcatgcatctcaattagtcagcaaccatagtcccgcccctaactccgc
ccatcccgcccctaactccgcccagttccgcccattctccgccccatggctgactaattttttttatttatgca
gaggccgaggccgcctctgcctctgagctattccagaagtagtgaggaggcttttttggaggcctaggcttttg
caaaaagctcccgggagcttgtatatccattttcggatctgatcagcacgtgatgaaaaagcctgaactcaccg
cgacgtctgtcgagaagtttctgatcgaaaagttcgacagcgtctccgacctgatgcagctctcggagggcgaa
gaatctcgtgctttcagcttcgatgtaggagggcgtggatatgtcctgcgggtaaatagctgcgccgatggttt
ctacaaagatcgttatgtttatcggcactttgcatcggccgcgctcccgattccggaagtgcttgacattgggg TABLE 1A-continued Sequences of plasmids aattcagcgagagcctgacctattgcatctcccgccgtgcacagggtgtcacgttgcaagacctgcctgaaacc
gaactgcccgctgttctgcagccggtcgcggaggccatggatgcgatcgctgcggccgatcttagccagacgag
cgggttcggcccattcggaccgcaaggaatcggtcaatacactacatggcgtgatttcatatgcgcgattgctg
atccccatgtgtatcactggcaaactgtgatggacgacaccgtcagtgcgtccgtcgcgcaggctctcgatgag
ctgatgctttgggccgaggactgccccgaagtccggcacctcgtgcacgcggatttcggctccaacaatgtcct
gacggacaatggccgcataacagcggtcattgactggagcgaggcgatgttcggggattcccaatacgaggtcg
ccaacatcttcttctggaggccgtggttggcttgtatggagcagcagacgcgctacttcgagcggaggcatccg
gagcttgcaggatcgccgcggctccgggcgtatatgctccgcattggtcttgaccaactctatcagagcttggt
tgacggcaatttcgatgatgcagcttgggcgcagggtcgatgcgacgcaatcgtccgatccggagccgggactg
tcgggcgtacacaaatcgcccgcagaagcgcggccgtctggaccgatggctgtgtagaagtactcgccgatagt
ggaaaccgacgccccagcactcgtccgagggcaaaggaatagcacgtgctacgagatttcgattccaccgccgc
cttctatgaaaggttgggcttcggaatcgttttccgggacgccggctggatgatcctccagcgcggggatctca
tgctggagttcttcgcccaccccaacttgtttattgcagcttataatggttacaaataaagcaatagcatcaca
aatttcacaaataaagcatttttttcactgcattctagttgtggtttgtccaaactcatcaatgtatcttatca
tgtctgtataccgtcgacctctagctagagcttggcgtaatcatggtcatagctgtttcctgtgtgaaattgtt
atccgctcacaattccacacaacatacgagccggaagcataaagtgtaaagcctggggtgcctaatgagtgagc
taactcacattaattgcgttgcgctcactgcccgctttccagtcgggaaacctgtcgtgccagctgcattaatg
aatcggccaacgcgcggggagaggcggtttgcgtattgggcgctcttccgcttcctcgctcactgactcgctgc
gctcggtcgttcggctgcggcgagcggtatcagctcactcaaaggcggtaatacggttatccacagaatcaggg
gataacgcaggaaagaacatgtgagcaaaaggccagcaaaaggccaggaaccgtaaaaaggccgcgttgctggc
gtttttccataggctccgcccccctgacgagcatcacaaaaatcgacgctcaagtcagaggtggcgaaacccga
caggactataaagataccaggcgtttccccctggaagctccctcgtgcgctctcctgttccgaccctgccgctt
accggatacctgtccgcctttctcccttcgggaagcgtggcgctttctcatagctcacgctgtaggtatctcag
ttcggtgtaggtcgttcgctccaagctgggctgtgtgcacgaaccccccgttcagcccgaccgctgcgccttat
ccggtaactatcgtcttgagtccaacccggtaagacacgacttatcgccactggcagcagccactggtaacagg
attagcagagcgaggtatgtaggcggtgctacagagttcttgaagtggtggcctaactacggctacactagaag
aacagtatttggtatctgcgctctgctgaagccagttaccttcggaaaaagagttggtagctcttgatccggca
aacaaaccaccgctggtagcggtttttttgtttgcaagcagcagattacgcgcagaaaaaaaggatctcaagaa
gatcctttgatcttttctacggggtctgacgctcagtggaacgaaaactcacgttaagggattttggtcatgag
attatcaaaaaggatcttcacctagatccttttaaattaaaaatgaagttttaaatcaatctaaagtatatatg
agtaaacttggtctgacagttaccaatgcttaatcagtgaggcacctatctcagcgatctgtctatttcgttca
tccatagttgcctgactccccgtcgtgtagataactacgatacgggagggcttaccatctggccccagtgctgc
aatgataccgcgagacccacgctcaccggctccagatttatcagcaataaaccagccagccggaagggccgagc
gcagaagtggtcctgcaactttatccgcctccatccagtctattaattgttgccgggaagctagagtaagtagt
tcgccagttaatagtttgcgcaacgttgttgccattgctacaggcatcgtggtgtcacgctcgtcgtttggtat
ggcttcattcagctccggttcccaacgatcaaggcgagttacatgatcccccatgttgtgcaaaaaagcggtta
gctccttcggtcctccgatcgttgtcagaagtaagttggccgcagtgttatcactcatggttatggcagcactg
cataattctcttactgtcatgccatccgtaagatgcttttctgtgactggtgagtactcaaccaagtcattctg
agaatagtgtatgcggcgaccgagttgctcttgcccggcgtcaatacgggataataccgcgccacatagcagaa
ctttaaaagtgctcatcattggaaaacgttcttcggggcgaaaactctcaaggatcttaccgctgttgagatcc
agttcgatgtaacccactcgtgcacccaactgatcttcagcatcttttactttcaccagcgtttctgggtgagc
aaaaacaggaaggcaaaatgccgcaaaaaagggaataagggcgacacggaaatgttgaatactcatactcttcc
tttttcaatattattgaagcatttatcagggttattgtctcatgagcggatacatatttgaatgtatttagaaa
aataaacaaataggggttccgcgcacatttccccgaaaagtgccacctgacgtc 4 SEQ ID NO: 4 nucleic acid sequence of plasmid 4 (pET15b-SHT-ccd-PE40)
ttcttgaagacgaaagggcctcgtgatacgcctatttttataggttaatgtcatgataataatggtttcttaga
cgtcaggtggcacttttcggggaaatgtgcgcggaacccctatttgtttatttttctaaatacattcaaatatg
tatccgctcatgagacaataaccctgataaatgcttcaataatattgaaaaaggaagagtatgagtattcaaca
tttccgtgtcgcccttattcccttttttgcggcattttgccttcctgtttttgctcacccagaaacgctggtga
aagtaaaagatgctgaagatcagttgggtgcacgagtgggttacatcgaactggatctcaacagcggtaagatc
cttgagagttttcgccccgaagaacgttttccaatgatgagcacttttaaagttctgctatgtggcgcggtatt
atcccgtgttgacgccgggcaagagcaactcggtcgccgcatacactattctcagaatgacttggttgagtact
caccagtcacagaaaagcatcttacggatggcatgacagtaagagaattatgcagtgctgccataaccatgagt
gataacactgcggccaacttacttctgacaacgatcggaggaccgaaggagctaaccgcttttttgcacaacat
gggggatcatgtaactcgccttgatcgttgggaaccggagctgaatgaagccataccaaacgacgagcgtgaca
ccacgatgcctgcagcaatggcaacaacgttgcgcaaactattaactggcgaactacttactctagcttcccgg
caacaattaatagactggatggaggcggataaagttgcaggaccacttctgcgctcggcccttccggctggctg
gtttattgctgataaatctggagccggtgagcgtgggtctcgcggtatcattgcagcactggggccagatggta
agccctcccgtatcgtagttatctacacgacggggagtcaggcaactatggatgaacgaaatagacagatcgct
gagataggtgcctcactgattaagcattggtaactgtcagaccaagtttactcatatatactttagattgattt
aaaacttcatttttaatttaaaaggatctaggtgaagatcctttttgataatctcatgaccaaaatcccttaac
gtgagttttcgttccactgagcgtcagaccccgtagaaaagatcaaaggatcttcttgagatcctttttttctg
cgcgtaatctgctgcttgcaaacaaaaaaaccaccgctaccagcggtggtttgtttgccggatcaagagctacc
aactctttttccgaaggtaactggcttcagcagagcgcagataccaaatactgtccttctagtgtagccgtagt
taggccaccacttcaagaactctgtagcaccgcctacatacctcgctctgctaatcctgttaccagtggctgct
gccagtggcgataagtcgtgtcttaccgggttggactcaagacgatagttaccggataaggcgcagcggtcggg
ctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaaca
ggagagcgcacgagggagcttccagggggaaacgcctggtatctttatagtcctgtcgggtttcgccacctctg
acttgagcgtcgatttttgtgatgctcgtcaggggggcggagcctatggaaaaacgccagcaacgcggcctttt
tacggttcctggccttttgctggccttttgctcacatgttctttcctgcgttatcccctgattctgtggataac
cgtattaccgcctttgagtgagctgataccgctcgccgcagccgaacgaccgagcgcagcgagtcagtgagcga
ggaagcggaagagcgcctgatgcggtattttctccttacgcatctgtgcggtatttcacaccgcatatatggtg
cactctcagtacaatctgctctgatgccgcatagttaagccagtatacactccgctatcgctacgtgactgggt
catggctgcgccccgacacccgccaacacccgctgacgcgccctgacgggcttgtctgctcccggcatccgctt
acagacaagctgtgaccgtctccgggagctgcatgtgtcagaggttttcaccgtcatcaccgaaacgcgcgagg
cagctgcggtaaagctcatcagcgtggtcgtgaagcgattcacagatgtctgcctgttcatccgcgtccagctc TABLE 1A-continued Sequences of plasmids gttgagtttctccagaagcgttaatgtctggcttctgataaagcgggccatgttaagggcggttttttcctgtt
tggtcactgatgcctccgtgtaagggggatttctgttcatgggggtaatgataccgatgaaacgagagaggatg
ctcacgatacgggttactgatgatgaacatgcccggttactggaacgttgtgagggtaaacaactggcggtatg
gatgcggcgggaccagagaaaaatcactcagggtcaatgccagcgcttcgttaatacagatgtaggtgttccac
agggtagccagcagcatcctgcgatgcagatccggaacataatggtgcagggcgctgacttccgcgtttccaga
ctttacgaaacacggaaaccgaagaccattcatgttgttgctcaggtcgcagacgttttgcagcagcagtcgct
tcacgttcgctcgcgtatcggtgattcattctgctaaccagtaaggcaaccccgccagcctagccgggtcctca
acgacaggagcacgatcatgcgcacccgtggccaggacccaacgctgcccgagatgcgccgcgtgcggctgctg
gagatggcggacgcgatggatatgttctgccaagggttggtttgcgcattcacagttctccgcaagaattgatt
ggctccaattcttggagtggtgaatccgttagcgaggtgccgccggcttccattcaggtcgaggtggcccggct
ccatgcaccgcgacgcaacgcggggaggcagacaaggtatagggcggcgcctacaatccatgccaacccgttcc
atgtgctcgccgaggcggcataaatcgccgtgacgatcagcggtccagtgatcgaagttaggctggtaagagcc
gcgagcgatccttgaagctgtccctgatggtcgtcatctacctgcctggacagcatggcctgcaacgcgggcat
cccgatgccgccggaagcgagaagaatcataatggggaaggccatccagcctcgcgtcgcgaacgccagcaaga
cgtagcccagcgcgtcggccgccatgccggcgataatggcctgcttctcgccgaaacgtttggtggcgggacca
gtgacgaaggcttgagcgagggcgtgcaagattccgaataccgcaagcgacaggccgatcatcgtcgcgctcca
gcgaaagcggtcctcgccgaaaatgacccagagcgctgccggcacctgtcctacgagttgcatgataaagaaga
cagtcataagtgcggcgacgatagtcatgccccgcgcccaccggaaggagctgactgggttgaaggctctcaag
ggcatcggtcgagatcccggtgcctaatgagtgagctaacttacattaattgcgttgcgctcactgcccgcttt
ccagtcgggaaacctgtcgtgccagctgcattaatgaatcggccaacgcgcggggagaggcggtttgcgtattg
ggcgccagggtggtttttcttttcaccagtgagacgggcaacagctgattgcccttcaccgcctggccctgaga
gagttgcagcaagcggtccacgctggtttgccccagcaggcgaaaatcctgtttgatggtggttaacggcggga
tataacatgagctgtcttcggtatcgtcgtatcccactaccgagatatccgcaccaacgcgcagcccggactcg
gtaatggcgcgcattgcgcccagcgccatctgatcgttggcaaccagcatcgcagtgggaacgatgccctcatt
cagcatttgcatggtttgttgaaaaccggacatggcactccagtcgccttcccgttccgctatcggctgaattt
gattgcgagtgagatatttatgccagccagccagacgcagacgcgccgagacagaacttaatgggcccgctaac
agcgcgatttgctggtgacccaatgcgaccagatgctccacgcccagtcgcgtaccgtcttcatgggagaaaat
aatactgttgatgggtgtctggtcagagacatcaagaaataacgccggaacattagtgcaggcagcttccacag
caatggcatcctggtcatccagcggatagttaatgatcagcccactgacgcgttgcgcgagaagattgtgcacc
gccgctttacaggcttcgacgccgcttcgttctaccatcgacaccaccacgctggcacccagttgatcggcgcg
agatttaatcgccgcgacaatttgcgacggcgcgtgcagggccagactggaggtggcaacgccaatcagcaacg
actgtttgcccgccagttgttgtgccacgcggttgggaatgtaattcagctccgccatcgccgcttccactttt
tcccgcgttttcgcagaaacgtggctggcctggttcaccacgcgggaaacggtctgataagagacaccggcata
ctctgcgacatcgtataacgttactggtttcacattcaccaccctgaattgactctcttccgggcgctatcatg
ccataccgcgaaaggttttgcgccattcgatggtgtccgggatctcgacgctctcccttatgcgactcctgcat
taggaagcagcccagtagtaggttgaggccgttgagcaccgccgccgcaaggaatggtgcatgcaaggagatgg
cgcccaacagtcccccggccacggggcctgccaccatacccacgccgaaacaagcgctcatgagcccgaagtgg
cgagcccgatcttccccatcggtgatgtcggcgatataggcgccagcaaccgcacctgtggcgccggtgatgcc
ggccacgatgcgtccggcgtagaggatcgagatctcgatcccgcgaaattaatacgactcactataggggaatt
gtgagcggataacaattcccctctagaaataattttgtttaactttaagaaggagatataccatgtggtcccat
cctcaattcgagaagcatcaccatcaccatcaccatcacggatctgaaaatctctacttccagcatacaagttt
gtacaaaaaagctgaacgagaaacgtaaaatgatataaatatcaatatattaaattagattttgcataaaaaac
agactacataatactgtaaaacacaacatatccagtcactatggcggccgcattaggcaccccaggctttacac
tttatgcttccggctcgtataatgtgtggattttgagttaggatccgtcgagattttcagga 5 SEQ ID NO: 5 nucleic acid sequence of plasmid 5 (pcDNA3.1-ccdB-PE38-6xHis)
gttaggcgttttgcgctgcttcgcgatgtacgggccagatatacgcgttgacattgattattgactagttatta
atagtaatcaattacggggtcattagttcatagcccatatatggagttccgcgttacataacttacggtaaatg
gcccgcctggctgaccgcccaacgacccccgcccattgacgtcaataatgacgtatgttcccatagtaacgcca
atagggactttccattgacgtcaatgggtggagtatttacggtaaactgcccacttggcagtacatcaagtgta
tcatatgccaagtacgccccctattgacgtcaatgacggtaaatggcccgcctggcattatgcccagtacatga
ccttatgggactttcctacttggcagtacatctacgtattagtcatcgctattaccatggtgatgcggttttgg
cagtacatcaatgggcgtggatagcggtttgactcacggggatttccaagtctccaccccattgacgtcaatgg
gagtttgttttggcaccaaaatcaacgggactttccaaaatgtcgtaacaactccgccccattgacgcaaatgg
gcggtaggcgtgtacggtgggaggtctatataagcagagctcgtttagtgaaccgtcagatcgcctggagacgc
catccacgctgttttgacctccatagaagacaccgggaccgatccagcctccggactctagaggatcgaaccct
tgaattcacaagtttgtacaaaaaagctgaacgagaaacgtaaaatgatataaatatcaatatattaaattaga
ttttgcataaaaaacagactacataatactgtaaaacacaacatatccagtcactatggcggccgcattaggca
ccccaggctttacactttatgcttccggctcgtataatgtgtggattttgagttaggatccgtcgagattttca
ggagctaaggaagctaaaatggagaaaaaaatcactggatataccaccgttgatatatcccaatggcatcgtaa
agaacattttgaggcatttcagtcagttgctcaatgtacctataaccagaccgttcagctggatattacggcct
ttttaaagaccgtaaagaaaaataagcacaagttttatccggcctttattcacattcttgcccgcctgatgaat
gctcatccggaattccgtatggcaatgaaagacggtgagctggtgatatgggatagtgttcacccttgttacac
cgttttccatgagcaaactgaaacgttttcatcgctctggagtgaataccacgacgatttccggcagtttctac
acatatattcgcaagatgtggcgtgttacggtgaaaacctggcctatttccctaaagggtttattgagaatatg
tttttcgtctcagccaatccctgggtgagtttcaccagttttgatttaaacgtggccaatatggacaacttctt
cgcccccgttttcaccatgggcaaatattatacgcaaggcgacaaggtgctgatgccgctggcgattcaggttc
atcatgccgtttgtgatggcttccatgtcggcagaatgcttaatgaattacaacagtactgcgatgagtggcag
ggcggggcgtaaagatctggatccggcttactaaaagccagataacagtatgcgtatttgcgcgctgatttttg
cggtataagaatatatactgatatgtatacccgaagtatgtcaaaaagaggtatgctatgaagcagcgtattac
agtgacagttgacagcgacagctatcagttgctcaaggcatatatgatgtcaatatctccggtctggtaagcac
aaccatgcagaatgaagcccgtcgtctgcgtgccgaacgctggaaagcggaaaatcaggaagggatggctgagg
tcgcccggtttattgaaatgaacggctcttttgctgacgagaacaggggctggtgaaatgcagtttaaggttta
cacctataaaagagagagccgttatcgtctgtttgtggatgtacagagtgatattattgacacgcccgggcgac
ggatggtgatccccctggccagtgcacgtctgctgtcagataaagtctcccgtgaactttacccggtggtgcat
atcggggatgaaagctggcgcatgatgaccaccgatatggccagtgtgccggtctccgttatcggggaagaagt
ggctgatctcagccaccgcgaaaatgacatcaaaaacgccattaacctgatgttctggggaatataaatgtcag
gctcccttatacacagccagtctgcaggtcgaccatagtgactggatatgttgtgttttacagtattatgtagt TABLE 1A-continued

| Sequences of plasmids |
|---|
| ctgtttttatgcaaaatctaatttaatatattgatatttatatcattttacgtttctcgttcagctttcttgt<br>acaaagtggttgatggggtggcggatccaccggtgcaagtggcggacctgagggcggatctcttgctgcgctc<br>acagctcatcaagcttgtcatctgcctcttgaaacgtttaccagacatcgccagccacggggatgggaacagct<br>ggagcagtgtggatatccggtgcagagacttgtggctctttacttggcggcccggctttcctggaaccaagtgg<br>atcaagtcataaggaatgcattggcttcacctgggagcggtggtgacttgggggaagctataagagaacagccc<br>gaacaggcacgccttgcgcttacattggcagcggcagagagcgagaggttcgtaagacaaggtacgggaaatga<br>tgaagcgggagcagccaatgggcccgcagattctggtgatgcacttttggagcggaactatcctaccggagcgg<br>agtttctgggtgacggaggtgacgtatcattcagtactcgcgggacccaga<br>attggacagttgagcggctcctgcaggcacacaggcaactcgaagagcggggatacgtctttgttggatatcac<br>ggtacctttcttgaggcagcgcagtcaatagtgtttggcggtgtgcgagcaagatctcaggatctcgacgctat<br>ttggaggggcttttacatagcaggggaccctgctttggcctacggctatgcccaagatcaggagcccgatgctc<br>ggggacggataaggaatggggcgctcctccgagtctatgttcctcgatcttccctgccagggttctaccgaaca<br>agtttgacacttgcggccccggaagcggccggtgaggtagagcggttgattggacatcctcttcccttgcggtt<br>ggatgccatcacggggcccgaggaagagggggtagactggagacaatcttggggtggccactcgcagagcgga<br>cggtggtgattccatcagcgatccccaccgatccgcgcaatgtgggcggggatttggatccttcttctatacct<br>gacaaggagcaggcgatctccgccttgcccgattacgcaagtcaaccaggtaagccgcctcaccaccatcatca<br>ccatcgggaagacctgaagtaagggccctagtaatgagtttgatatctcgacaatcaacctctggattacaaaa<br>tttgtgaaagattgactggtattcttaactatgttgctccttttacgctatgtggatacgctgctttaatgcct<br>ttgtatcatgctattgcttcccgtatggctttcattttctcctccttgtataaatcctggttgctgtctcttta<br>tgaggagttgtggcccgttgtcaggcaacgtggcgtggtgtgcactgtgtttgctgacgcaacccccactggtt<br>ggggcattgccaccacctgtcagctcctttccgggactttcgctttccccctccctattgccacggcggaactc<br>atcgccgcctgccttgcccgctgctggacaggggctcggctgttgggcactgacaattccgtggtgttgtcggg<br>gaagctgacgtcctttccatggctgctcgcctgtgttgccacctggattctgcgcgggacgtccttctgctacg<br>tcccttcggccctcaatccagcggaccttccttcccgcggcctgctgccggctctgcggcctcttccgcgtctt<br>cgccttcgccctcagacgagtcggatctccctttgggccgcctccccgcctggaacggggaggctaactgaaa<br>cacggaaggagacaataccggaaggaacccgcgctatgacggcaataaaaagacagaataaaacgcacgggtgt<br>tgggtcgtttgttcataaacgcggggttcggtcccagggctggcactctgtcgataccccaccgagaccccatt<br>ggggccaatacgcccgcgtttcttccttttccccaccccaccccccaagttcgggtgaaggcccagggctcgca<br>gccaacgtcggggcggcaggccctgccatagcagatctgcgcagctggggctctaggggggtatccccacgcgcc<br>ctgtagcggcgcattaagcgcggcgggtgtggtggttacgcgcagcgtgaccgctacacttgccagcgccctag<br>cgcccgctcctttcgctttcttcccttcctttctcgccacgttcgccggctttccccgtcaagctctaaatcgg<br>gggctccctttagggttccgatttagtgctttacggcacctcgaccccaaaaaacttgattagggtgatggttc<br>acgtagtgggccatcgccctgatagacggtttttcgccctttgacgttggagtccacgttctttaatagtggac<br>tcttgttccaaactggaacaacactcaaccctatctcggtctattcttttgatttataagggattttgccgatt<br>tcggcctattggttaaaaaatgagctgatttaacaaaaatttaacgcgaattaattctgtggaatgtgtgtcag<br>ttagggtgtggaaagtccccaggctccccagcaggcagaagtatgcaaagcatgcatctcaattagtcagcaac<br>caggtgtggaaagtccccaggctccccagcaggcagaagtatgcaaagcatgcatctcaattagtcagcaacca<br>tagtcccgcccctaactccgcccatcccgcccctaactccgcccagttccgcccattctccgccccatggctga<br>ctaattttttttatttatgcagaggccgaggccgcctctgcctctgagctattccagaagtagtgaggaggctt<br>ttttggaggcctaggcttttgcaaaaagctcccgggagcttgtatatccattttcggatctgatcaagagacag<br>gatgaggatcgtttcgcatgattgaacaagatggattgcacgcaggttctccggccgcttgggtggagaggcta<br>ttcggctatgactgggcacaacagacaatcggctgctctgatgccgccgtgttccggctgtcagcgcaggggcg<br>cccggttctttttgtcaagaccgacctgtccggtgccctgaatgaactgcaggacgaggcagcgcggctatcgt<br>ggctggccacgacgggcgttccttgcgcagctgtgctcgacgttgtcactgaagcgggaagggactggctgcta<br>ttgggcgaagtgccggggcaggatctcctgtcatctcaccttgctcctgccgagaaagtatccatcatggctga<br>tgcaatgcggcggctgcatacgcttgatccggctacctgcccattcgaccaccaagcgaaacatcgcatcgagc<br>gagcacgtactcggatggaagccggtcttgtcgatcaggatgatctggacgaagagcatcaggggctcgcgcca<br>gccgaactgttcgccaggctcaaggcgcgcatgcccgacggcgaggatctcgtcgtgacccatggcgatgcctg<br>cttgccgaatatcatggtggaaaatggccgcttttctggattcatcgactgtggccggctgggtgtggcggacc<br>gctatcaggacatagcgttggctacccgtgatattgctgaagagcttggcggcgaatgggctgaccgcttcctc<br>gtgctttacggtatcgccgctcccgattcgcagcgcatcgccttctatcgccttcttgacgagttcttctgagc<br>gggactctggggttcgcgaaatgaccgaccaagcgacgcccaacctgccatcacgagatttcgattccaccgcc<br>gccttctatgaaaggttgggcttcggaatcgttttccgggacgccggctggatgatcctccagcgcggggatct<br>catgctggagttcttcgcccaccccaacttgtttattgcagcttataatggttacaaataaagcaatagcatca<br>caaatttcacaaataaagcatttttttcactgcattctagttgtggtttgtccaaactcatcaatgtatcttat<br>catgtctgtataccgtcgacctctagctagagcttggcgtaatcatggtcatagctgtttcctgtgtgaaattg<br>ttatccgctcacaattccacacaacatacgagccggaagcataaagtgtaaagcctggggtgcctaatgagtga<br>gctaactcacattaattgcgttgcgctcactgcccgctttccagtcgggaaacctgtcgtgccagctgcattaa<br>tgaatcggccaacgcgcggggagaggcggtttgcgtattgggcgctcttccgcttcctcgctcactgactcgct<br>gcgctcggtcgttcggctgcggcgagcggtatcagctcactcaaaggcggtaatacggttatccacagaatcag<br>gggataacgcaggaaagaacatgtgagcaaaaggccagcaaaaggccaggaaccgtaaaaaggccgcgttgctg<br>gcgtttttccataggctccgcccccctgacgagcatcacaaaaatcgacgctcaagtcagaggtggcgaaaccc<br>gacaggactataaagataccaggcgtttccccctggaagctccctcgtgcgctctcctgttccgaccctgccgc<br>ttaccggatacctgtccgcctttctcccttcgggaagcgtggcgctttctcatagctcacgctgtaggtatctc<br>agttcggtgtaggtcgttcgctccaagctgggctgtgtgcacgaaccccccgttcagcccgaccgctgcgcctt<br>atccggtaactatcgtcttgagtccaacccggtaagacacgacttatcgccactggcagcagccactggtaaca<br>ggattagcagagcgaggtatgtaggcggtgctacagagttcttgaagtggtggcctaactacggctacactaga<br>agaacagtatttggtatctgcgctctgctgaagccagttaccttcggaaaaagagttggtagctcttgatccgg<br>caaacaaaccaccgctggtagcggtggtttttttgtttgcaagcagcagattacgcgcagaaaaaaaggatctc<br>aagaagatcctttgatcttttctacggggtctgacgctcagtggaacgaaaactcacgttaagggattttggtc<br>atgagattatcaaaaaggatcttcacctagatccttttaaattaaaaatgaagttttaaatcaatctaaagtat<br>atatgagtaaacttggtctgacagttaccaatgcttaatcagtgaggcacctatctcagcgatctgtctatttc<br>gttcatccatagttgcctgactccccgtcgtgtagataactacgatacgggagggcttaccatctggccccagt<br>gctgcaatgataccgcgagacccacgctcaccggctccagatttatcagcaataaaccagccagccggaagggc<br>cgagcgcagaagtggtcctgcaactttatccgcctccatccagtctattaattgttgccgggaagctagagtaa<br>gtagttcgccagttaatagtttgcgcaacgttgttgccattgctacaggcatcgtggtgtcacgctcgtcgttt<br>ggtatggcttcattcagctccggttcccaacgatcaaggcgagttacatgatcccccatgttgtgcaaaaaagc<br>ggttagctccttcggtcctccgatcgttgtcagaagtaagttggccgcagtgttatcactcatggttatggcag |

TABLE 1A-continued

| Sequences of plasmids |
|---|
| cactgcataattctcttactgtcatgccatccgtaagatgcttttctgtgactggtgagtactcaaccaagtca ttctgagaatagtgtatgcggcgaccgagttgctcttgcccggcgtcaatacgggataataccgcgccacatag cagaactttaaaagtgctcatcattggaaaacgttcttcggggcgaaaactctcaaggatcttaccgctgttga gatccagttcgatgtaacccactcgtgcacccaactgatcttcagcatcttttactttcaccagcgtttctggg tgagcaaaaacaggaaggcaaaatgccgcaaaaaagggaataagggcgacacggaaatgttgaatactcatact cttcctttttcaatattattgaagcatttatcagggttattgtctcatgagcggatacatatttgaatgtattt agaaaaataaacaaataggggttccgcgcacatttccccgaaaagtgccacctgacgtcgacggatcgggagat ctcccgatcccctatggtcgactctcagtacaatctgctctgatgccgcatagttaagccagtatctgctccct gcttgtgtgttggaggtcgctgagtagtgcgcgagcaaaatttaagctacaacaaggcaaggcttgaccgacaa ttgcatgaagaatctgcttagg |

TABLE 1B

| Sequences of CRISPR-Cas PAM, target sites and gRNAs | |
|---|---|
| SEQ ID NO: 6 type II CRISPR-Casprotospacer-adjacent motif (PAM) | ngg |
| SEQ ID NO: 7 type II CRISPR-Cas target site sequence with protospacer-adjacent motif (PAM) | nnnnnnnnnnnnnn nnnnnngg |
| SEQ ID NO: 8 type V CRISPR-Cas protospacer-adjacent motif (PAM) | ttty |
| SEQ ID NO: 9 type V CRISPR-Cas target site sequence with protospacer-adjacent motif(PAM) | tttvnnnnnnnnnnnnnnn nnnnnnnn |
| SEQ ID NO: 10 tracrRNA | gtttcagagctatgctgga aacagcatagcaagttgaa ataaggctagtccgttatc aacttgaaaaagtggcacc gagtcggtgc |
| SEQ ID NO: 11 direct repeat for Lachnospiraceae bacterium Cpf1 | taatttctactcttgtagat |
| SEQ ID NO: 12 direct repeat for *Acidaminococcus* sp. Cpf1 | taatttctactaagtg tagat |
| SEQ ID NO: 13 DPH1 gRNA | tccagcacccacctctgcca |
| SEQ ID NO: 14 DPH1 gRNA | gtggccttgcaaatgccgga, |
| SEQ ID NO: 15 DPH1 gRNA | tgtggatgacttcacagcga |
| SEQ ID NO: 16 DPH1 gRNA | aatggtgctgaccagggcaa |
| SEQ ID NO: 17 DPH2 gRNA | gatgtttagcagccctgccg |
| SEQ ID NO: 18 DPH2 gRNA | tgggtgacacagcctacggc |
| SEQ ID NO: 19 DPH2 gRNA | agaacgttgacgaagcacga |
| SEQ ID NO: 20 DPH2 gRNA | gagggccagagatgcccgcg |
| SEQ ID NO: 21 DPH3 gRNA | agataacttctccatcacca |
| SEQ ID NO: 22 DPH3 gRNA | atggagaagttatctccaca |
| SEQ ID NO: 23 DPH3 gRNA | tggagaagttatctccacat |
| SEQ ID NO: 24 DPH3 gRNA | ctcgtcatgaaacactgcca |
| SEQ ID NO: 25 DPH5 gRNA | caaatggatcaccaaccaca |
| SEQ ID NO: 26 DPH5 gRNA | tggtttacactcatataccg |

TABLE 1B -continued

| Sequences of CRISPR-Cas PAM, target sites and gRNAs | |
|---|---|
| SEQ ID NO: 27 DPH5 gRNA | tttacactcatataccgtgg |
| SEQ ID NO: 28 DPH5 gRNA | aggaggcagcatacatccaa |
| SEQ ID NO: 29 DPH7 gRNA | gcgggacctaccagctgcgg |
| SEQ ID NO: 30 DPH7 gRNA | agacggcctaaacggacctg |
| SEQ ID NO: 31 DPH7 gRNA | agccagacactgctcctcca |
| SEQ ID NO: 32 DPH7 gRNA | cctcaggtgtcacatcccgg |
| SEQ ID NO: 33 DNAJC24 gRNA | aaaggattggtacagcatcc |
| SEQ ID NO: 34 DNAJC24 gRNA | ttgcagatgggtctgctccc |
| SEQ ID NO: 35 DNAJC24 gRNA | caaagtacagatgtaccagc |
| SEQ ID NO: 36 DNAJC24 gRNA | agatgtaccagcaggaacag |
| SEQ ID NO: 37 HBEGF gRNA | aagagcttcagcaccaccga |
| SEQ ID NO: 38 HBEGF gRNA | ggtccgtggatacagtggga |
| SEQ ID NO: 39 HBEGF gRNA | tcatgggctgagcctcccag |
| SEQ ID NO: 40 HBEGF gRNA | actggccacaccaaacaagg |
| SEQ ID NO: 41 FURIN gRNA | gaaggtcttcaccaacacgt |
| SEQ ID NO: 42 FURIN gRNA | tctgcagccggctgtgccgc |
| SEQ ID NO: 43 FURIN gRNA | gtggtctccattctggacga |
| SEQ ID NO: 44 FURIN gRNA | gcacggcacacggtgtgcgg |
| SEQ ID NO: 45 MESDC2 gRNA | tcgcgatgggagctacgcct |
| SEQ ID NO: 46 MESDC2 gRNA | agaggcacaaagcaggacca |
| SEQ ID NO: 47 MESDC2 gRNA | gaaattacgagcctctggca |
| SEQ ID NO: 48 MESDC2 gRNA | gctatcttcatgcttcgcga |
| SEQ ID NO: 49 LRP1 gRNA | gcgaccagagctgagagcag |
| SEQ ID NO: 50 LRP1 gRNA | gcggaactcgcccacaccac |
| SEQ ID NO: 51 LRP1 gRNA | agtgagttccgctgtgccaa |
| SEQ ID NO: 52 LRP1 gRNA | tgtggacgagttccgctgca |

TABLE 1B -continued

| Sequences of CRISPR-Cas PAM, target sites and gRNAs | |
|---|---|
| SEQ ID NO: 53 LRP1B gRNA | attgccagggtgctgaccgt |
| SEQ ID NO: 54 LRP1B gRNA | gacgaaggagtacattgtca |
| SEQ ID NO: 55 LRP1B gRNA | ggtgacacatacagaaccgt |
| SEQ ID NO: 56 LRP1B gRNA | cgtgaaagtctaaagcacga |

Making a Toxin Resistant Cell Line

Because producing a toxin in wild-type mammalian cells would be toxic to the producing cell itself, the inventors first generated a cell line that is resistant to Diphtheria toxin A (DTA) and *Pseudomonas* exotoxin A (PE). To do so, CRISPR/Cas9 was used to knock out DNAJC24, a gene required for intoxication by these toxins.

HEK-293T cells were transiently transfected with PX459 plasmid encoding a gRNA targeting DNAJC24 and Cas9. Transfected cells were treated with PE (12 nM final) for two days. Survived cells (DNAJC24 KO) were allowed to repopulate for two more days and used for subsequent toxin production.

Production of Recombinant Toxin Fusions in Mammalian Cells and Bacterial Cells

Figure 7:
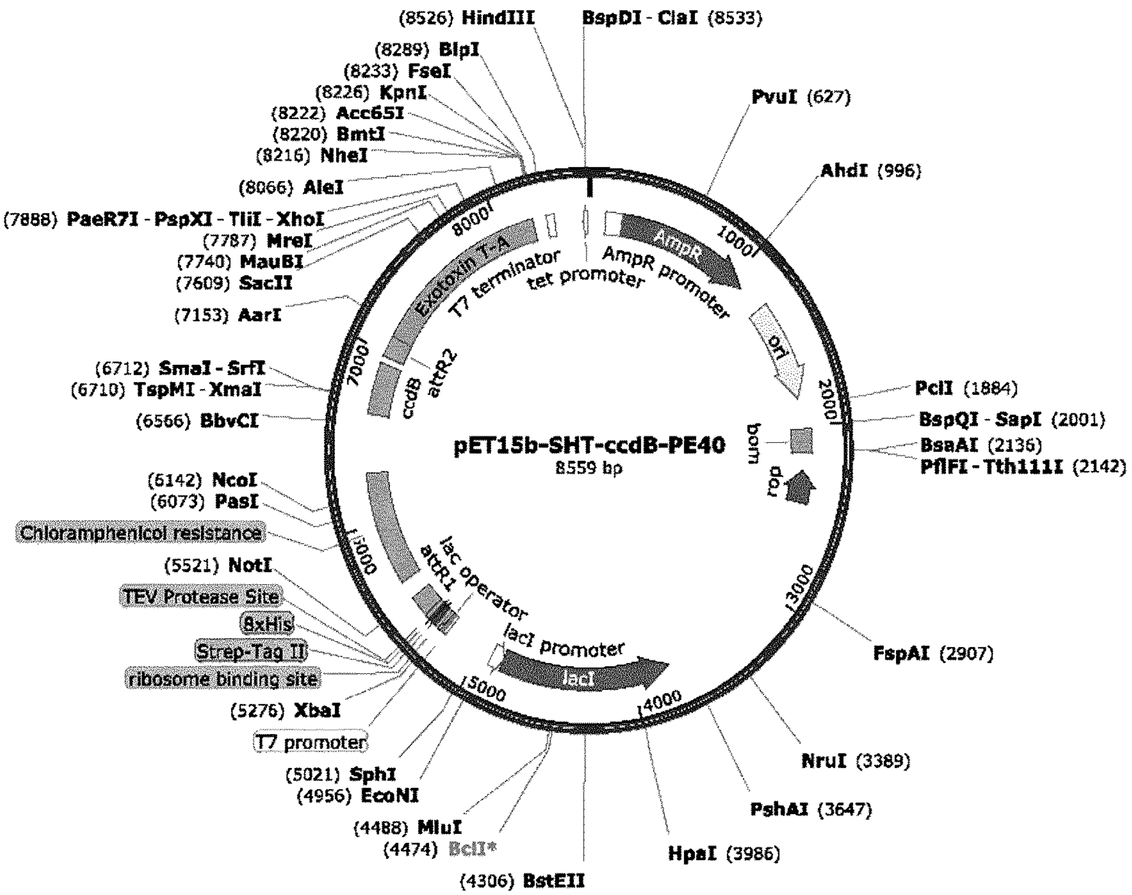
FIG. 7 shows representative images of HAP1 cells treated with Diphtheria toxin or *Pseudomonas* Exotoxin A following CRISPR screening with genome-wide gRNA library.

DNAJC24 KO cells were transfected with a plasmid encoding a secreted wild type or recombinant toxin fusion (for example, pcDNA3.1-SP-DTA-GS-ccdB and pcDNA3.1-SP-codB-GSlinker-PE40 (see FIG. 4 and FIG. 6)) using Lipofectamine® 2000. 24 hours post-transfection, the media were replenished and the cells were further cultured for two more days. 72 hours post-transfection, conditioned media containing a secreted toxin were collected, centrifuged at 1,000 rpm for 5 minutes and applied to the target cells. Recombinant toxin fusion can also be produced bacterially by transforming suitable host bacterial cells with plasmids, for example pET15b-SHT-SUMO-DTA-ccdB (FIG. 5) and pET15b-SHT-ccdB-PE40 (FIG. 7). In short, recombinant toxin fusions were expressed in BL21 (pLysS) cells and induced with 0.5 mM IPTG for 16 hours at 18° C. Toxin fusion proteins were purified from the bacterial lysate with Ni-NTA beads and eluted with 250 mM imidazole. Centrifugal columns were used to concentrate the protein and exchange the buffer to 1×PBS.

Generation of Genome-Wide Knock-Out Cells

HAP1, HeLa-Kyoto and HEK-293T cells were each seeded for lentiviral transduction. TKOv3 lentivirus (70,000 guides) were added at MOI of 0.3 to ensure single infection per cell. The skilled person recognizes that higher MOI may still provide infection, and MOI can be lower if there are more initial cells to be infected. Transduced cells were selected with puromycin (1.5 ug/ml final) for two days. The transduced cells were either passaged for downstream screening or frozen for future use. For HAP1 cells, insertional mutagenesis with retroviruses or transposons are also useful. For example, transposon insertion mutagenesis using for example the Piggyback system.

CRISPR Screening with Recombinant Toxin Fusions 6 million transduced cells were seeded in two 10 cm plates (3 million cells each at $T_0$ and were maintained until $T_5$, i.e. day 5 of transduction. This cell number reflects 85× coverage of the TKOv3 library. Cells were treated with conditioned media containing toxin at a ratio of 0.9:2 (i.e. 4.5 ml of conditioned media+10 ml of culture media) at $T_6$. At $T_8$, cells were washed and allowed to repopulate to 100% confluency without additional toxin treatments.

Alternatively, for HAP1 and HEK293T cells, 3.4 million transduced cells could be seeded in 10 cm plates to provide 50× coverage of the TKOv3 library. Next-generation sequencing and analysis Toxin resistant cells were collected by trypsinization and centrifugation for genomic DNA extraction. Genomic DNA were extracted using QIAamp blood maxi kit using the manufacturer's protocols. Extracted genomic DNA was used as a template for the downstream PCR to amplify gRNA encoding regions. Amplified gRNA regions were further barcoded with unique sequences for next-generation sequencing.

Analysis

Next-generation sequencing results were analyzed using MAGeCK package as described in Li et al (2014). In brief, the read counts for each gRNA were obtained and normalized by comparing it to the toxin untreated control population. MAGeCK first calculates individual gRNAs based on the enrichment score and ranks significantly enriched genes. Seeking for a screen-specific plasma membrane protein among the top-enriched genes identifies the receptor for a given ligand. Q-values reported hereinbelow are also referred to as adjusted p-values.

Results

Figure 8:
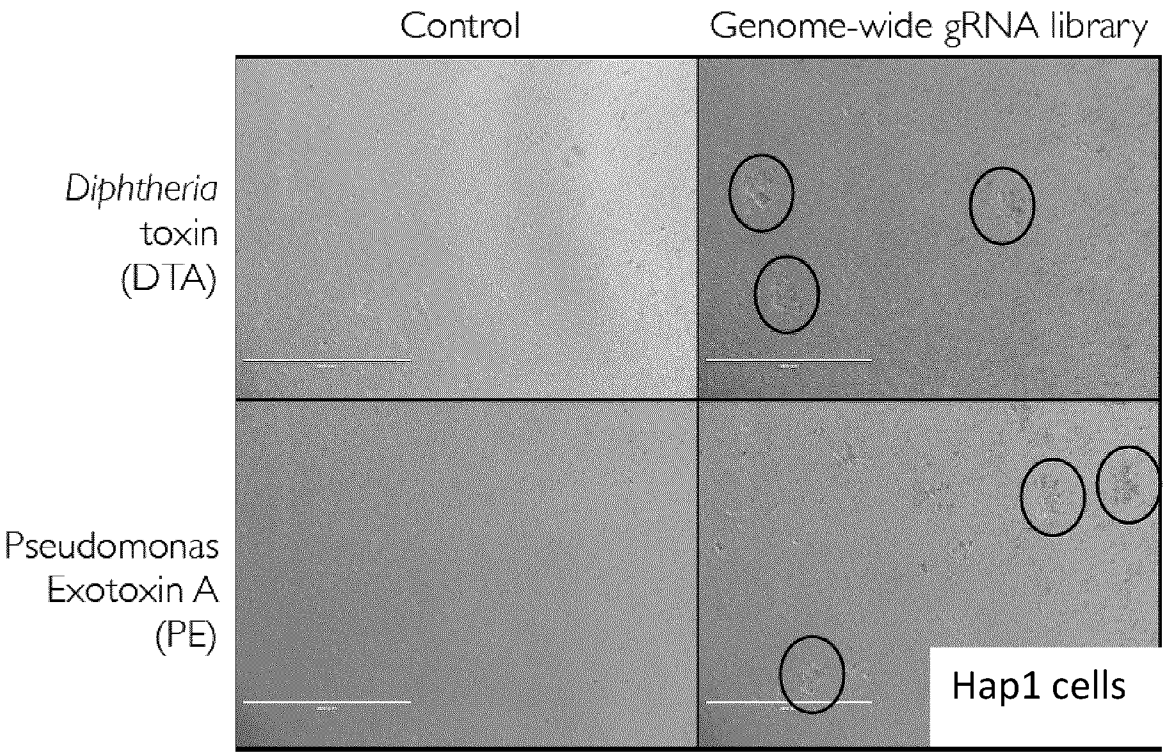
FIG. 8 shows a schematic diagram of destination plasmid pcDNA3.1-SP-DTA-GS-ccdB for mammalian expression of Diphtheria toxin-ligands.
Figure 9:
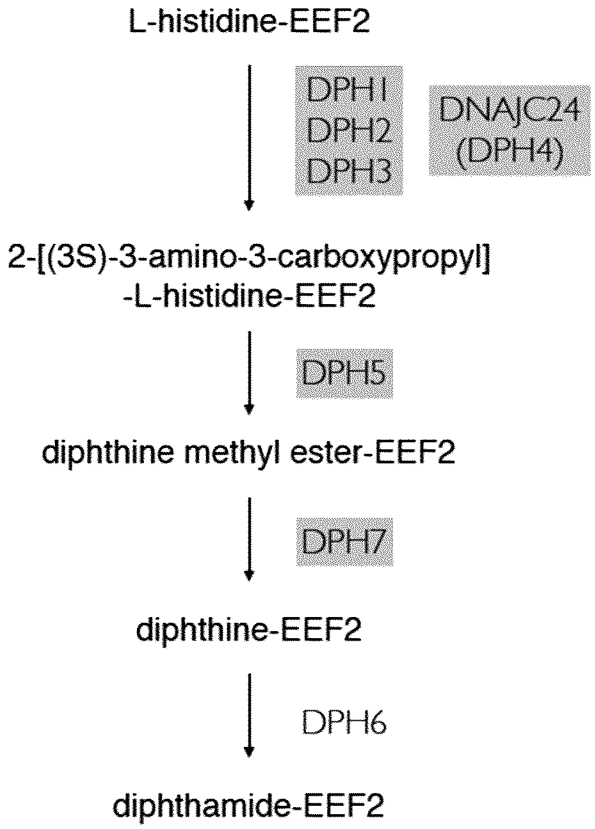
FIG. 9 shows a pathway for diphthamide synthesis.

The inventors performed genome-wide CRISPR/Cas9 screens for factors that confer resistance to native PE and DTA in human haploid HAP1 cells, using genome-wide lentiviral gRNA library (FIG. 8). These screens revealed three types of hits. First, the inventors identified the DTA receptor HBEGF and PE receptor LRP1 among the top hits in the screen, confirming the key principle of the presently disclosed approach (FIG. 9; Table 2 and Table 3).

TABLE 2

List of genes that confers resistance to *Diphtheria* toxin from a CRISPR screen. HBEGF is a DTA receptor. DPH1, DPH2, DPH3, DPH5, DPH7, and DNAJC24 are involved in diphthamide biosynthesis.

*Diphtheria* toxin, $GI_{100}$

| Gene | Rank | Adjusted p-value |
|---|---|---|
| HBEGF | 1 | 3.95E−147 |
| DPH7 | 2 | 2.03E−128 |
| DPH1 | 3 | 2.43E−126 |
| DPH2 | 4 | 6.22E−123 |
| DNAJC24 | 5 | 2.86E−113 |
| DPH5 | 6 | 1.47E−94 |
| DPH3 | 7 | 1.01E−30 |
| ZMYND19 | 8 | 1.89E−23 |
| OVCA2 | 9 | 3.05E−20 |
| HES2 | 10 | 4.40E−19 |

TABLE 3

List of genes that confers resistance to *Pseudomonas* Exotoxin A from a CRISPR screen. FURIN is involved in exotoxin A cleavage. DPH1, DPH2, DPH5, DPH6, DPH7, and DNAJC24 are involved in diphthamide biosynthesis. MESDC2 is a receptor chaperone. LRP1 is a receptor for *Pseudomonas* exotoxin. $GI_{100}$ is complete inhibition of cell growth.

*Pseudomonas* exotoxin A, $GI_{100}$

| Gene | Rank | q-value |
|---|---|---|
| FURIN | 1 | 8.54E−65 |
| DPH7 | 2 | 1.88E−64 |
| DNAJC24 | 3 | 1.58E−60 |
| DPH2 | 4 | 6.73E−58 |

TABLE 3-continued

List of genes that confers resistance to *Pseudomonas* Exotoxin A from a CRISPR screen. FURIN is involved in exotoxin A cleavage. DPH1, DPH2, DPH5, DPH6, DPH7, and DNAJC24 are involved in diphthamide biosynthesis. MESDC2 is a receptor chaperone. LRP1 is a receptor for *Pseudomonas* exotoxin. $GI_{100}$ is complete inhibition of cell growth.

| *Pseudomonas* exotoxin A, $GI_{100}$ | | |
|---|---|---|
| Gene | Rank | q-value |
| DPH1 | 5 | 1.29E−57 |
| HSP90B1 | 6 | 6.88E−51 |
| MESDC2 | 7 | 2.86E−48 |
| DPH5 | 8 | 3.11E−44 |
| ATP2C1 | 9 | 3.65E−42 |
| DPH6 | 10 | 5.46E−28 |
| KIAA0196 | 11 | 9.46E−28 |
| VPS53 | 12 | 1.22E−27 |
| CCDC93 | 13 | 1.73E−26 |
| SNX17 | 14 | 1.20E−25 |
| CCDC22 | 15 | 2.64E−25 |
| LRP1 | 35 | 8.22E−15 |

Figure 10:
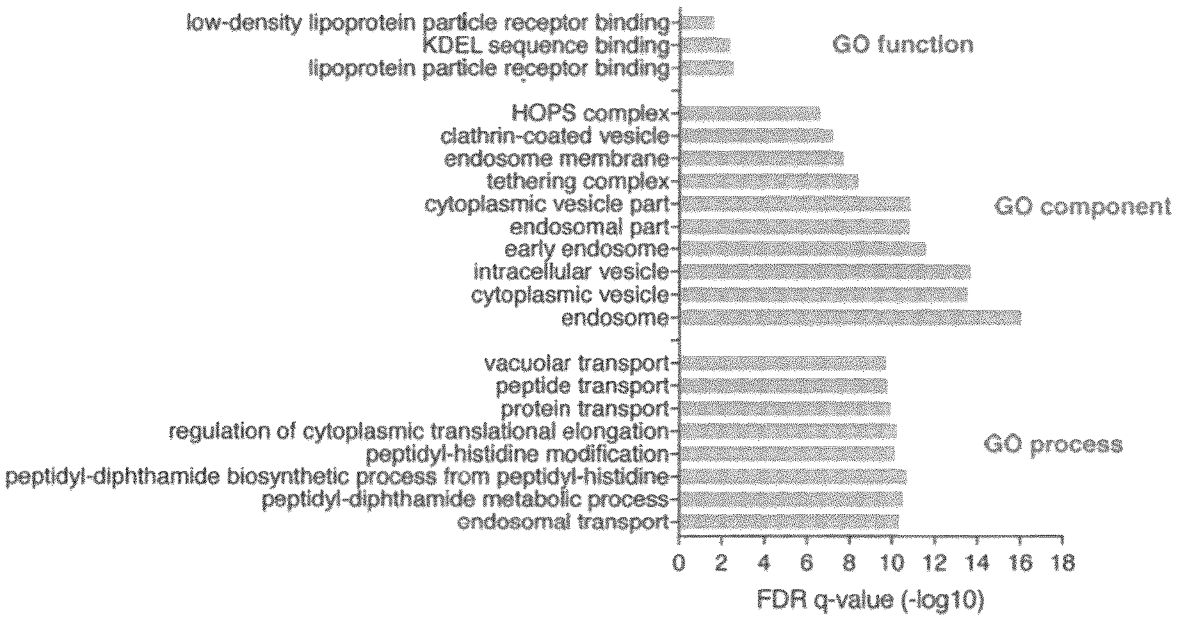
FIG. 10 shows a list of genes that is required for intoxication by *Pseudomonas* exotoxin A.

Second, the PE screen also identified the ER chaperone MESDC2, which is specifically required for trafficking of LRP family receptors to the plasma membrane (Table 3). This demonstrates that the presently disclosed methods identify critical components of the receptor signaling pathway. Finally, the inventors identified general factors required for PE and DTA intoxication. These hits, along with the genes required for intoxication by DTA shown in FIG. 10, serve as positive controls in every screen, as they regulate intoxication independently of the targeting moiety.

Figure 11A:
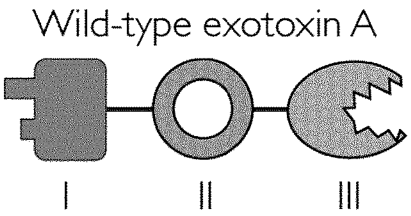
FIG. 11A-C show a model of wild-type *Pseudomonas* Exotoxin A (PE) (A), recombinant toxin EGF-PE38 (EGF-PE) having translocation (B) and toxin domain of PE and a binding domain comprising the ligand EGF, and a schematic diagram of production and application of recombinant toxin EGF-PE38 (C). I: receptor-binding molecule (binding domain); II: translocation domain; III: toxin domain. In (B) the binding domain is EGF.
Figure 11B:
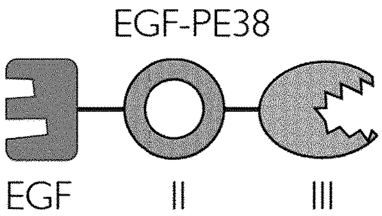
Figure 11C:
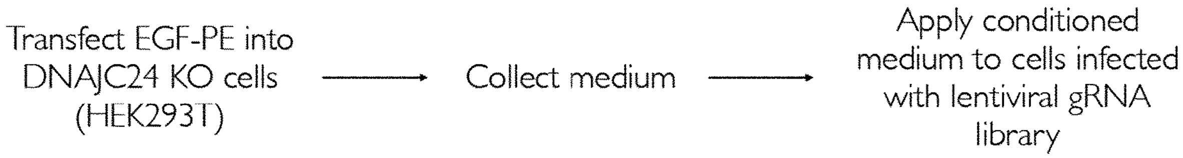
Figure 12:
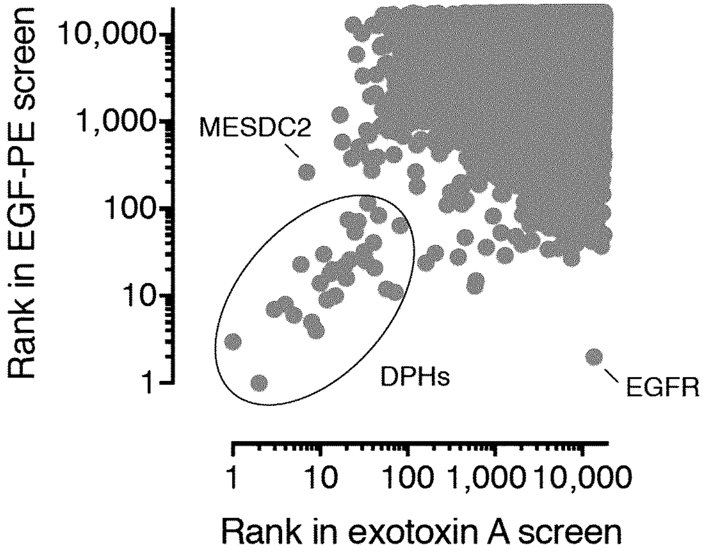
FIG. 12 shows graphical results from a screen using EGF-PE.

To demonstrate that the presently disclosed methods can identify the receptor for a recombinant toxin fusion comprising a receptor-binding molecule, for example a ligand such as a secreted protein, fused to exotoxin, a genome-wide CRISPR/Cas9 screen was performed in HeLa cells with EGF-PE (the ligand epidermal growth factor (EGF) fused to PE translocation and toxin domain; FIG. 11). The second highest hit in the screen was EGFR, the known cognate receptor for EGF, validating the presently disclosed platform (Table 4).

TABLE 4

List of genes that confers resistance to EGF-PE38 from a CRISPR screen in HeLa cells. EGFR is a receptor for EGF. DPH1, DPH2, DPH5, and DNAJC24 are involved in diphthamide biosynthesis.

| EGF-PE38 | | |
|---|---|---|
| Gene | Rank | q-value |
| DPH7 | 1 | 0.000152 |
| EGFR | 2 | 0.00393 |
| FURIN | 3 | 0.00551 |
| ATP2C1 | 4 | 0.00633 |
| DPH5 | 5 | 0.00824 |
| DPH1 | 6 | 0.0234 |
| DNAJC24 | 7 | 0.0329 |
| DPH2 | 8 | 0.0595 |
| VPS53 | 9 | 0.053 |
| CCDC22 | 10 | 0.0836 |

Figure 13A:
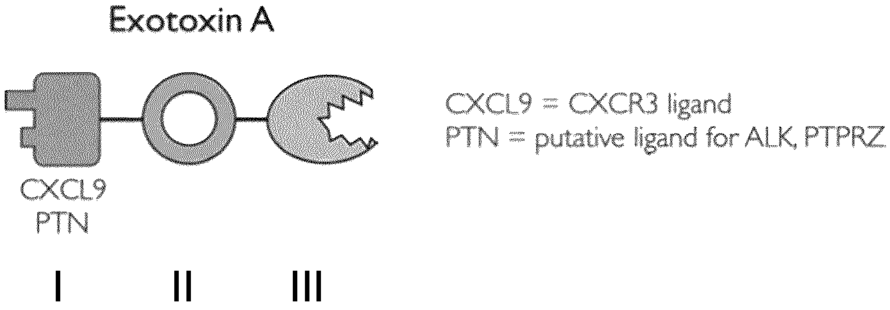
FIG. 13A shows a schematic diagram of recombinant ligand-conjugated toxins comprising translocation and toxin domain of PE, and a binding domain of CXCL9 or PTN, which are receptor-binding molecules.
Figure 13B:
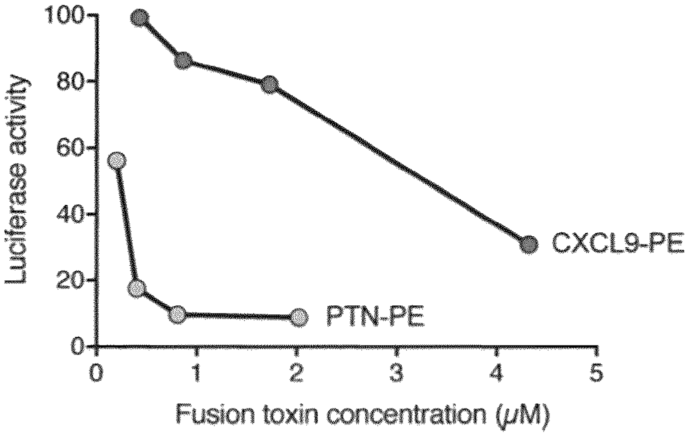
FIG. 13B shows a graph showing different toxic effects of PTN-PE and CXCL9-PE on HEK293T cells I. binding domain of CXCL9 or PTN; II: translocation domain of PE; III: toxin domain of PE.
Figure 14:
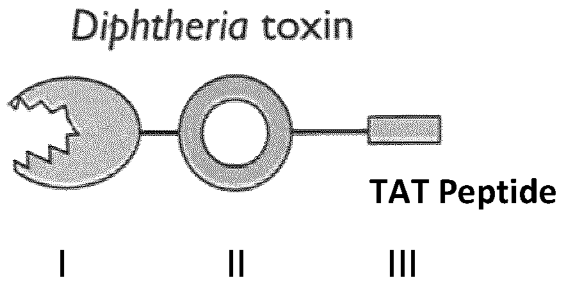
FIG. 14 shows a schematic diagram of a recombinant peptide-conjugated toxin fusion comprising translocation and toxin domain of Diphtheria toxin (DTA) and a third domain of TAT peptide. I: toxin domain of DTA; II: translocation domain of DTA; III: TAT peptide as the third domain.
Figure 15:
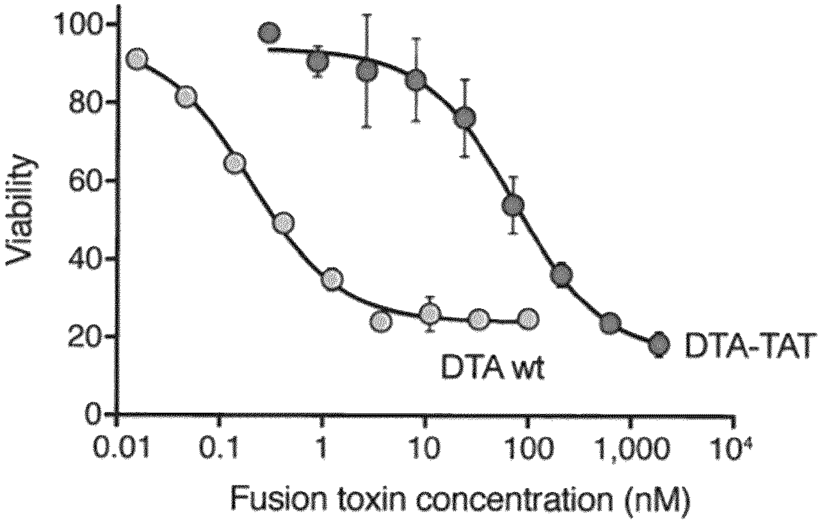
FIG. 15 shows a graph depicting different toxic effects of DTA-TAT (Diphtheria toxin fused with TAT peptide) and DTA-wild type (DTA-wt) having different on HEK293T cells.
Figure 16:
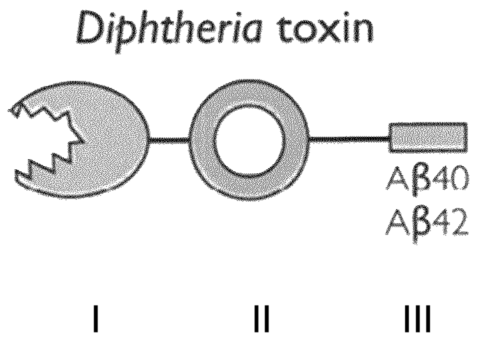
FIG. 16 shows a schematic diagram of a recombinant peptide-conjugated toxin fusion comprising translocation and toxin domain of Diphtheria toxin (DTA) and the binding domain is Aβ40 or Aβ42 peptide. I: toxin domain of DTA; II: translocation domain of DTA; III: binding domain is Aβ40 or Aβ42 peptide.
Figure 17A:
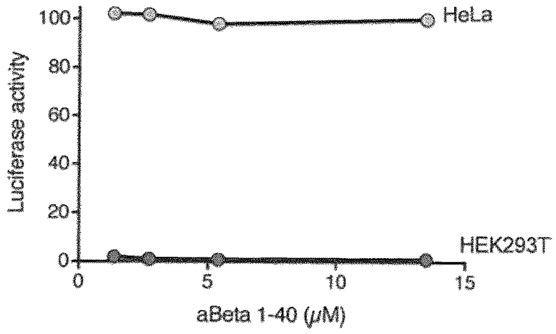
FIGS. 17A and B show toxic effects of DTA-Aβ40 (A), and DTA-Aβ42 (B) on HeLa an HEK293T cells. DTA-Aβ40: recombinant toxin fusion comprising translocation and toxin domain of Diphtheria toxin (DTA) and a binding domain of Aβ40 peptide; DTA-Aβ42: recombinant toxin fusion comprising translocation and toxin domain of Diphtheria toxin (DTA) and the binding domain is Aβ42 peptide.
Figure 17B:
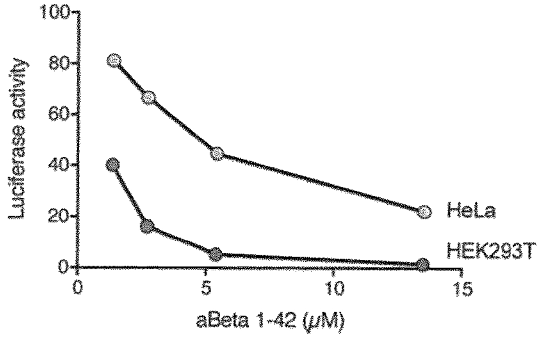

Further, different toxic effects are shown with CXCL9-PE (recombinant ligand-conjugated toxin fusion comprising translocation and toxin domain of Exotoxin A, and receptor-binding molecule CXCL9) and PTN-PE (recombinant ligand-conjugated toxin fusion comprising translocation and toxin domain of Exotoxin A, and receptor-binding molecule PTN) in HEK293T cells (FIG. 13). In addition, a recombinant toxin fusion comprising translocation and toxin domain of Diphtheria toxin and a binding domain of TAT peptide (FIG. 14) are shown to have different toxic effects on HEK293T cells than wild type Diphtheria toxin (FIG. 15). Furthermore, a recombinant toxin fusion comprising translocation and toxin domain of Diphtheria toxin and the binding domain is Aβ40 or Aβ42 peptide (FIG. 16) are shown to have different toxic effects on HeLa and HEK293T (FIG. 17). Without wishing to be bound by theory, these results suggest that the toxin gains entry into the cell through receptor-mediated endocytosis. These results show that recombinant exotoxins can be engineered to enter cells through alternative receptors or mechanisms (e.g. via adaptive translation in the case of TAT).

Discussion

These data demonstrate that the presently disclosed approach is a powerful platform for the discovery of cell surface receptors (and their quality control factors) for ligands such as secreted proteins. For example, the methods can be used in fundamental research to decipher the wiring of the extracellular protein/protein interaction network, leading to novel biological insights and drug targets. In regenerative medicine, the methods can for example be used to identify receptors and pathways that regulate the response of host tissue to engineered and engrafted cells. Furthermore, the identification of novel cell-type specific recombinant toxin fusions enables selective depletion of undesired cell types during in vitro differentiation. In cancer therapy, immunology and immuno-oncology, it can identify factors that regulate the binding of antibodies and other biologicals to their target cells. Finally, the skilled person in the art can readily modify the assay to identify cellular targets of small molecules that act through membrane proteins such as GPCRs.

Example 2

Figure 18:
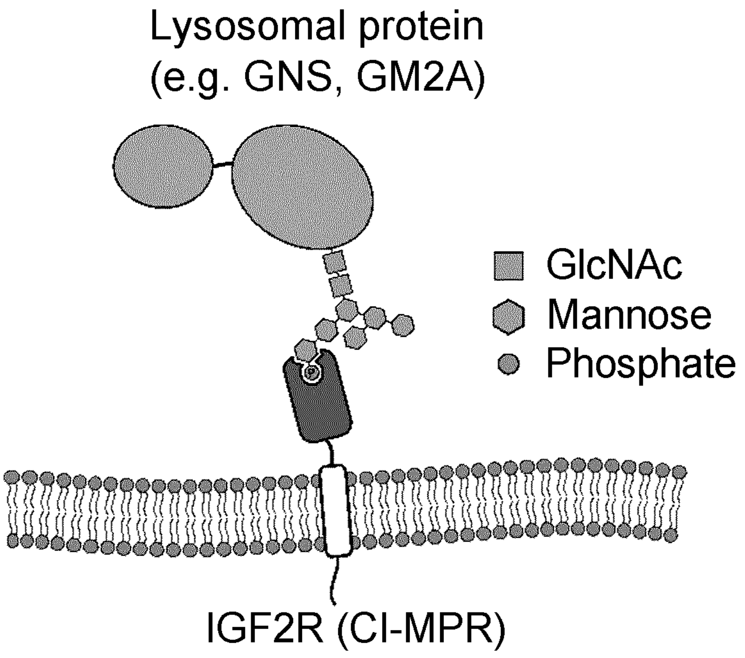
FIG. 18 shows a schematic diagram of cation-independent mannose-6-phosphate receptor (IGF2R) binding to mannose-6-phosphate tags of lysosomal protein.

Identification of Extracellular Interactions Dependent on Mannose-6-Phosphate Modification Extracellular interactions dependent on mannose-6-phosphate modification were identified in this Example. Trafficking of lysosomal proteins such as N-acetylglucosamine-6-sulfatase (GNS) and ganglioside GM2 activator (GM2A) to the lysosome is regulated by post-translational mannose-6-phosphate (M6P) modification. Cation-independent mannose-6-phosphate receptor (IGF2R, also known as CI-MPR) is localized on the cell surface or the lysosomal surface, where it binds M6P tags (FIG. 18). Genome-wide CRISPR/Cas9 screens were performed in HAP1 cells with GNS-PE38 (GNS fused to C-terminal fragment of exotoxin A (PE38)) and with GM2A-PE38 (GM2A fused to PE38) following the steps in Example 1. In both cases, IGF2R was the second most enriched gene in their respective screen, demonstrating that the screening platform can identify interactions dependent on post-translational modifications relating to secreted protein (Table 5 and Table 6). For GNS-PE38, the screen also identified VPS37A, PTPN23, HGS and UBAP1 which are involved in protein trafficking, and DPH1, DPH2, DPH5, DPH7, and DNAJC24 which are involved in diphthamide biosynthesis (Table 5A and B). For GM2A-PE38, the screen also identified KDELR1, KDELR2, DNAJC13, ARL5B, and ARFRP1 which are involved in protein trafficking, and DPH2 and DPH7 which are involved in diphthamide biosynthesis (Table 6A and B).

TABLE 5A

List of genes ranked by p-value that confers resistance to GNS-PE38 from a CRISPR screen in HAP1 cells. VPS37A, PTPN23, HGS and UBAP1 are involved in trafficking. IGF2R is a receptor for mannose-6-phosphate. DPH1, DPH2, DPH5, DPH7, and DNAJC24 are involved in diphthamide biosynthesis.

GNS-PE38

| Gene | Rank | p-value |
|---|---|---|
| DPH7 | 1 | 2.74E−07 |
| IGF2R | 2 | 2.74E−07 |
| DPH2 | 3 | 2.74E−07 |
| DPH5 | 4 | 2.74E−07 |
| DNAJC24 | 5 | 2.74E−07 |
| DPH1 | 6 | 2.74E−07 |
| VPS37A | 7 | 2.74E−07 |
| PTPN23 | 8 | 3.02E−06 |
| HGS | 9 | 1.92E−06 |
| UBAP1 | 10 | 3.26E−05 |

TABLE 5B

List of genes ranked by q-value that confers resistance to GNS-PE38 from a CRISPR screen in HAP1 cells. VPS37A, PTPN23, HGS and UBAP1 are involved in protein trafficking. IGF2R is a receptor for mannose-6-phosphate. DPH1, DPH2, DPH5, DPH7, and DNAJC24 are involved in diphthamide biosynthesis.

GNS-PE38

| Gene | Rank | q-value |
|---|---|---|
| DPH7 | 1 | 0.000707 |
| IGF2R | 2 | 0.000707 |
| DPH2 | 3 | 0.000707 |
| DPH5 | 4 | 0.000707 |
| DNAJC24 | 5 | 0.000707 |
| DPH1 | 6 | 0.000707 |
| VPS37A | 7 | 0.000707 |
| PTPN23 | 8 | 0.006051 |
| HGS | 9 | 0.004332 |
| UBAP1 | 10 | 0.058911 |
| USP8 | 11 | 0.068857 |
| DPH3 | 12 | 0.1283 |

TABLE 6A

List of genes ranked by p-value that confers resistance to GM2A-PE38 from a CRISPR screen in HAP1 cells. KDELR1, KDELR2, DNAJC13, ARL5B, and ARFRP1 are involved in protein trafficking. IGF2R is a receptor for mannose-6-phosphate. DPH2 and DPH7 are involved in diphthamide biosynthesis.

GM2A-PE38

| Gene | Rank | p-value |
|---|---|---|
| KDELR2 | 1 | 2.74E−07 |
| IGF2R | 2 | 8.23E−07 |
| KDELR1 | 3 | 3.57E−06 |
| DNAJC13 | 4 | 1.62E−05 |
| ARL5B | 5 | 3.59E−05 |
| ARFRP1 | 6 | 5.41E−05 |
| ZUFSP | 7 | 5.84E−05 |
| DPH7 | 8 | 9.19E−05 |
| DPH2 | 9 | 0.000107 |
| GH1 | 10 | 0.000232 |

TABLE 6B

List of genes ranked by q-value that confers resistance to GM2A-PE38 from a CRISPR screen in HAP1 cells. KDELR1, KDELR2, DNAJC13, ARL5B, and ARFRP1 are involved in protein trafficking. IGF2R is a receptor for mannose-6-phosphate. DPH2 and DPH7 are involved in diphthamide biosynthesis.

GM2A-PE38

| Gene | Rank | q-value |
|---|---|---|
| KDELR2 | 1 | 0.00495 |
| IGF2R | 2 | 0.007426 |
| KDELR1 | 3 | 0.021452 |
| DNAJC13 | 4 | 0.07302 |
| ARL5B | 5 | 0.129703 |
| ARFRP1 | 6 | 0.150636 |
| ZUFSP | 7 | 0.150636 |
| DPH7 | 8 | 0.207302 |
| DPH2 | 9 | 0.215072 |
| RPL13 | 10 | 0.376733 |
| GH1 | 11 | 0.381188 |
| CHST14 | 12 | 0.416254 |

Example 3

Figure 19A:
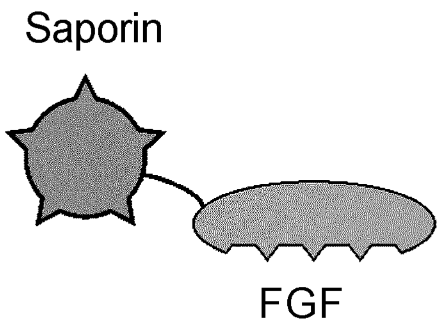
FIG. 19A shows fibroblast growth factor (FGF) fused with saporin.
Figure 19B:
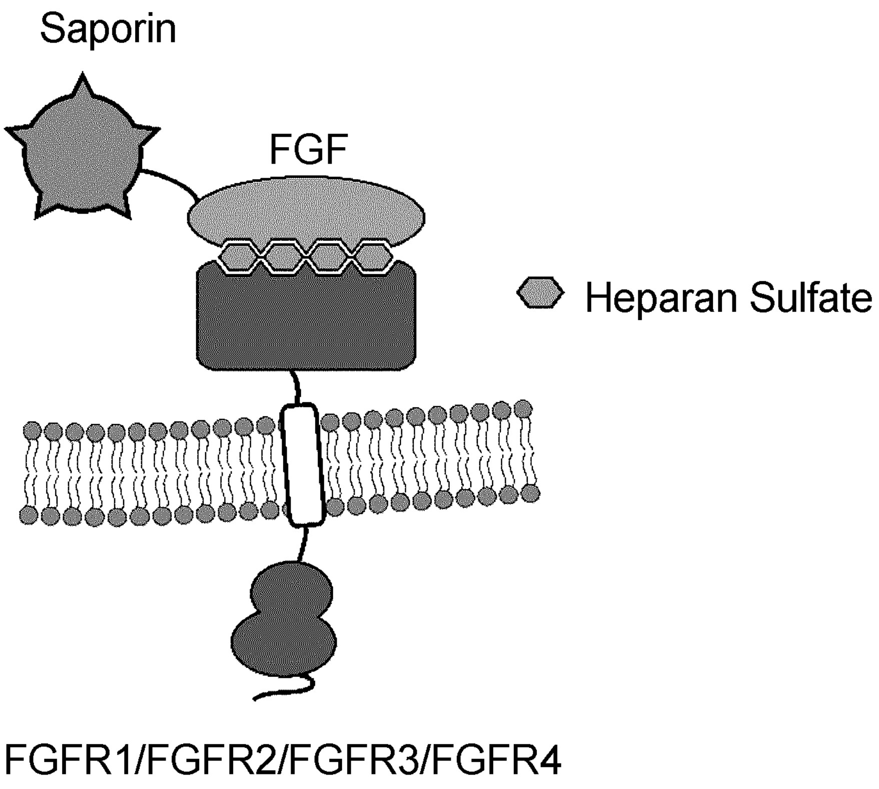
FIG. 19B shows a schematic diagram of heparin sulfate involved in FGF binding to FGF receptors (FGFR1, FGFR2, FGFR3, or FGFR4).

Identification of Extracellular Interactions Dependent on Glycosaminoglycans Extracellular interactions dependent on glycosaminoglycans were identified in this Example. Fibroblast growth factor (FGF) such as FGF2 is a cell signal protein that has a defining property of binding to heparin sulfate, a member of the glycosaminoglycan family of carbohydrates which consists of a variably sulfated repeating disaccharide unit. A genome-wide CRISPR/Cas9 screen was performed in HeLa cells with 6.5 nM FGF2-saporin (FGF2-saporin was purchased from Advanced Targeting Systems, product number IT-38; FGF2 fused to saporin (FIG. 19A)) following the steps in Example 1. As shown in Table 7, the most enriched genes conferring resistance were involved in glycosaminoglycan biosynthesis pathway, consistent with the established role of heparan sulfates in FGF/FGFR interaction (FIG. 19B), whereby heparin sulfate is required for FGF interactions with FGFR1, FGFR2, FGFR3, or FGFR4. Moreover, the results show that saporin, a plant toxin derived from common soapwort, can be used as the intoxication factor in the screening platform.

TABLE 7

List of genes that confers resistance to FGF2-saporin from a CRISPR screen in HeLa cells. EXT2, EXT1, TMEM165, GUSB, SLC35B2, B3GAT3, and EXTL3 are involved in glycosaminoglycan biogenesis.

FGF2-saporin

| Gene | Rank | q-value |
|---|---|---|
| EXT2 | 1 | 7.86e−23 |
| SLC39A9 | 2 | 1.51e−18 |
| EXT1 | 3 | 5.13e−18 |
| TMEM165 | 4 | 3.38e−12 |
| PFKFB1 | 5 | 2.96e−09 |
| GUSB | 6 | 1.71e−07 |
| SLC35B2 | 7 | 2.50e−07 |
| SETD3 | 8 | 7.07e−07 |
| RPS6KB1 | 9 | 8.41e−07 |
| B3GAT3 | 10 | 8.62e−07 |
| BRK1 | 11 | 2.35e−06 |
| FAHD2B | 12 | 4.95e−06 |
| EXTL3 | 13 | 1.59e−05 |

Example 4

Screening Platform Utilizing Subtilase Exotoxin

Figure 20:
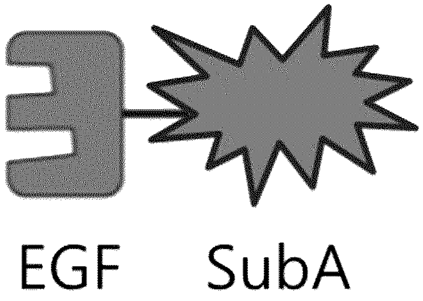
FIG. 20 shows a schematic diagram of a recombinant toxin fusion comprising EGF and subtilase exotoxin (SubA).

The present disclosure provides a screening platform that is compatible with different toxins. The use of subtilase exotoxin as part of a probe for screening was shown in this Example. A genome-wide CRISPR/Cas9 screen following the steps in Example 1 was performed in A549 cells with 20 nM EGF-SubA, which was obtained from SibTech, Inc (Brookfield, Connecticut, USA; Cat #SBT077-012) (FIG. 20), where SubA is the toxin domain of subtilase exotoxin. As shown in Table 8, the most enriched gene in the surviving cell population was the EGF receptor (EGFR). These results, in view of the results shown above in Example 1, demonstrated that the screening platform disclosed herein is compatible with different toxins (e.g. SubA and PE) fused to the same ligand (e.g. EGF).

TABLE 8

List of genes that confers resistance to EGF-subtilase cytotoxin (SubA) from a CRISPR screen in A549 cells. KDELR1, KDELR2, and TAPT1 are involved in protein trafficking. EGFR is a receptor for EGF.

EGF-SubA

| Gene | Rank | p-value |
|---|---|---|
| EGFR | 1 | 2.74E−07 |
| KDELR1 | 2 | 2.74E−07 |
| TPX2 | 3 | 3.57E−06 |
| KDELR2 | 4 | 1.95E−05 |
| MRPL37 | 5 | 3.59E−05 |
| TAPT1 | 6 | 5.02E−05 |
| WNT3 | 7 | 0.000107 |
| CIAO1 | 8 | 0.000116 |
| FCRL2 | 9 | 0.000152 |
| LRFN3 | 10 | 0.000183 |

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

The scope of the claims should not be limited by the preferred embodiments and examples, but should be given the broadest interpretation consistent with the description as a whole.

REFERENCES

Brown, K. J. et al. The human secretome atlas initiative: implications in health and disease conditions. Biochimica et biophysica acta 1834, 2454-2461, doi:10.1016/j.bbapap.2013.04.007 (2013).

Ben-Shlomo, I., Yu Hsu, S., Rauch, R., Kowalski, H. W. & Hsueh, A. J. Signaling receptome: a genomic and evolutionary perspective of plasma membrane receptors involved in signal transduction. Science's STKE: signal transduction knowledge environment 2003, RE9, doi:10.1126/stke.2003.187.re9 (2003).

Meissner, F., Scheltema, R. A., Mollenkopf, H. J. & Mann, M. Direct proteomic quantification of the secretome of activated immune cells. Science 340, 475-478, doi:10.1126/science.1232578 (2013).

Christopoulos, A. Allosteric binding sites on cell-surface receptors: novel targets for drug discovery. Nature reviews. Drug discovery 1, 198-210, doi:10.1038/nrd746 (2002).

Ramilowski, J. A. et al. A draft network of ligand-receptor-mediated multicellular signalling in human. Nature communications 6, 7866, doi:10.1038/ncomms8866 (2015).

Kerr, J. S. & Wright, G. J. Avidity-based extracellular interaction screening (AVEXIS) for the scalable detection of low-affinity extracellular receptor-ligand interactions. Journal of visualized experiments: JoVE, e3881, doi:10.3791/3881 (2012).

Michalska, M. & Wolf, P. *Pseudomonas* Exotoxin A: optimized by evolution for effective killing. Frontiers in microbiology 6, 963, doi:10.3389/fmicb.2015.00963 (2015).

Carette, J. E. et al. Haploid genetic screens in human cells identify host factors used by pathogens. Science 326, 1231-1235, doi:10.1126/science.1178955 (2009).

Hu, Y. et al. Specific killing of CCR9 high-expressing acute T lymphocytic leukemia cells by CCL25 fused with PE38 toxin. Leukemia research 35, 1254-1260, doi:10.1016/j.leukres.2011.01.015 (2011).

Weldon, J. E. & Pastan, I. A guide to taming a toxin—recombinant immunotoxins constructed from *Pseudomonas* exotoxin A for the treatment of cancer. The FEBS journal 278, 4683-4700, doi:10.1111/j.1742-4658.2011.08182.x (2011).

Foss, F. M. DAB(389)IL-2 (ONTAK): a novel fusion toxin therapy for lymphoma. Clinical lymphoma 1, 110-116; discussion 117 (2000).

Pasetto, M. et al. Whole-genome RNAi screen highlights components of the endoplasmic reticulum/Golgi as a source of resistance to immunotoxin-mediated cytotoxicity. Proceedings of the National Academy of Sciences of the United States of America 112, E1135-1142, doi:10.1073/pnas.1501958112 (2015).

Jae, L. T. et al. Deciphering the glycosylome of dystroglycanopathies using haploid screens for lassa virus entry. Science 340, 479-483, doi:10.1126/science.1233675 (2013).

Mitamura, T., Higashiyama, S., Taniguchi, N., Klagsbrun, M. & Mekada, E. Diphtheria toxin binds to the epidermal growth factor (EGF)-like domain of human heparin-binding EGF-like growth factor/diphtheria toxin receptor and inhibits specifically its mitogenic activity. The Journal of biological chemistry 270, 1015-1019 (1995).

Hart, T. et al. High-Resolution CRISPR Screens Reveal Fitness Genes and Genotype-Specific Cancer Liabilities. Cell 163, 1515-1526, doi:10.1016/j.cell.2015.11.015 (2015).

Korf-Klingebiel, M. et al. Myeloid-derived growth factor (C19orf10) mediates cardiac repair following myocardial infarction. Nature medicine 21, 140-149, doi:10.1038/nm.3778 (2015).

Li, W. et al. MAGeCK enables robust identification of essential genes from genome-scale CRISPR/Cas9 knockout screens. Genome biology 15, 554 (2014).

WO2011006145A2

We claim:

1. A method for identifying a protein associated with a receptor-ligand interaction, comprising the steps of:

(a) providing a population of engineered mammalian cells that express the receptor or ligand and comprise a mammalian targeting library, wherein an individual engineered cell of the population contains a nucleic acid molecule of the targeting library, and wherein the nucleic acid molecule comprises a nucleic acid sequence complementary to a target gene;

(b) contacting the population of engineered mammalian cells for sufficient time with a recombinant toxin fusion comprising a toxin domain, a binding domain that binds the receptor or the ligand and optionally a translocation domain, thereby producing a selection pool of cells that have survived killing by the recombinant toxin fusion; and (c) sequencing one or more of the nucleic acid molecule of the mammalian targeting library comprised in the selection pool of cells, thereby identifying the target gene, wherein the target gene encodes the protein associated with a receptor-ligand interaction; and wherein the binding domain is a non toxin protein.

2. The method of claim 1, wherein the nucleic acid molecule targeting specific gene expression comprises a gRNA, siRNA, shRNA or miRNA.

3. The method of claim 2, wherein the gRNA is part of a CRISPR-Cas system, optionally wherein the CRISPR-Cas system comprises Cas9.

4. The method of claim 1, wherein the mammalian targeting library is a mammalian library, optionally a human or mouse library, and/or wherein the mammalian targeting library is a whole genome library.

5. The method of claim 1, wherein the mammalian targeting library comprises nucleic acid molecules targeting cell surface receptors, nucleic acid molecules targeting proteins of cell surface receptor-mediated pathways and/or nucleic acid molecules targeting receptor maturation factors.

6. The method of claim 1, wherein the toxin domain is or comprises Diphtheria toxin (DTA), *Pseudomonas* exotoxin A (PE), saporin, gelonin, perfringolysin, listeriolysin, α-hemolysin, subtilase cytotoxin, bouganin, or ricin toxin domain, or a toxic fragment thereof.

7. The method of claim 1, wherein the non toxin protein is a receptor-binding molecule or a binding fragment thereof, a peptide or a binding fragment thereof, an antibody or a binding fragment thereof, a carbohydrate, a small molecule, or a lipid.

8. The method of claim 7, wherein the receptor-binding molecule is or comprises EGF, PTN, CXCL9, GNS, GM2A or FGF, or a binding fragment thereof or wherein the peptide is or comprises a TAT peptide, Aβ40 or Aβ42, or a binding fragment thereof.

9. The method of claim 1, wherein the binding domain comprises a post-translational modification, optionally wherein the post-translational modification is or comprises phosphorylation, acetylation, glycosylation, amidation, hydroxylation, methylation, ubiquitylation, or mannose-6-phosphate addition.

10. The method of claim 1, wherein the translocation domain is or comprises DTA or PE translocation domain, or a transmembrane passage forming fragment thereof.

11. The method of claim 1, wherein the toxin domain is at the amino or carboxyl terminus of the recombinant toxin fusion, optionally wherein the binding domain is at an opposite terminus of the toxin domain.

12. The method claim 1, wherein the recombinant toxin fusion when administered to cells kills at least 99% of non-engineered cells.

13. The method of claim 1, wherein the recombinant toxin fusion further comprises a translocation domain.

14. The method of claim 3, wherein the CRISPR-Cas system comprises Cas9.

15. The method of claim 9, wherein the post-translational modification is or comprises phosphorylation, acetylation, glycosylation, amidation, hydroxylation, methylation, ubiquitylation, or mannose-6-phosphate addition.

16. The method of claim 11, wherein the binding domain is at an opposite terminus of the toxin domain.

17. The method of claim 1, wherein the binding domain is a secreted protein.

18. The method of claim 5, wherein the cell surface receptors are G protein coupled receptors (GPCRs).

19. The method of claim 7, wherein the receptor-binding molecule is or comprises a ligand, or a binding fragment thereof.

20. The method of claim 19, wherein the ligand is an orphan ligand.

* * * * *